US010355229B2

United States Patent
Lieber et al.

(10) Patent No.: US 10,355,229 B2
(45) Date of Patent: Jul. 16, 2019

(54) METHODS AND SYSTEMS FOR SCAFFOLDS COMPRISING NANOELECTRONIC COMPONENTS

(71) Applicant: President and Fellows of Harvard College, Cambridge, MA (US)

(72) Inventors: Charles M. Lieber, Lexington, MA (US); Bozhi Tian, Chicago, IL (US); Jia Liu, Palo Alto, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 25 days.

(21) Appl. No.: 15/205,373

(22) Filed: Jul. 8, 2016

(65) Prior Publication Data

US 2017/0069858 A1    Mar. 9, 2017

Related U.S. Application Data

(63) Continuation of application No. 14/018,075, filed on Sep. 4, 2013, now Pat. No. 9,786,850.
(Continued)

(51) Int. Cl.
*C12M 1/12* (2006.01)
*C12N 5/00* (2006.01)
(Continued)

(52) U.S. Cl.
CPC ........ *H01L 51/0504* (2013.01); *A61L 27/025* (2013.01); *A61L 27/18* (2013.01);
(Continued)

(58) Field of Classification Search
None
See application file for complete search history.

(56) References Cited

U.S. PATENT DOCUMENTS 2,820,743 A * 1/1958 Alheritiere ............... B01D 3/40
203/84
5,797,898 A * 8/1998 Santini, Jr. ........... A61K 9/0009
604/890.1
(Continued)

FOREIGN PATENT DOCUMENTS

DE    10159415 B4 * 10/2012 ......... H01F 17/0006
EP    2023357 A1 *  2/2009 ......... B81C 1/0019
(Continued)

OTHER PUBLICATIONS

Invitation to Pay Additional Fees dated Jul. 31, 2014 for Application No. PCT/US2014/032743.
(Continued)

*Primary Examiner* — David E Graybill
(74) *Attorney, Agent, or Firm* — Wolf, Greenfield & Sacks, P.C.

(57) ABSTRACT

The present invention generally relates to nanoscale wires and tissue engineering. Systems and methods are provided in various embodiments for preparing cell scaffolds that can be used for growing cells or tissues, where the cell scaffolds comprise nanoscale wires. In some cases, the nanoscale wires can be connected to electronic circuits extending externally of the cell scaffold. Such cell scaffolds can be used to grow cells or tissues which can be determined and/or controlled at very high resolutions, due to the presence of the nanoscale wires, and such cell scaffolds will find use in a wide variety of novel applications, including applications in tissue engineering, prosthetics, pacemakers, implants, or the like. This approach thus allows for the creation of fundamentally new types of functionalized cells and tissues, due to the high degree of electronic control offered by the nanoscale wires and electronic circuits.

22 Claims, 35 Drawing Sheets

| | |
|---|---|
| Coating Polymer | 240 |
| Metal Lead | 235 |
| Lead Polymer | 230 |
| Nanoscale Wire | 225 |
| Bedding Polymer | 220 |
| Sacrificial Material | 215 |
| Initial Polymer | 210 |
| Oxidized Layer | 205 |
| Substrate | 200 |

US 10,355,229 B2
Page 2

Related U.S. Application Data

(60) Provisional application No. 61/723,213, filed on Nov. 6, 2012, provisional application No. 61/698,492, filed on Sep. 7, 2012.

(51) Int. Cl.

| | | |
|---|---|---|
| *A61L 27/02* | (2006.01) | |
| *A61L 27/18* | (2006.01) | |
| *A61L 27/20* | (2006.01) | |
| *A61L 27/24* | (2006.01) | |
| *A61L 27/36* | (2006.01) | |
| *A61L 27/38* | (2006.01) | |
| *A61L 27/40* | (2006.01) | |
| *A61L 27/50* | (2006.01) | |
| *A61L 27/56* | (2006.01) | |
| *B82Y 15/00* | (2011.01) | |
| *H01L 51/00* | (2006.01) | |
| *H01L 51/05* | (2006.01) | |
| *G01N 27/414* | (2006.01) | |

(52) U.S. Cl.
CPC .............. *A61L 27/20* (2013.01); *A61L 27/24* (2013.01); *A61L 27/3633* (2013.01); *A61L 27/38* (2013.01); *A61L 27/3826* (2013.01); *A61L 27/40* (2013.01); *A61L 27/50* (2013.01); *A61L 27/56* (2013.01); *C12M 25/14* (2013.01); *C12N 5/0068* (2013.01); *G01N 27/4145* (2013.01); *G01N 27/4146* (2013.01); *H01L 51/003* (2013.01); *H01L 51/0017* (2013.01); *H01L 51/0021* (2013.01); *H01L 51/0093* (2013.01); *H01L 51/0575* (2013.01); *A61L 2400/08* (2013.01); *A61L 2400/12* (2013.01); *B82Y 15/00* (2013.01); *C12N 2533/00* (2013.01); *C12N 2533/30* (2013.01); *C12N 2533/40* (2013.01); *C12N 2533/54* (2013.01); *C12N 2533/74* (2013.01); *C12N 2533/90* (2013.01)

(56) References Cited

U.S. PATENT DOCUMENTS

| | | | | |
|---|---|---|---|---|
| 5,994,750 A * | 11/1999 | Yagi | ............. | H01H 59/0009 200/181 |
| 6,322,713 B1 * | 11/2001 | Choi | ............. | B82Y 10/00 216/38 |
| 7,129,554 B2 * | 10/2006 | Lieber | ............. | B82Y 10/00 257/414 |
| 7,211,464 B2 | 5/2007 | Lieber et al. | | |
| 7,301,199 B2 | 11/2007 | Lieber et al. | | |
| 7,701,428 B2 * | 4/2010 | Stumbo | ............. | B82Y 10/00 345/87 |
| 7,707,714 B2 * | 5/2010 | Schmidt | ............. | H01F 17/0006 29/605 |
| 7,838,950 B2 * | 11/2010 | Detlev | ............. | H01L 29/78687 257/414 |
| 8,136,213 B2 * | 3/2012 | Schmidt | ............. | B81C 1/0019 29/25.42 |
| 8,179,026 B2 * | 5/2012 | Russell | ............. | H01L 41/193 310/311 |
| 8,313,966 B2 * | 11/2012 | Mi | ............. | B82Y 10/00 257/E21.22 |
| 8,398,949 B2 * | 3/2013 | Meyer | ............. | A61K 33/44 423/447.1 |
| 8,414,908 B2 * | 4/2013 | Jin | ............. | A61K 9/0009 424/423 |
| 8,861,184 B2 * | 10/2014 | Schmidt | ............. | B81C 1/0019 361/511 |
| 8,956,637 B2 * | 2/2015 | Dubrow | ............. | A61F 13/02 424/422 |
| 9,037,214 B2 * | 5/2015 | Chen | ............. | A61K 49/0002 600/420 |
| 9,114,009 B2 * | 8/2015 | Dvir | ............. | A61L 27/44 |
| 9,273,277 B2 * | 3/2016 | Jin | ............. | A61K 9/0009 |
| 9,349,543 B2 * | 5/2016 | Lyon | ............. | H01G 11/36 |
| 9,375,873 B2 * | 6/2016 | Gracias | ............. | B01L 3/502707 |
| 9,431,082 B2 * | 8/2016 | Makarov | ............. | G11C 11/14 |
| 9,457,128 B2 | 10/2016 | Lieber et al. | | |
| 9,539,643 B2 * | 1/2017 | Sun | ............. | B22F 9/24 |
| 9,704,908 B2 * | 7/2017 | Graff | ............. | H01L 27/14683 |
| 9,786,850 B2 | 10/2017 | Lieber et al. | | |
| 9,976,120 B2 * | 5/2018 | Blick | ............. | C12M 25/14 |
| 2003/0012723 A1 | 1/2003 | Clarke | | |
| 2003/0060836 A1 | 3/2003 | Wang et al. | | |
| 2003/0089899 A1 | 5/2003 | Lieber et al. | | |
| 2003/0189202 A1 | 10/2003 | Li et al. | | |
| 2004/0036128 A1 | 2/2004 | Zhang et al. | | |
| 2005/0038498 A1 * | 2/2005 | Dubrow | ............. | A61L 31/14 623/1.15 |
| 2005/0064618 A1 | 3/2005 | Brown et al. | | |
| 2005/0079659 A1 | 4/2005 | Duan et al. | | |
| 2005/0118733 A1 * | 6/2005 | Schmidt | ............. | H01F 17/0006 438/3 |
| 2005/0253137 A1 * | 11/2005 | Whang | ............. | B82Y 10/00 257/40 |
| 2006/0019472 A1 * | 1/2006 | Pan | ............. | B82Y 10/00 438/486 |
| 2006/0054936 A1 * | 3/2006 | Lieber | ............. | B82Y 10/00 257/210 |
| 2006/0118514 A1 * | 6/2006 | Little | ............. | B82Y 30/00 216/41 |
| 2006/0256059 A1 | 11/2006 | Stumbo et al. | | |
| 2007/0048383 A1 * | 3/2007 | Helmus | ............. | A61K 9/0019 424/489 |
| 2007/0077429 A1 * | 4/2007 | Mirkin | ............. | B82Y 5/00 428/402 |
| 2007/0176824 A1 * | 8/2007 | Stumbo | ............. | H01Q 3/34 342/372 |
| 2007/0269481 A1 * | 11/2007 | Li | ............. | A61L 27/18 424/423 |
| 2008/0034921 A1 * | 2/2008 | Vanheusden | ............. | B22F 1/0022 75/362 |
| 2008/0061798 A1 * | 3/2008 | Blick | ............. | G01N 23/00 324/642 |
| 2008/0191242 A1 * | 8/2008 | Detlev | ............. | H01L 29/785 257/190 |
| 2008/0220042 A1 * | 9/2008 | Hashi | ............. | A61K 38/58 514/1.1 |
| 2008/0300663 A1 * | 12/2008 | Blick | ............. | A61N 1/375 607/116 |
| 2009/0046414 A1 * | 2/2009 | Schmidt | ............. | B81C 1/0019 361/523 |
| 2009/0124705 A1 * | 5/2009 | Meyer | ............. | A61K 33/44 514/769 |
| 2009/0220561 A1 * | 9/2009 | Jin | ............. | A61K 9/0009 424/423 |
| 2009/0258438 A1 | 10/2009 | Maki | | |
| 2010/0003421 A1 * | 1/2010 | Ebels | ............. | B81C 99/0085 427/532 |
| 2010/0051331 A1 * | 3/2010 | Tsai | ............. | B82Y 10/00 174/256 |
| 2010/0292791 A1 * | 11/2010 | Lu | ............. | A61K 38/18 623/13.12 |
| 2010/0303722 A1 * | 12/2010 | Jin | ............. | A61L 27/30 424/9.1 |
| 2011/0163421 A1 * | 7/2011 | Mi | ............. | B82Y 10/00 257/618 |
| 2011/0197710 A1 * | 8/2011 | Sun | ............. | B22F 9/24 75/351 |
| 2011/0201984 A1 * | 8/2011 | Dubrow | ............. | A61F 13/02 602/54 |
| 2011/0206905 A1 * | 8/2011 | Buriak | ............. | B82Y 30/00 428/172 |
| 2011/0223484 A1 * | 9/2011 | Korgel | ............. | B82Y 30/00 429/231.5 |
| 2011/0309306 A1 * | 12/2011 | Zhou | ............. | B82Y 40/00 252/500 |

(56) References Cited

U.S. PATENT DOCUMENTS

| | | | | |
|---|---|---|---|---|
| 2012/0064628 | A1* | 3/2012 | Blick | C12M 25/14 435/399 |
| 2012/0065703 | A1* | 3/2012 | Paukshto | A61L 27/446 607/50 |
| 2012/0079921 | A2* | 4/2012 | Monahan | B25B 15/02 81/180.1 |
| 2012/0126449 | A1* | 5/2012 | Hart | B29C 70/14 264/220 |
| 2012/0140379 | A1* | 6/2012 | Schmidt | B81C 1/0019 361/500 |
| 2013/0022648 | A1* | 1/2013 | Maginness | A61L 27/52 424/400 |
| 2013/0183352 | A1* | 7/2013 | Xie | A61L 27/446 424/400 |
| 2013/0289687 | A1* | 10/2013 | Dvir | A61L 27/44 607/129 |
| 2013/0296929 | A1* | 11/2013 | Lv | A61L 27/227 606/213 |
| 2014/0030553 | A1* | 1/2014 | Makarov | G11C 11/14 428/832.1 |
| 2014/0073063 | A1 | 3/2014 | Lieber et al. | |
| 2014/0074253 | A1* | 3/2014 | Lieber | A61L 27/025 623/23.72 |
| 2014/0079921 | A1* | 3/2014 | De Volder | B82Y 30/00 428/196 |
| 2014/0144881 | A1* | 5/2014 | Lee | H01L 29/0673 216/100 |
| 2015/0155167 | A1* | 6/2015 | Ohlsson | B82Y 10/00 257/9 |
| 2015/0351691 | A1* | 12/2015 | Lieber | A61L 27/18 600/361 |
| 2016/0027846 | A1 | 1/2016 | Lieber et al. | |
| 2017/0069858 | A1 | 3/2017 | Lieber et al. | |
| 2017/0072109 | A1 | 3/2017 | Lieber et al. | |

FOREIGN PATENT DOCUMENTS

| | | | |
|---|---|---|---|
| EP | 2423162 A1 * | 2/2012 | B82Y 30/00 |
| WO | WO 03048032 A1 * | 6/2003 | H01F 17/0006 |
| WO | WO 2009100988 A2 * | 8/2009 | B81C 99/008 |
| WO | WO 2012/100574 A1 | 8/2012 | |

OTHER PUBLICATIONS

International Search Report and Written Opinion dated Oct. 7, 2014 for Application No. PCT/US2014/032743.

International Preliminary Report on Patentability for Application No. PCT/US2014/032743 dated Oct. 15, 2015.

Office Action dated Apr. 24, 2015 for U.S. Appl. No. 14/018,075.
Office Action dated Nov. 5, 2015 for U.S. Appl. No. 14/018,075.
Office Action dated Jul. 7, 2015 for U.S. Appl. No. 14/018,082.
Office Action dated Aug. 9, 2016 for U.S. Appl. No. 14/782,161.
Office Action dated Nov. 3, 2016 for U.S. Appl. No. 14/782,161.
Office Action dated Jul. 14, 2017 for U.S. Appl. No. 14/782,161.
Office Action dated Nov. 17, 2017 for U.S. Appl. No. 14/782,161.
Chan et al., Scaffolding in tissue engineering: general approaches and tissue-specific considerations. Eur Spine J. Dec. 2008;17:S467-79.DOI 10.1007/s00586-008-0745-3.
Cui et al., Nanowire nanosensors for highly sensitive and selective detection of biological and chemical species. Science. Aug. 17, 2001. 293:1289-92. DOI: 10.1126/science.1062711.
Liu et al., Multifunctional three-dimensional macroporous nanoelectronic networks for smart materials. Proc Natl Acad Sci U S A. Apr. 23, 2013;110(17):6694-9. Epub Apr. 8, 2013. Supporting Information included. 6 pages.
Long et al., Recent advances in large-scale assembly of semiconducting inorganic nanowires and nanofibers for electronics, sensors and photovoltaics. Chem Soc Rev. May 9, 2012; 41:4560-4580. Retrieved from the Internet on Jul. 7, 2014. <URL: http://www.ece.ust.hk/~eezfan/Papers/54-2012CheScoRev.pdf>.
McAlpine et al. Highly ordered nanowire arrays on plastic substrates for ultrasensitive flexible chemical sensors. Nature Materials. 2007; 6:379-384.
Ryu et al., Lateral buckling mechanics in silicon nanowires on elastomeric substrates. Nano Letters. Jul. 17, 2009; 9(9):3214-3219. Retrieved from the Internet on Jul. 7, 2014. <URL: http://rogers.matse.illinois.edu/files/2009/wavynwnanolett.pdf>.
Tian et al., Macroporous nanowire nanoelectric scaffolds for synthetic tissues. Nature Mater. Aug. 26, 2012;11:986-94.
Tian et al., Macroporous nanowire nanoelectric scaffolds for synthetic tissues. Nature Mater. Aug. 26, 2012;11:986-94. Supplementary Information. 27 pages.
Tian et al., Three-dimensional, flexible nanoscale field-effect transistors as localized bioprobes. Science. Aug. 13, 2010;329:830-4.
Wang et al., Electrochemical fabrication of conducting polymer nanowires in an integrated microfluidic system. Chem Commun. Jun. 14, 2006; pp. 3075-3077. Retrieved from the Internet on Jul. 2, 2014. <URL: http://authors.library.caltech.edu/4231/1/WANcc06.pdf.
Zheng et al., Nanowire biosnesors for label-free, real-time, ultrasensitive protein detection. Methods Mol Biol. Aug. 18, 2011; 790:223-237. Retrieved from the Internet on Aug. 27, 2014. <URL: http://www.ncbi.nlm.nih.gov/pmc/articles/PMC3623691/pdf/nihms451957.pdf>.
Office Action dated May 3, 2018 for U.S. Appl. No. 14/782,161.
Office Action dated Aug. 27, 2018 for U.S. Appl. No. 14/782,161.

* cited by examiner

| | |
|---|---|
| Coating Polymer | 240 |
| Metal Lead | 235 |
| Lead Polymer | 230 |
| Nanoscale Wire | 225 |
| Bedding Polymer | 220 |
| Sacrificial Material | 215 |
| Initial Polymer | 210 |
| Oxidized Layer | 205 |
| Substrate | 200 |

Fig. 2

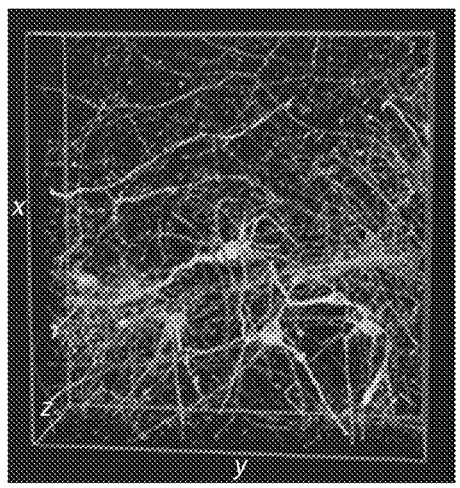
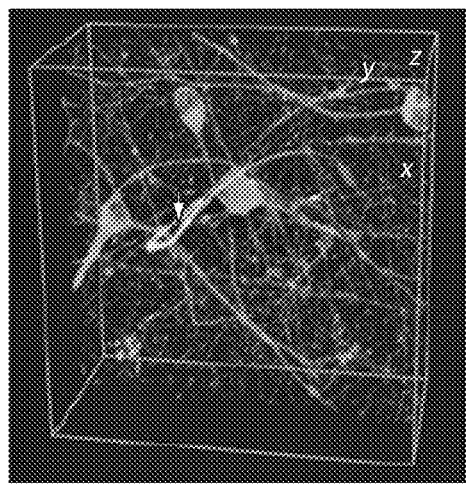
Fig. 10A
Fig. 10B
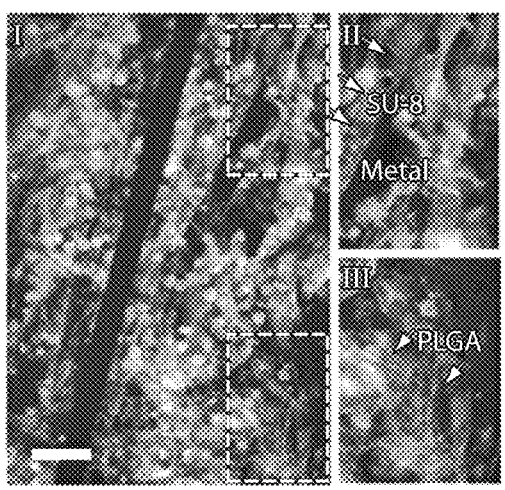
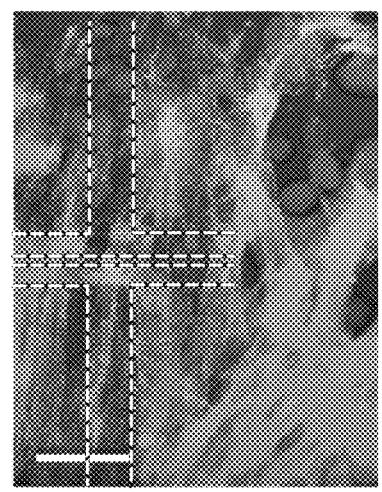
Fig. 10C
Fig. 10D

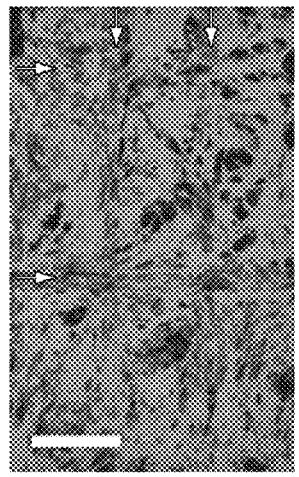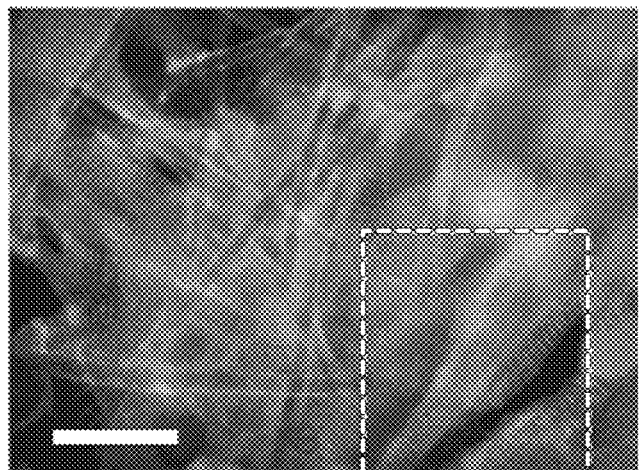
Fig. 13A　　　　　Fig. 13B
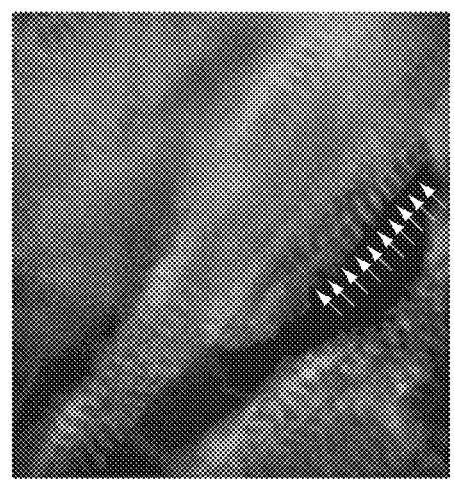
Fig. 13C

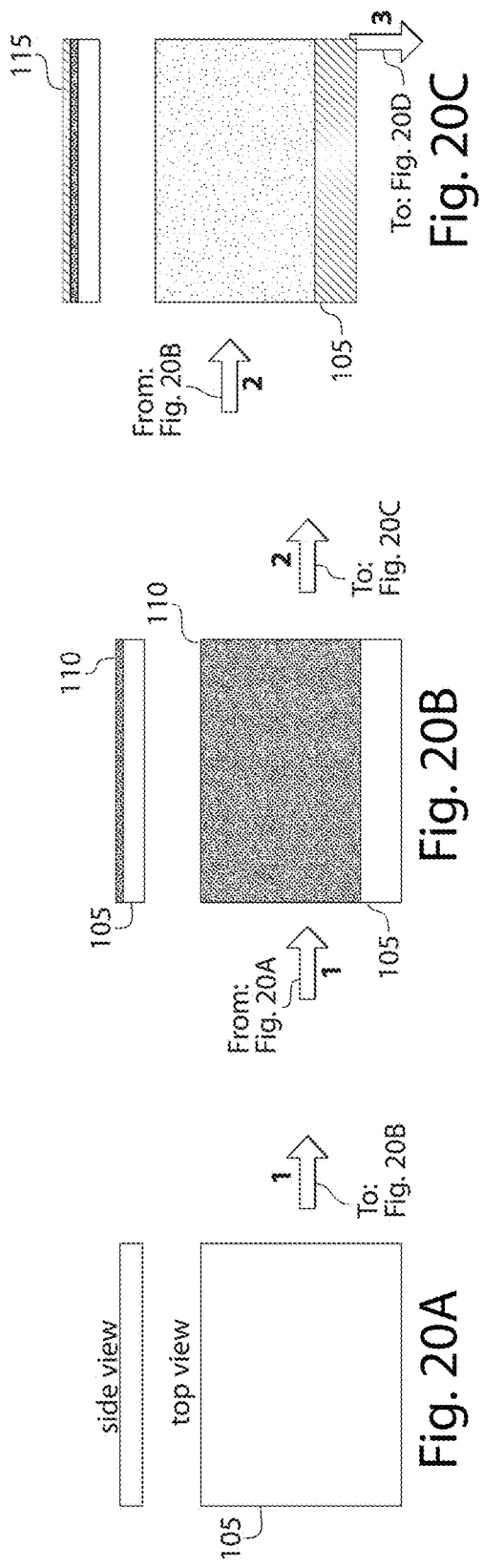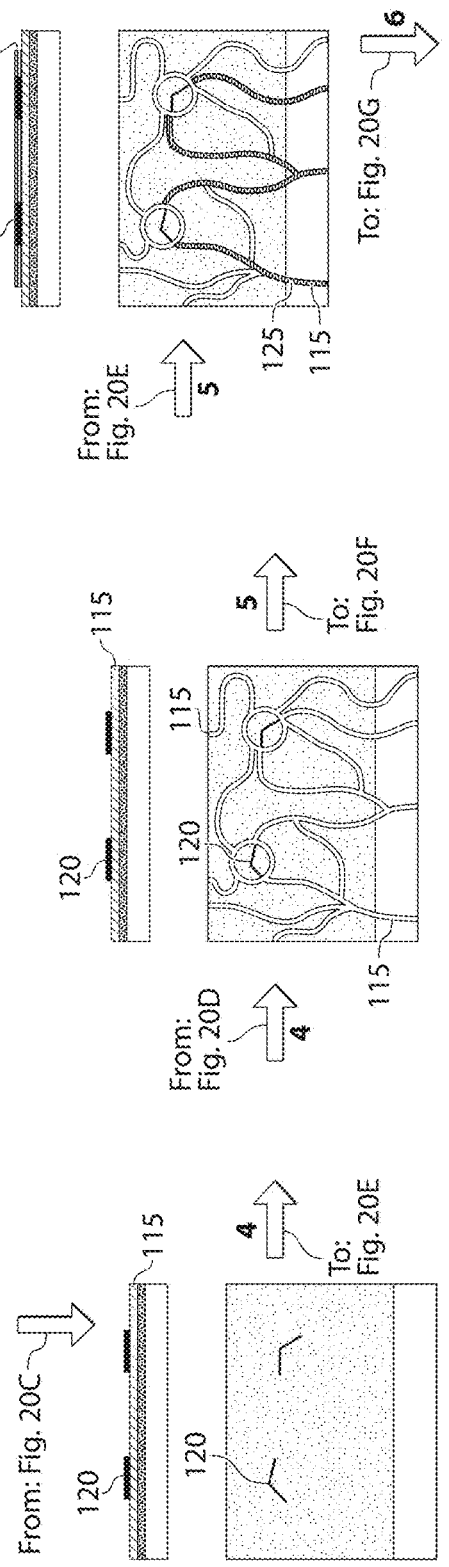

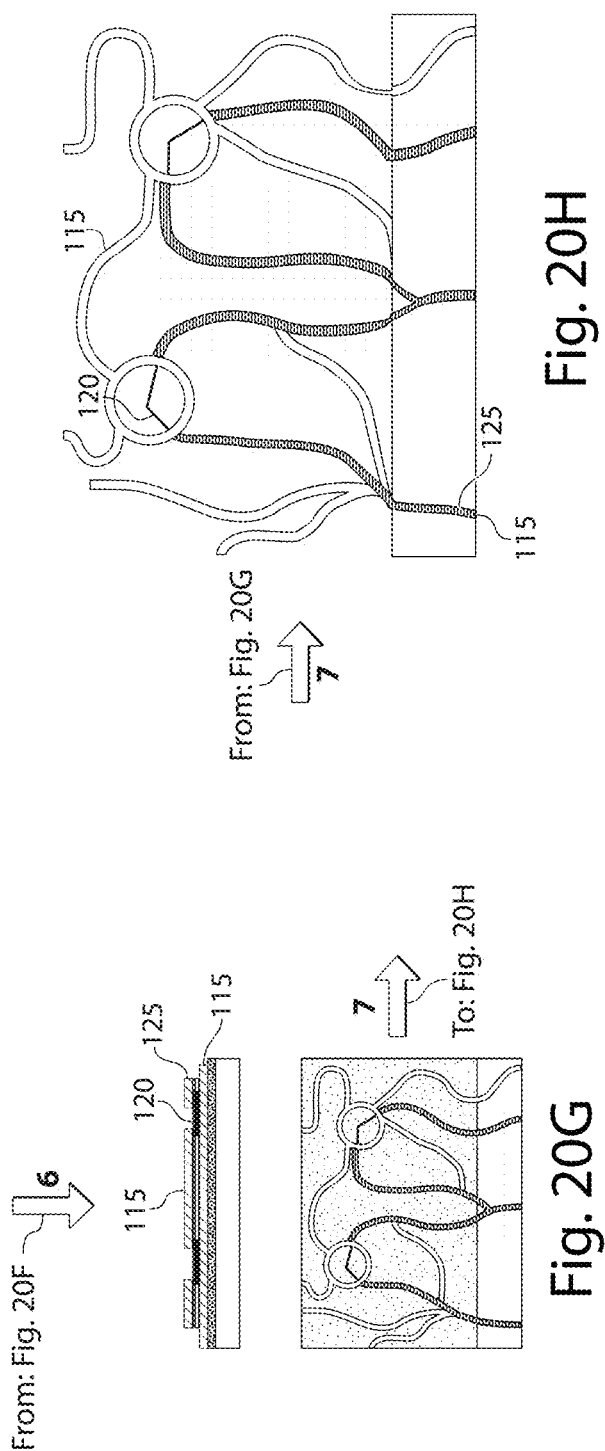

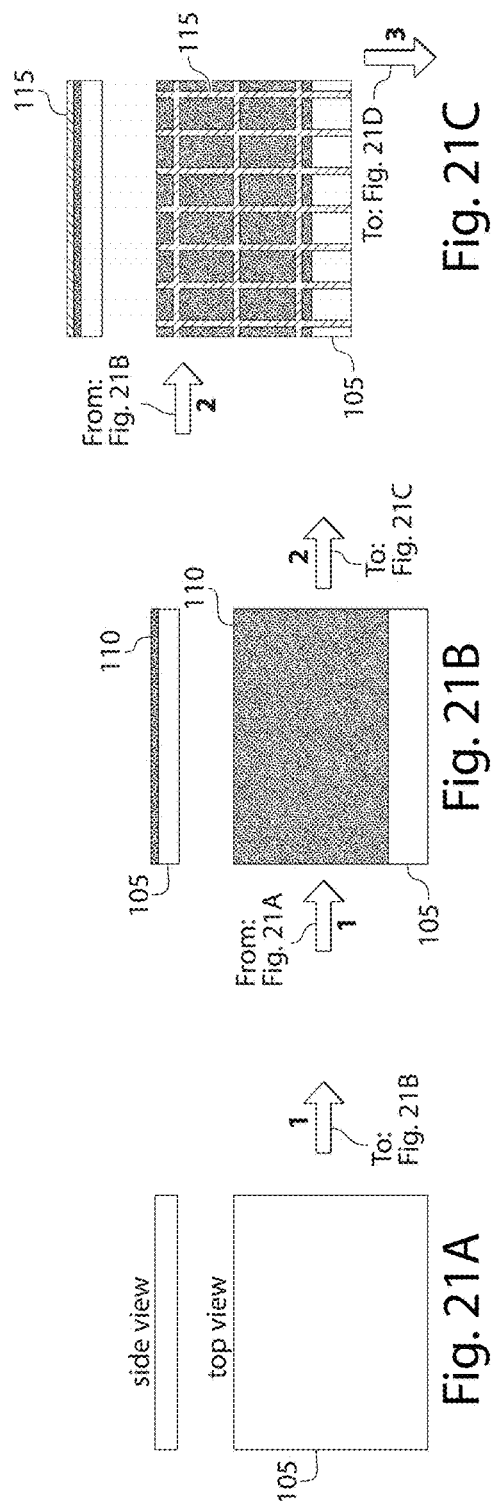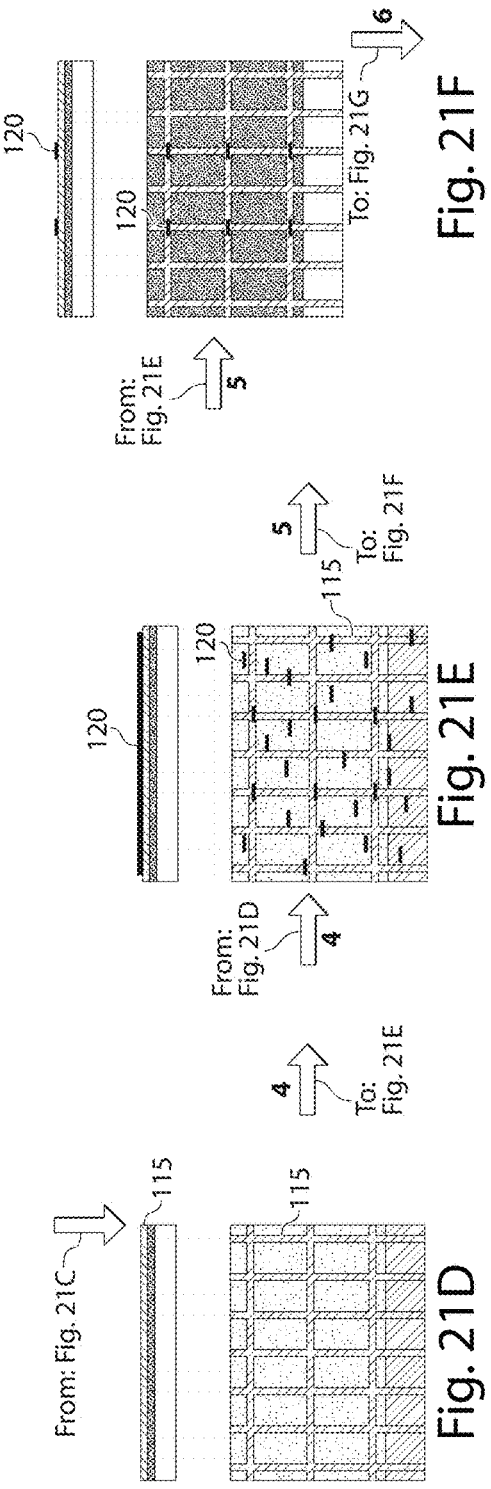

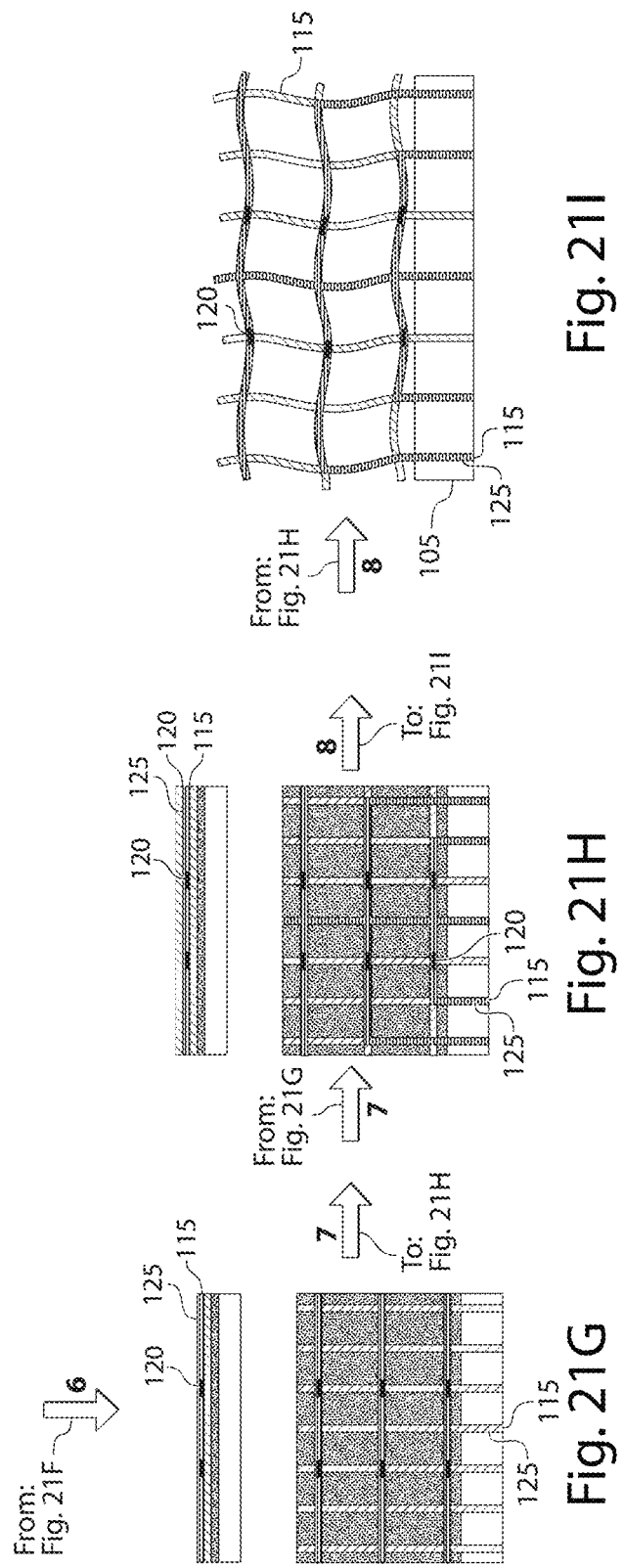

METHODS AND SYSTEMS FOR SCAFFOLDS COMPRISING NANOELECTRONIC COMPONENTS

RELATED APPLICATIONS

This application is a continuation of U.S. patent application Ser. No. 14/018,075, filed Sep. 4, 2013, entitled "Methods And Systems For Scaffolds Comprising Nanoelectronic Components," by Lieber, et al., which claims the benefit of U.S. Provisional Patent Application Ser. No. 61/698,492, filed Sep. 7, 2012, entitled "Methods And Systems For Scaffolds Comprising Nanoelectronic Components," by Lieber, et al., and of U.S. Provisional Patent Application Ser. No. 61/723,213, filed Nov. 6, 2012, entitled "Methods And Systems For Scaffolds Comprising Nanoelectronic Components," by Lieber, et al., each incorporated herein by reference in its entirety.

GOVERNMENT FUNDING

This invention was made with government support under Grant No. OD003900 awarded by the National Institutes of Health. The government has certain rights in the invention.

FIELD

The present invention generally relates to nanoscale wires and tissue engineering.

BACKGROUND

Recent efforts in coupling electronics and tissues have focused on flexible, stretchable planar arrays that conform to tissue surfaces, or implantable microfabricated probes. These approaches have been limited in merging electronics with tissues while minimizing tissue disruption, because the support structures and electronic detectors are generally of a much larger scale than the extracellular matrix and the cells. Furthermore, planar arrays only probe near the tissue surface and cannot be used to study the internal 3-dimensional structure of the tissue. For example, probes using nanowire field-effect transistors have shown that electronic devices with nanoscopic features can be used to detect extra- and intracellular potentials from single cells, but are limited to only surface recording from 3-dimensional tissues and organs. Accordingly, improvements in merging electronics with tissues are still needed.

SUMMARY

The present invention generally relates to nanoscale wires and tissue engineering. The subject matter of the present invention involves, in some cases, interrelated products, alternative solutions to a particular problem, and/or a plurality of different uses of one or more systems and/or articles.

In one aspect, the present invention is generally directed to a method. In one set of embodiments, the method includes acts of forming a polymeric material on at least a portion of a substrate, forming one or more metal leads on the polymeric material, and removing at least a portion of the sacrificial material from the polymeric material. In some cases, the substrate comprises a sacrificial material. In certain instances, the polymeric material comprises one or more nanoscale wires.

In another set of embodiments, the method includes acts of forming one or more polymeric constructs on a substrate using e-beam lithography, removing at least a portion the substrate from the one or more polymeric constructs, and rolling the one or more polymeric constructs into a 3-dimensional structure.

The method, in yet another set of embodiments, includes acts of forming one or more pre-stressed polymeric constructs on a substrate using lithography, and removing the substrate from the one or more pre-stressed polymeric constructs. In some embodiments, removal of the substrate releases stress on the pre-stressed polymeric constructs such that the polymeric constructs form a 3-dimensional structure.

In another set of embodiments, the article comprises a biological tissue comprising a semiconductor nanowire.

In some embodiments, the article comprises a tissue comprising nanoscale wires and metal leads extending between at least some of the nanoscale wires and a surface of the tissue. The article, in yet another set of embodiments, includes a biological tissue comprising at least one kinked nanoscale wire. According to still another set of embodiments, the article comprises a biological tissue comprising a curled 2-dimensional electrical network therein.

The article, in accordance with one set of embodiments, includes a biological tissue comprising a cell scaffold. In some cases, at least a portion of the cell scaffold defines at least a portion of an electrical circuit that extends externally of the cell scaffold.

According to another set of embodiments, the article includes a biological tissue comprising a cell scaffold comprising a plurality of electrical component responsive to an electrical property of the biological tissue. In another set of embodiments, the article includes a biological tissue comprising a cell scaffold comprising a plurality of pH-sensitive electrical components.

The article, in one set of embodiments, comprises a cell scaffold comprising one or more semiconductor nanowires and one or more polymeric constructs.

In another set of embodiments, the article comprises a cell scaffold comprising one or more nanoscale wires and one or more polymeric constructs. In some cases, at least one of the polymeric constructs contains a conductive pathway extending between a nanoscale wire and a surface of the cell scaffold.

According to another set of embodiments, the article comprises a cell scaffold comprising a field effect transistor and one or more polymeric constructs. In yet another set of embodiments, the article includes a cell scaffold comprising at least one kinked nanoscale wire and one or more polymeric constructs. In still another set of embodiments, the article includes a cell scaffold comprising a pH-sensitive nanoscale wire and one or more polymeric constructs. The article, in yet another set of embodiments, includes a cell scaffold comprising a sensor responsive to an electrical property and one or more polymeric constructs, wherein the sensor comprises a nanoscale wire.

In one set of embodiments, the article comprises an electrical circuit defined by one or more metal leads having a maximum cross-sectional dimension of less than about 5 micrometers, forming a 3-dimensional structure having an average pore size of between about 100 micrometers and about 1.5 mm. The electrical circuit may comprise one or more nanoscale wires in certain embodiments.

In another set of embodiments, the article comprises an electrical circuit defined by one or more metal leads, forming a 3-dimensional structure. In some cases, the electrical circuit comprises one or more pH-sensitive components.

Yet another set of embodiments is directed to an article that includes an electrical circuit defined by one or more metal leads, forming a 3-dimensional structure having an open porosity of at least about 50% and an average pore size of between about 100 micrometers and about 1.5 mm. In some instances, the electrical circuit comprises an electrical component responsive to an electrical property external to the electrical component.

In another set of embodiments, the method comprises acts of forming one or more polymers on a substrate, removing at least a portion of the substrate from the one or more polymers, and forming the polymers and metal leads into a 3-dimensional structure having an open porosity of at least about 50% and an average pore size of between about 100 micrometers and about 1.5 mm. In some cases, at least some of the polymers may comprise metal leads.

The method, in yet another set of embodiments, includes acts of forming one or more polymers on a substrate, and removing at least a portion of the substrate from the one or more polymers. In some embodiments, the one or more polymers comprise semiconductor nanowires.

Still another set of embodiments is generally directed to a method comprising depositing nanoscale wires on a polymer positioned on a substrate, and removing at least a portion of the substrate from the polymer. In yet another set of embodiments, the method includes acts of depositing one or more kinked nanoscale wires on a polymer, and forming at least a portion of the polymer into a 3-dimensional structure having an open porosity of at least about 50%.

According to one set of embodiments, the method includes an act of determining pH of a biological tissue at a resolution of less than about 1 mm. In another set of embodiments, the method includes an act of determining an electrical property of a biological tissue in three dimensions using a field effect transistor disposed within the biological tissue.

In another aspect, the present invention encompasses methods of making one or more of the embodiments described herein, for example, cell scaffolds comprising nanoscale wires. In still another aspect, the present invention encompasses methods of using one or more of the embodiments described herein, for example, cell scaffolds comprising nanoscale wires.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2 schematically illustrates a cross-section of one embodiment of the invention;

FIG. 10A-10H illustrate 3-dimensional reconstructed confocal fluorescence image of a cell scaffold and analysis of toxicity and conductance of certain cell scaffolds in accordance with various embodiments of the invention;

FIGS. 13A-13C illustrate fluorescence images of cardiomyocytes growing on a cell scaffold in accordance with one embodiment of the invention;

FIGS. 20A-20H illustrate certain techniques for forming a cell scaffold in one embodiment of the invention;

FIGS. 21A-21I illustrate certain techniques for forming a cell scaffold in one embodiment of the invention.

DETAILED DESCRIPTION

The present invention generally relates to nanoscale wires and tissue engineering. Systems and methods are provided in various embodiments for preparing cell scaffolds that can be used for growing cells or tissues, where the cell scaffolds comprise nanoscale wires. In some cases, the nanoscale wires can be connected to electronic circuits extending externally of the cell scaffold. Such cell scaffolds can be used to grow cells or tissues which can be determined and/or controlled at very high resolutions, due to the presence of the nanoscale wires, and such cell scaffolds will find use in a wide variety of novel applications, including applications in tissue engineering, prosthetics, pacemakers, implants, or the like. This approach thus allows for the creation of fundamentally new types of functionalized cells and tissues, due to the high degree of electronic control offered by the nanoscale wires and electronic circuits.

For example, certain aspects of the present invention are generally directed to cell scaffolds comprising nanoscale wires and one or more polymeric constructs. The cell scaffolds can be fabricated, for example, using well-known lithographic techniques such as those discussed herein. The cell scaffolds may also comprise metal leads that create conductive pathways between the nanoscale wires and the surface of the cell scaffold. Accordingly, the electrical properties of the nanoscale wires, and any surrounding cells or tissue grown on the cell scaffolds, can be determined and/or controlled, e.g., externally of the cell scaffolds. While others may have previously suggested using nanoscale wires in cell scaffolding materials, such applications have never involved incorporating the nanoscale wires in electronic circuits, let alone using the electronic circuits to determine or control the nanoscale wires.

Figure 1A:
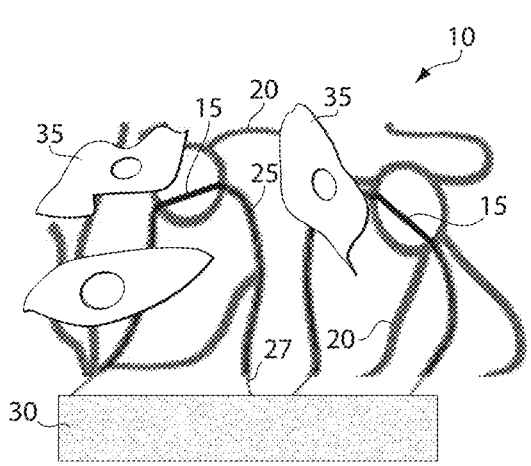
FIGS. 1A-1C illustrate certain embodiments of the invention generally directed to cell scaffolds comprising nanoscale wires.

Turning first to FIG. 1A, a representative cell scaffold is now briefly described in accordance with certain aspects of the invention. Additional details of the components forming the cell scaffold will be discussed in more detail below, including various techniques for fabricating such cell scaffolds. In FIG. 1A, cell scaffold 10 is shown comprising nanoscale wires 15 and polymeric constructs 20. The nanoscale wires may be semiconductor nanowires (e.g., comprising silicon), and the polymeric constructs can include photoresist polymers (such as SU-8), and/or biocompatible polymers (such as MATRIGEL™). Some of polymeric constructs 20 may contain conductive pathways 25 in electrical communication with some of the nanoscale wires 15, and the conductive pathways can extend externally of the surface of the cell scaffold, as is shown with conductive pathway 27. For example, some of the conductive pathways may be in electrical communication with external electrical system 30 such as a computer or a transmitter, e.g., such that physical and/or electrical properties of the nanoscale wires can be determined, and/or such that electrical stimuli can be applied to the nanoscale wires. Thus, the conductive pathways and nanoscale wires may form part of an electrical circuit in some cases. In certain embodiments, the conductive pathways can be formed out of metal leads, and in some cases dissimilar metals (e.g., chromium and palladium) can be used, e.g., to cause the cell scaffold to adopt a 3-dimensional structure. Accordingly, the cell scaffold may be constructed and arranged to have characteristics suitable for growing cells or tissues, e.g., cells 35 in FIG. 1A. For example, the cell scaffold may have an open porosity of at least about 50%, and/or an average pore size between about 100 micrometers and about 1.5 mm.

Figure 1B:
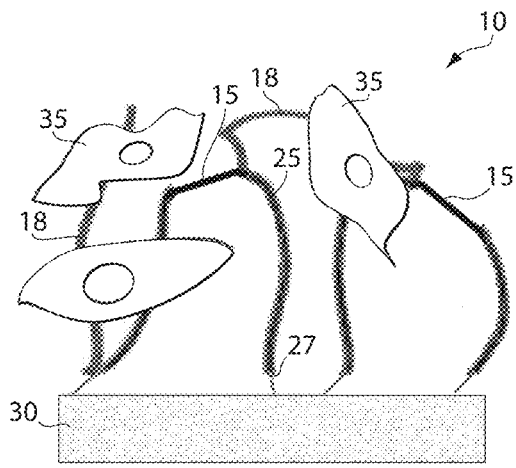

In some cases, at least a portion of the cell scaffold is formed from biodegradable materials, which can degrade over time. Thus, for example, referring now to FIG. 1B, cell scaffold 10 from FIG. 1A (containing cells 35 and being in electrical communication with external electrical system 30) may begin to degrade, eventually leaving behind nondegradable components of the cell scaffold, e.g., nondegradable polymers 18, nanoscale wires 15, conductive pathways 25, and the like, as is shown schematically in FIG. 1B. However, the nondegradable components may not necessarily be degraded, and in some cases these components can continue to function. For example, nanoscale wires 15 may be connected via conductive pathways 25 in electrical communication with external electrical system 30 such as a computer or a transmitter, even after the cell scaffold has been partially or fully degraded. Such nanoscale wires can continue to be used, e.g., to determine properties of cells or tissue, to apply electrical stimuli to cells or tissue, etc., even after partial or complete degradation of the cell scaffold.

Figure 1C:
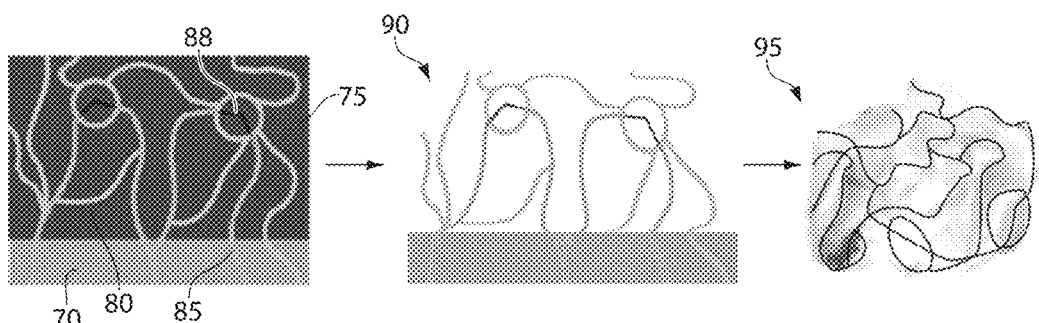

In one set of embodiments, such cell scaffolds are formed by depositing polymers and/or metals on a sacrificial material, which is then removed, as is illustrated in FIG. 1C. Briefly, on substrate 70, various polymers 80, metals 85, nanoscale wires 88, and/or other components are assembled into structure 90, at least a portion of which is present on sacrificial material 75 on substrate 70. Some or all of sacrificial material 75 can be subsequently removed to release structure 90. In some embodiments, structure 90 may then be formed into 3-dimensional structure 95 for the cell scaffold, for example, spontaneously, by folding or rolling the structure, by applying stresses to the 2-dimensional structure that cause it to adopt a 3-dimensional configuration, or the like. For instance, by pre-stressing certain components within the structure, upon removal of the sacrificial material, the structure can spontaneously form a 3-dimensional structure. In some embodiments, various materials are added to the structure (before or after removal of the sacrificial material), for example, to help stabilize the structure, to add additional agents to enhance its biocompatibility (e.g., growth hormones, extracellular matrix protein, MATRIGEL™, etc.), or the like.

The above discussion is just a brief summary of some embodiments of the present invention. However, it should be understood that other embodiments are also possible in addition to the ones described above, involving various types of materials, techniques for forming cell scaffolds, applications, and the like, which will now be discussed in greater detail.

In general, cell scaffolds are structures that cells can attach to and grow on, e.g., to form biological tissues and other biological structures. The cell scaffold may comprise biocompatible and/or biodegradable materials in some aspects of the invention, and may also contain growth factors such as growth hormones, extracellular matrix proteins, specific metabolites or nutrients, or the like. The cell scaffold typically is porous, e.g., to facilitate cell seeding therein, and/or diffusion into and out of the cell scaffold, e.g., of nutrients, waste products, etc.

The cell scaffold can also comprise one or more nanoscale wires. Non-limiting examples of suitable nanoscale wires include carbon nanotubes, nanorods, nanowires, organic and inorganic conductive and semiconducting polymers, metal nanoscale wires, semiconductor nanoscale wires (for example, formed from silicon), and the like. If carbon nanotubes are used, they may be single-walled and/or multi-walled, and may be metallic and/or semiconducting in nature. Other conductive or semiconducting elements that may not be nanoscale wires, but are of various small nanoscopic-scale dimension, also can be used within the cell scaffold.

In general, a "nanoscale wire" (also known herein as a "nanoscopic-scale wire" or "nanoscopic wire") generally is a wire or other nanoscale object, that at any point along its length, has at least one cross-sectional dimension and, in some embodiments, two orthogonal cross-sectional dimensions (e.g., a diameter) of less than 1 micrometer, less than about 500 nm, less than about 200 nm, less than about 150 nm, less than about 100 nm, less than about 70, less than about 50 nm, less than about 20 nm, less than about 10 nm, less than about 5 nm, than about 2 nm, or less than about 1 nm. In some embodiments, the nanoscale wire is generally cylindrical. In other embodiments, however, other shapes are possible; for example, the nanoscale wire can be faceted, i.e., the nanoscale wire may have a polygonal cross-section. The cross-section of a nanoscale wire can be of any arbitrary shape, including, but not limited to, circular, square, rectangular, annular, polygonal, or elliptical, and may be a regular or an irregular shape. The nanoscale wire can also be solid or hollow.

In some cases, the nanoscale wire has one dimension that is substantially longer than the other dimensions of the nanoscale wire. For example, the nanoscale wire may have a longest dimension that is at least about 1 micrometer, at least about 3 micrometers, at least about 5 micrometers, or at least about 10 micrometers or about 20 micrometers in length, and/or the nanoscale wire may have an aspect ratio (longest dimension to shortest orthogonal dimension) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

In some embodiments, a nanoscale wire are substantially uniform, or have a variation in average diameter of the nanoscale wire of less than about 30%, less than about 25%, less than about 20%, less than about 15%, less than about 10%, or less than about 5%. For example, the nanoscale wires may be grown from substantially uniform nanoclusters or particles, e.g., colloid particles. See, e.g., U.S. Pat. No. 7,301,199, issued Nov. 27, 2007, entitled "Nanoscale Wires and Related Devices," by Lieber, et al., incorporated herein by reference in its entirety. In some cases, the nanoscale wire may be one of a population of nanoscale wires having an average variation in diameter, of the population of nanowires, of less than about 30%, less than about 25%, less than about 20%, less than about 15%, less than about 10%, or less than about 5%.

In some embodiments, a nanoscale wire has a conductivity of or of similar magnitude to any semiconductor or any metal. The nanoscale wire can be formed of suitable materials, e.g., semiconductors, metals, etc., as well as any suitable combinations thereof. In some cases, the nanoscale wire will have the ability to pass electrical charge, for example, being electrically conductive. For example, the nanoscale wire may have a relatively low resistivity, e.g., less than about $10^{-3}$ Ohm m, less than about $10^{-4}$ Ohm m, less than about $10^{-6}$ Ohm m, or less than about $10^{-7}$ Ohm m. The nanoscale wire can, in some embodiments, have a conductance of at least about 1 microsiemens, at least about 3 microsiemens, at least about 10 microsiemens, at least about 30 microsiemens, or at least about 100 microsiemens.

The nanoscale wire can be solid or hollow, in various embodiments. As used herein, a "nanotube" is a nanoscale wire that is hollow, or that has a hollowed-out core, including those nanotubes known to those of ordinary skill in the art. As another example, a nanotube may be created by creating a core/shell nanowire, then etching away at least a portion of the core to leave behind a hollow shell. Accordingly, in one set of embodiments, the nanoscale wire is a non-carbon nanotube. In contrast, a "nanowire" is a nanoscale wire that is typically solid (i.e., not hollow). Thus, in one set of embodiments, the nanoscale wire may be a semiconductor nanowire, such as a silicon nanowire.

For example, in one embodiment, a nanoscale wire may comprise or consist essentially of a metal. Non-limiting examples of potentially suitable metals include aluminum, gold, silver, copper, molybdenum, tantalum, titanium, nickel, tungsten, chromium, or palladium. In another set of embodiments, a nanoscale wire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanoscale wire as the semiconductor, for example, gallium arsenide, gallium nitride, indium phosphide, cadmium selenide, etc. Still other examples include a Group II-VI material (which includes at least one member from Group II of the Periodic Table and at least one member from Group VI, for example, ZnS, ZnSe, ZnSSe, ZnCdS, CdS, or CdSe), or a Group III-V material (which includes at least one member from Group III and at least one member from Group V, for example GaAs, GaP, GaAsP, InAs, InP, AlGaAs, or InAsP).

In certain embodiments, the semiconductor can be undoped or doped (e.g., p-type or n-type). For example, in one set of embodiments, a nanoscale wire may be a p-type semiconductor nanoscale wire or an n-type semiconductor nanoscale wire, and can be used as a component of a transistor such as a field effect transistor ("FET"). For instance, the nanoscale wire may act as the "gate" of a source-gate-drain arrangement of a FET, while metal leads or other conductive pathways (as discussed herein) are used as the source and drain electrodes.

In some embodiments, a dopant or a semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, $(GaAs)_x(ZnS)_{1-x}$. Other examples of dopants may include combinations of Group IV and Group VI elemnts, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other dopant compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ and the like.

The doping of the semiconductor to produce a p-type or n-type semiconductor may be achieved via bulk-doping in certain embodiments, although in other embodiments, other doping techniques (such as ion implantation) can be used. Many such doping techniques that can be used will be familiar to those of ordinary skill in the art, including both bulk doping and surface doping techniques. A bulk-doped article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. "Heavily doped" and "lightly doped" are terms the meanings of which are clearly understood by those of ordinary skill in the art. In some embodiments, one or more regions comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions can be delta-doped or partially delta-doped.

Accordingly, in one set of embodiments, the nanoscale wires may include a heterojunction, e.g., of two regions with dissimilar materials or elements, and/or the same materials or elements but at different ratios or concentrations. The regions of the nanoscale wire may be distinct from each other with minimal cross-contamination, or the composition of the nanoscale wire can vary gradually from one region to the next. The regions may be both longitudinally arranged relative to each other, or radially arranged (e.g., as in a core/shell arrangement) on the nanoscale wire. Each region may be of any size or shape within the wire. The junctions may be, for example, a p/n junction, a p/p junction, an n/n junction, a p/i junction (where i refers to an intrinsic semiconductor), an n/i junction, an i/i junction, or the like. The junction can also be a Schottky junction in some embodiments. The junction may also be, for example, a semiconductor/semiconductor junction, a semiconductor/metal junction, a semiconductor/insulator junction, a metal/metal junction, a metal/insulator junction, an insulator/insulator junction, or the like. The junction may also be a junction of two materials, a doped semiconductor to a doped or an undoped semiconductor, or a junction between regions having different dopant concentrations. The junction can also be a defected region to a perfect single crystal, an amorphous region to a crystal, a crystal to another crystal, an amorphous region to another amorphous region, a defected region to another defected region, an amorphous region to a defected region, or the like. More than two regions may be present, and these regions may have unique compositions or may comprise the same compositions. As one example, a wire can have a first region having a first composition, a second region having a second composition, and a third region having a third composition or the same composition as the first composition. Non-limiting examples of nanoscale wires comprising heterojunctions (including core/shell heterojunctions, longitudinal heterojunctions, etc., as well as combinations thereof) are discussed in U.S. Pat. No. 7,301,199, issued Nov. 27, 2007, entitled "Nanoscale Wires and Related Devices," by Lieber, et al., incorporated herein by reference in its entirety.

In some embodiments, a nanoscale wire is a bent or a kinked nanoscale wire. A kink is typically a relatively sharp transition or turning between a first substantially straight portion of a wire and a second substantially straight portion of a wire. For example, a nanoscale wire may have 1, 2, 3, 4, or 5 or more kinks. In some cases, the nanoscale wire is formed from a single crystal and/or comprises or consists essentially of a single crystallographic orientation, for example, a <110> crystallographic orientation, a <112> crystallographic orientation, or a <11$\overline{2}$0> crystallographic orientation. It should be noted that the kinked region need not have the same crystallographic orientation as the rest of the semiconductor nanoscale wire. In some embodiments, a kink in the semiconductor nanoscale wire may be at an angle of about 120° or a multiple thereof. The kinks can be intentionally positioned along the nanoscale wire in some cases. For example, a nanoscale wire may be grown from a catalyst particle by exposing the catalyst particle to various gaseous reactants to cause the formation of one or more kinks within the nanoscale wire. Non-limiting examples of kinked nanoscale wires, and suitable techniques for making such wires, are disclosed in International Patent Application No. PCT/US2010/050199, filed Sep. 24, 2010, entitled "Bent Nanowires and Related Probing of Species," by Tian, et al., published as WO 2011/038228 on Mar. 31, 2011, incorporated herein by reference in its entirety.

In one set of embodiments, the nanoscale wire is formed from a single crystal, for example, a single crystal nanoscale wire comprising a semiconductor. A single crystal item may be formed via covalent bonding, ionic bonding, or the like, and/or combinations thereof. While such a single crystal item may include defects in the crystal in some cases, the single crystal item is distinguished from an item that includes one or more crystals, not ionically or covalently bonded, but merely in close proximity to one another.

In some embodiments, the nanoscale wires used herein are individual or free-standing nanoscale wires. For example, an "individual" or a "free-standing" nanoscale wire may, at some point in its life, not be attached to another article, for example, with another nanoscale wire, or the free-standing nanoscale wire may be in solution. This is in contrast to nanoscale features etched onto the surface of a substrate, e.g., a silicon wafer, in which the nanoscale features are never removed from the surface of the substrate as a free-standing article. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" nanoscale wire is one that can be (but need not be) removed from the location where it is made, as an individual article, and transported to a different location and combined with different components to make a functional device such as those described herein and those that would be contemplated by those of ordinary skill in the art upon reading this disclosure.

In various embodiments, more than one nanoscale wire may be present within the cell scaffold. The nanoscale wires may each independently be the same or different. For example, the cell scaffold can comprise at least 5 nanoscale wires, at least about 10 nanoscale wires, at least about 30 nanoscale wires, at least about 50 nanoscale wires, at least about 100 nanoscale wires, at least about 300 nanoscale wires, at least about 1000 nanoscale wires, etc. The nanoscale wires may be distributed uniformly or non-uniformly throughout the cell scaffold. In some cases, the nanoscale wires may be distributed at an average density of at least about 10 nanoscale wires/mm$^3$, at least about 30 nanoscale wires/mm$^3$, at least about 50 nanoscale wires/mm$^3$, at least about 75 nanoscale wires/mm$^3$, or at least about 100 nanoscale wires/mm$^3$. In certain embodiments, the nanoscale wires are distributed within the cell scaffold such that the average separation between a nanoscale wire and its nearest neighboring nanoscale wire is less than about 2 mm, less than about 1 mm, less than about 500 micrometers, less than about 300 micrometers, less than about 100 micrometers, less than about 50 micrometers, less than about 30 micrometers, or less than about 10 micrometers.

Within the cell scaffold, some or all of the nanoscale wires may be individually electronically addressable. For instance, in some cases, at least about 10%, at least about 20%, at least about 30%, at least about 40%, at least about 50%, at least about 60%, at least about 70%, at least about 80%, at least about 90%, or substantially all of the nanoscale wires within the cell scaffold may be individually electronically addressable. In some embodiments, an electrical property of a nanoscale wire can be individually determinable (e.g., being partially or fully resolvable without also including the electrical properties of other nanoscale wires), and/or such that the electrical property of a nanoscale wire may be individually controlled (e.g., by applying a desired voltage or current to the nanoscale wire, for instance, without simultaneously applying the voltage or current to other nanoscale wires). In other embodiments, however, at least some of the nanoscale wires can be controlled within the same electronic circuit (e.g., by incorporating the nanoscale wires in series and/or in parallel), such that the nanoscale wires can still be electronically controlled and/or determined.

The nanoscale wire, in some embodiments, may be responsive to a property external of the nanoscale wire, e.g., a chemical property, an electrical property, a physical property, etc. Such determination may be qualitative and/or quantitative. For example, in one set of embodiments, the nanoscale wire may be responsive to voltage. For instance, the nanoscale wire may exhibits a voltage sensitivity of at least about 5 microsiemens/V; by determining the conductivity of a nanoscale wire, the voltage surrounding the nanoscale wire may thus be determined. In other embodiments, the voltage sensitivity can be at least about 10 microsiemens/V, at least about 30 microsiemens/V, at least about 50 microsiemens/V, or at least about 100 microsiemens/V. Other examples of electrical properties that can be determined include resistance, resistivity, conductance, conductivity, impendence, or the like.

As another example, a nanoscale wire may be responsive to a chemical property of the environment surrounding the nanoscale wire. For example, an electrical property of the nanoscale wire can be affected by a chemical environment surrounding the nanoscale wire, and the electrical property can be thereby determined to determine the chemical environment surrounding the nanoscale wire. As a specific non-limiting example, the nanoscale wires may be sensitive to pH or hydrogen ions. Further non-limiting examples of such nanoscale wires are discussed in U.S. Pat. No. 7,129,554, filed Oct. 31, 2006, entitled "Nanosensors," by Lieber, et al., incorporated herein by reference in its entirety.

As an example, the nano scale wire may have the ability to bind to an analyte indicative of a chemical property of the environment surrounding the nanoscale wire (e.g., hydrogen ions for pH, or concentration for an analyte of interest), and/or the nanoscale wire may be partially or fully functionalized, i.e. comprising surface functional moieties, to which an analyte is able to bind, thereby causing a determinable property change to the nanoscale wire, e.g., a change to the resistivity or impedance of the nanoscale wire. The binding of the analyte can be specific or non-specific. Functional moieties may include simple groups, selected from the groups including, but not limited to, —OH, —CHO, —COOH, —SO$_3$H, —CN, —NH$_2$, —SH, —COSH, —COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a shell of material comprising, for example, metals, semiconductors, and insulators, which may be a metallic element, an oxide, an sulfide, a nitride, a selenide, a polymer and a polymer gel.

In some embodiments, a reaction entity may be bound to a surface of the nanoscale wire, and/or positioned in relation to the nanoscale wire such that the analyte can be determined by determining a change in a property of the nanoscale wire. The "determination" may be quantitative and/or qualitative, depending on the application. The term "reaction entity" refers to any entity that can interact with an analyte in such a manner to cause a detectable change in a property (such as an electrical property) of a nanoscale wire. The reaction entity may enhance the interaction between the nanowire and the analyte, or generate a new chemical species that has a higher affinity to the nanowire, or to enrich the analyte around the nanowire. The reaction entity can comprise a binding partner to which the analyte binds. The reaction entity, when a binding partner, can comprise a specific binding partner of the analyte. For example, the reaction entity may be a nucleic acid, an antibody, a sugar, a carbohydrate or a protein. Alternatively, the reaction entity may be a polymer, catalyst, or a quantum dot. A reaction entity that is a catalyst can catalyze a reaction involving the analyte, resulting in a product that causes a detectable change in the nanowire, e.g. via binding to an auxiliary binding partner of the product electrically coupled to the nanowire. Another exemplary reaction entity is a reactant that reacts with the analyte, producing a product that can cause a detectable change in the nanowire. The reaction entity can comprise a shell on the nanowire, e.g. a shell of a polymer that recognizes molecules in, e.g., a gaseous sample, causing a change in conductivity of the polymer which, in turn, causes a detectable change in the nanowire.

The term "binding partner" refers to a molecule that can undergo binding with a particular analyte, or "binding partner" thereof, and includes specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc.

Some or all of the nanoscale wires may be in electrical communication with a surface of the cell scaffold via one or more conductive pathways. In some embodiments, conductive pathways can be used to determine a property of a nanoscale wire (for example, an electrical property or a chemical property as is discussed herein), and/or the conductive pathway may be used to direct an electrical signal to the nanoscale wire, e.g., to electrically stimulate cells proximate the nanoscale wire. The conductive pathways can form an electrical circuit that is internally contained within the cell scaffold, and/or that extends externally of the cell scaffold, e.g., such that the electrical circuit is in electrical communication with an external electrical system, such as a computer or a transmitter (for instance, a radio transmitter, a wireless transmitter, an Internet connection, etc.). Any suitable pathway conductive pathway may be used, for example, pathways comprising metals, semiconductors, conductive polymers, or the like.

In some embodiments, more than one conductive pathway may be used within a cell scaffold. For example, multiple conductive pathways can be used such that some or all of the nanoscale wires may be individually electronically addressable within the cell scaffold. However, in other embodiments, more than one nanoscale wire may be addressable by a particular conductive pathway. In addition, in some cases, other electronic components may also be present within the cell scaffold, e.g., as part of a conductive pathway or otherwise forming part of an electrical circuit. Examples include, but are not limited to, transistors such as field effect transistors, resistors, capacitors, inductors, diodes, integrated circuits, etc. In some cases, some of these may also comprise nanoscale wires.

In addition, in some cases, the conductive pathway and/or electronic components can be at least partially surrounded by or contained within one or more polymeric constructs used to form the cell scaffold. For example, a conductive pathway, such as a metal lead, may be "sandwiched" between two polymers (which can be the same or different from each other) that form a polymeric construct of the cell scaffold. Accordingly, in some embodiments, the conductive pathway may be relatively narrow. For example, the conductive pathway may have a smallest dimension or a largest cross-sectional dimension of less than about 5 micrometers, less than about 4 micrometers, less than about 3 micrometers, less than about 2 micrometers, less than about 1 micrometer, less than about 700 nm, less than about 600 nm, less than about 500 nm, less than about 300 nm, less than about 200 nm, less than about 100 nm, less than about 80 nm, less than about 50 nm, less than about 30 nm, less than about 10 nm, less than about 5 nm, less than about 2 nm, etc. The conductive pathway may have any suitable cross-sectional shape, e.g., circular, square, rectangular, polygonal, elliptical, regular, irregular, etc. As is discussed in detail below, such conductive pathways may be achieved using lithographic or other techniques.

A given conductive pathway within a cell scaffold may be in electrical communication with any number of nanoscale wires within a cell scaffold, depending on the embodiment. For example, a conductive pathway can be in electrical communication with one, two, three, or more nanoscale wires, and if more than one nanoscale wire is used within a given conductive pathway, the nanoscale wires may each independently be the same or different. Thus, for example, an electrical property of the nanoscale wire may be determined via the conductive pathway, and/or a signal can be propagated via the conductive pathway to the nanoscale wire. In addition, as previously discussed, some or all of the nanoscale wires may be in electrical communication with a surface of the cell scaffold via one or more conductive pathways. For example, in some cases, at least about 10%, at least about 20%, at least about 30%, at least about 40%, at least about 50%, at least about 60%, at least about 70%, at least about 80%, or at least about 90% of the nanoscale wires within the cell scaffold may be in electrical communication with one or more conductive pathways, or otherwise form portions of one or more electrical circuits extending externally of the cell scaffold. In some cases, however, not all of the nanoscale wires within a cell scaffold may be in electrical communication with one or more conductive pathways, e.g., by design, or because of inefficiencies within the fabrication process, etc.

In some embodiments, one or more metal leads can be used within a conductive pathway to a nanoscale wire. The metal lead may directly physically contact the nanoscale wire and/or there may be other materials between the metal lead and the nanoscale wire that allow electrical communication to occur. Metal leads are useful due to their high conductance, e.g., such that changes within electrical properties obtained from the conductive pathway can be related to changes in properties of the nanoscale wire, rather than changes in properties of the conductive pathway. However, it is not a requirement that only metal leads be used, and in other embodiments, other types of conductive pathways may also be used, in addition or instead of metal leads.

A wide variety of metal leads can be used, in various embodiments of the invention. As non-limiting examples, the metals used within a metal lead may include aluminum, gold, silver, copper, molybdenum, tantalum, titanium, nickel, tungsten, chromium, palladium, as well as any combinations of these and/or other metals. In some cases, the metal can be chosen to be one that is readily introduced into the cell scaffold, e.g., using techniques compatible with lithographic techniques. For example, in one set of embodiments, lithographic techniques such as e-beam lithography, photolithography, X-ray lithography, extreme ultraviolet lithography, ion projection lithography, etc. may be used to layer or deposit one or more metals on a substrate. Additional processing steps can also be used to define or register the metal leads in some cases. Thus, for example, the thickness of a metal layer may be less than about 5 micrometers, less than about 4 micrometers, less than about 3 micrometers, less than about 2 micrometers, less than about 1 micrometer, less than about 700 nm, less than about 600 nm, less than about 500 nm, less than about 300 nm, less than about 200 nm, less than about 100 nm, less than about 80 nm, less than about 50 nm, less than about 30 nm, less than about 10 nm, less than about 5 nm, less than about 2 nm, etc. The thickness of the layer may also be at least about 10 nm, at least about 20 nm, at least about 40 nm, at least about 60 nm, at least about 80 nm, or at least about 100 nm. For example, the thickness of a layer may be between about 40 nm and about 100 nm, between about 50 nm and about 80 nm.

In some embodiments, more than one metal can be used within a metal lead. For example, two, three, or more metals may be used within a metal lead. The metals may be deposited in different regions or alloyed together, or in some cases, the metals may be layered on top of each other, e.g., layered on top of each other using various lithographic techniques. For example, a second metal may be deposited on a first metal, and in some cases, a third metal may be deposited on the second metal, etc. Additional layers of metal (e.g., fourth, fifth, sixth, etc.) may also be used in some embodiments. The metals can all be different, or in some cases, some of the metals (e.g., the first and third metals) may be the same. Each layer may independently be of any suitable thickness or dimension, e.g., of the dimensions described above, and the thicknesses of the various layers can independently be the same or different.

If dissimilar metals are layered on top of each other, they may be layered in some embodiments in a "stressed" configuration (although in other embodiments they may not necessarily be stressed). As a specific non-limiting example, chromium and palladium can be layered together to cause stresses in the metal leads to occur, thereby causing warping or bending of the metal leads. The amount and type of stress may also be controlled, e.g., by controlling the thicknesses of the layers. For example, relatively thinner layers can be used to increase the amount of warping that occurs.

Without wishing to be bound by any theory, it is believed that layering metals having a difference in stress (e.g., film stress) with respect to each other may, in some cases, cause stresses within the metal, which can cause bending or warping as the metals seek to relieve the stresses. In some embodiments, such mismatches are undesirable because they could cause warping of the metal leads and thus, the cell scaffold. However, in other embodiments, such mismatches may be desired, e.g., so that the cell scaffold can be intentionally deformed to form a 3-dimensional structure, as discussed below. In addition, in certain embodiments, the deposition of mismatched metals within a lead may occur at specific locations within the cell scaffold, e.g., to cause specific warpings to occur, which can be used to cause the cell scaffold to be deformed into a particular shape or configuration. For example, a "line" of such mismatches can be used to cause an intentional bending or folding along the line of the cell scaffold.

In one set of embodiments, the cell scaffold may also contain one or more polymeric constructs. The polymeric constructs typically comprise one or more polymers, e.g., photoresists, biocompatible polymers, biodegradable polymers, etc., and optionally may contain other materials, for example, metal leads or other conductive pathway materials. The polymeric constructs may be separately formed then assembled into a cell scaffold, and/or the polymeric constructs may be integrally formed as part of the cell scaffold, for example, by forming or manipulating (e.g. folding, rolling, etc.) the polymeric constructs into a 3-dimensional structure that defines the cell scaffold.

Figure 4A:
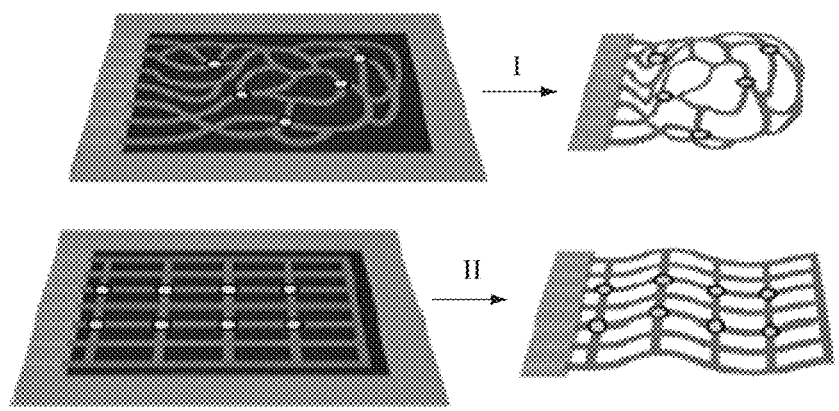
FIGS. 4A-4I illustrate cell scaffolds comprising nanoscale wires, in accordance with certain embodiments of the invention.

In one set of embodiments, some or all of the polymeric constructs have the form of fibers or ribbons. For example, the polymeric constructs may have one dimension that is substantially longer than the other dimensions of the polymeric construct. The fibers can in some cases be joined together to form a "network" or "mesh" of fibers that define the cell scaffold. For example, referring to FIG. 4A, Panel II, a cell scaffold may contain a plurality of fibers that are orthogonally arranged to form a regular network of polymeric constructs. However, the polymeric constructs need not be regularly arranged, as is shown in FIG. 4A, Panel I, with a more irregular arrangement of polymer constructs. In addition, it should be noted that although FIG. 4A shows only polymer constructs having the form of fibers, this is by way of example only, and in other embodiments, other shapes of polymeric constructs can be used. In general, any shape or dimension of polymeric construct that allows for cell growth may be used.

Thus, for example, in one set of embodiments, some or all of the polymeric constructs have a smallest dimension or a largest cross-sectional dimension of less than about 5 micrometers, less than about 4 micrometers, less than about 3 micrometers, less than about 2 micrometers, less than about 1 micrometer, less than about 700 nm, less than about 600 nm, less than about 500 nm, less than about 300 nm, less than about 200 nm, less than about 100 nm, less than about 80 nm, less than about 50 nm, less than about 30 nm, less than about 10 nm, less than about 5 nm, less than about 2 nm, etc. A polymeric construct may also have any suitable cross-sectional shape, e.g., circular, square, rectangular, polygonal, elliptical, regular, irregular, etc. Examples of methods of forming polymeric constructs, e.g., by lithographic or other techniques, are discussed below.

In one set of embodiment, the polymeric constructs can be arranged such that the cell scaffold has dimensions that facilitate cell seeding therein, and/or diffusion into and out of the cell scaffold, e.g., of nutrients, waste products, etc. For example, in some cases, the polymeric constructs may be constructed and arranged within the cell scaffold such that the cell scaffold has an open porosity of at least about 30%, at least about 40%, at least about 50%, at least about 60%, at least about 70%, at least about 75%, at least about 80%, at least about 85%, at least about 90%, at least about 95%, at least about 97, at least about 99%, at least about 99.5%, or at least about 99.8%. The "open porosity" is generally described as the volume of empty space within the cell scaffold divided by the overall volume defined by the cell scaffold, and can be thought of as being equivalent to void volume. Typically, the open porosity includes the volume within the cell scaffold to which cells can access. In some cases, the cell scaffold does not contain significant amounts of internal volume to which the cells are incapable of addressing, e.g., due to lack of access and/or pore access being too small.

In some cases, a "two-dimensional open porosity" may also be defined, e.g., of a cell scaffold that is subsequently formed or manipulated into a 3-dimensional structure. The two-dimensional open porosities of a cell scaffold can be defined as the void area within the two-dimensional configuration of the cell scaffold (e.g., where no material is present) divided by the overall area of cell scaffold, and can be determined before or after the cell scaffold has been formed into a 3-dimensional structure. Depending on the application, a cell scaffold may have a two-dimensional open porosity of at least about 30%, at least about 40%, at least about 50%, at least about 60%, at least about 70%, at least about 75%, at least about 80%, at least about 85%, at least about 90%, at least about 95%, at least about 97, at least about 99%, at least about 99.5%, or at least about 99.8%, etc.

Another method of generally determining the two-dimensional porosity of the cell scaffold is by determining the areal mass density, i.e., the mass of the cell scaffold divided by the area of one face of the cell scaffold (including holes or voids present therein). Thus, for example, in another set of embodiments, the cell scaffold may have an areal mass density of less than about 100 micrograms/cm$^2$, less than about 80 micrograms/cm$^2$, less than about 60 micrograms/cm$^2$, less than about 50 micrograms/cm$^2$, less than about 40 micrograms/cm$^2$, less than about 30 micrograms/cm$^2$, or less than about 20 micrograms/cm$^2$.

The porosity of a cell scaffold can be defined by one or more pores. Pores that are too small can hinder or restrict cell access. Thus, in one set of embodiments, the cell scaffold may have an average pore size of at least about 100 micrometers, at least about 200 micrometers, at least about 300 micrometers, at least about 400 micrometers, at least about 500 micrometers, at least about 600 micrometers, at least about 700 micrometers, at least about 800 micrometers, at least about 900 micrometers, or at least about 1 mm. However, in other embodiments, pores that are too big may prevent cells from being able to satisfactorily use or even access the pore volume. Thus, in some cases, the cell scaffold may have an average pore size of no more than about 1.5 mm, no more than about 1.4 mm, no more than about 1.3 mm, no more than about 1.2 mm, no more than about 1.1 mm, no more than about 1 mm, no more than about 900 micrometers, no more than about 800 micrometers, no more than about 700 micrometers, no more than about 600 micrometers, or no more than about 500 micrometers. Combinations of these are also possible, e.g., in one embodiment, the average pore size is at least about 100 micrometers and no more than about 1.5 mm. In addition, larger or smaller pores than these can also be used in a cell scaffold in certain cases. Pore sizes may be determined using any suitable technique, e.g., through visual inspection, BET measurements, or the like.

In various embodiments, one or more of the polymers forming a polymeric construct may be a photoresist. While not commonly used in cell scaffolds, photoresists are typically used in lithographic techniques, which can be used as discussed herein to form the polymeric construct. For example, the photoresist may be chosen for its ability to react to light to become substantially insoluble (or substantially soluble, in some cases) to a photoresist developer. For instance, photoresists that can be used within a polymeric construct include, but are not limited to, SU-8, S1805, LOR 3A, poly(methyl methacrylate), poly(methyl glutarimide), phenol formaldehyde resin (diazonaphthoquinone/novolac), diazonaphthoquinone (DNQ), Hoechst AZ 4620, Hoechst AZ 4562, Shipley 1400-17, Shipley 1400-27, Shipley 1400-37, or the like. These and many other photoresists are available commercially.

A polymeric construct may also contain one or more polymers that are biocompatible and/or biodegradable, in certain embodiments. A polymer can be biocompatible, biodegradable, or both biocompatible and biodegradable, and in some cases, the degree of biodegradation or biocompatibility depends on the physiological environment to which the polymer is exposed to.

Typically, a biocompatible material is one that does not illicit an immune response, or elicits a relatively low immune response, e.g., one that does not impair the cell scaffold or the cells therein from continuing to function for its intended use. In some embodiments, the biocompatible material is able to perform its desired function without eliciting any undesirable local or systemic effects in the subject. In some cases, the material can be incorporated into tissues within the subject, e.g., without eliciting any undesirable local or systemic effects, or such that any biological response by the subject does not substantially affect the ability of the material from continuing to function for its intended use. For example, in a cell scaffold, the cell scaffold may be able to support appropriate cellular or tissue activity when implanted within a subject, e.g., including the facilitation of molecular and/or mechanical signaling systems, without substantially eliciting undesirable effects in those cells, or undesirable local or systemic responses, or without eliciting a response that causes the cell scaffold to cease functioning for its intended use. Examples of techniques for determining biocompatibility include, but are not limited to, the ISO 10993 series of for evaluating the biocompatibility of medical devices. As another example, a biocompatible material may be implanted in a subject for an extended period of time, e.g., at least about a month, at least about 6 months, or at least about a year, and the integrity of the material, or the immune response to the material, may be determined. For example, a suitably biocompatible material may be one in which the immune response is minimal, e.g., one that does not substantially harm the health of the subject. One example of a biocompatible material is poly(methyl methacrylate). In some embodiments, a biocompatible material may be used to cover or shield a non-biocompatible material (or a poorly biocompatible material) from the cells or tissue, for example, by covering the material.

A biodegradable material typically degrades over time when exposed to a biological system, e.g., through oxidation, hydrolysis, enzymatic attack, phagocytosis, or the like. For example, a biodegradable material can degrade over time when exposed to water (e.g., hydrolysis) or enzymes. In some cases, a biodegradable material is one that exhibits degradation (e.g., loss of mass and/or structure) when exposed to physiological conditions for at least about a month, at least about 6 months, or at least about a year. For example, the biodegradable material may exhibit a loss of mass of at least about 10%, at least about 20%, at least about 30%, at least about 40%, at least about 50%, at least about 60%, at least about 70%, at least about 80%, or at least about 90%. In certain cases, some or all of the degradation products may be resorbed or metabolized, e.g., into cells or tissues. For example, certain biodegradable materials, during degradation, release substances that can be metabolized by cells or tissues. For instance, polylactic acid releases water and lactic acid during degradation.

Examples of such biocompatible and/or biodegradable polymers include, but are not limited to, poly(lactic-co-glycolic acid), polylactic acid, polyglycolic acid, poly(methyl methacrylate), poly(trimethylene carbonate), collagen, fibrin, polysaccharidic materials such as chitosan or glycosaminoglycans, hyaluronic acid, polycaprolactone, and the like.

The polymers and other components forming the cell scaffold can also be used in some embodiments to provide a certain degree of flexibility to the cell scaffold, which can be quantified as a bending stiffness per unit width of polymer construct. An example method for determining the bending stiffness is discussed below. In various embodiments, the cell scaffold may have a bending stiffness of less than about 5 nN m, less than about 4.5 nN m, less than about 4 nN m, less than about 3.5 nN m, less than about 3 nN m, less than about 2.5 nN m, less than about 2 nN m, less than about 1.5 nN m, or less than about 1 nN m.

In some embodiments of the invention, the cell scaffold may also contain other materials in addition to the photoresists or biocompatible and/or biodegradable polymers described above. Non-limiting examples include other polymers, growth hormones, extracellular matrix protein, specific metabolites or nutrients, or the like. For example, in one of embodiments, one or more agents able to promote cell growth can be added to the cell scaffold, e.g., hormones such as growth hormones, extracellular matrix protein, pharmaceutical agents, vitamins, or the like. Many such growth hormones are commercially available, and may be readily selected by those of ordinary skill in the art based on the specific type of cell or tissue used or desired. Similarly, non-limiting examples of extracellular matrix proteins include gelatin, laminin, fibronectin, heparan sulfate, proteoglycans, entactin, hyaluronic acid, collagen, elastin, chondroitin sulfate, keratan sulfate, MATRIGEL™, or the like. Many such extracellular matrix proteins are available commercially, and also can be readily identified by those of ordinary skill in the art based on the specific type of cell or tissue used or desired.

As another example, in one set of embodiments, additional scaffold materials can be added to the cell scaffold, e.g., to control the size of pores within the cell scaffold, to promote cell adhesion or growth within the cell scaffold, to increase the structural stability of the cell scaffold, to control the flexibility of the cell scaffold, etc. For instance, in one set of embodiments, additional fibers or other suitable polymers may be added to the cell scaffold, e.g., electrospun fibers can be used as a secondary scaffold. The additional scaffold materials can be formed from any of the materials described herein in reference to cell scaffolds, e.g., photoresists or biocompatible and/or biodegradable polymers, or other polymers described herein. As another non-limiting example, a glue such as a silicone elastomer glue can be used to control the shape of the cell scaffold.

In some cases, the cell scaffold can include a 2-dimensional structure that is formed into a final 3-dimensional structure, e.g., by folding or rolling the structure. It should be understood that although the 2-dimensional structure can be described as having an overall length, width, and height, the overall length and width of the structure may each be substantially greater than the overall height of the structure. The 2-dimensional structure may also be manipulated to have a different shape that is 3-dimensional, e.g., having an overall length, width, and height where the overall length and width of the structure are not each substantially greater than the overall height of the structure. For instance, the structure may be manipulated to increase the overall height of the material, relative to its overall length and/or width, for example, by folding or rolling the structure. Thus, for example, a relatively planar sheet of material (having a length and width much greater than its thickness) may be rolled up into a "tube," such that the tube has an overall length, width, and height of relatively comparable dimensions).

Thus, for example, the 2-dimensional structure may comprise one or more nanoscale wires and one or more polymeric constructs formed into a 2-dimensional structure or network that is subsequently formed into a 3-dimensional structure. In some embodiments, the 2-dimensional structure may be rolled or curled up to form the 3-dimensional structure, or the 2-dimensional structure may be folded or creased one or more times to form the 3-dimensional structure. Such manipulations can be regular or irregular. In certain embodiments, as discussed herein, the manipulations are caused by pre-stressing the 2-dimensional structure such that it spontaneously forms the 3-dimensional structure, although in other embodiments, such manipulations can be performed separately, e.g., after formation of the 2-dimensional structure.

Cell scaffolds such as those described above can be used in a wide variety of applications, for example, for tissue engineering, prosthetics, pacemakers, implants, blood or other vessels, and the like. Accordingly, virtually any kind of cell that can be grown on a cell scaffold can be used, in various embodiments of the invention, grown to form a tissue on the cell scaffold. In some cases, the cells may be ones that are electrically active, e.g., having electrical properties which can be determined and/or controlled. Cells that are electrically active include, but are not limited to, nerve cells or neurons, muscle cells, cardiac cells, or the like. However, in other cases, the cells do not necessarily have to be electrically active. For example, in one set of embodiments, chemical properties (such as pH) can be determined using nanoscale wires, etc. that are contained within the cell scaffold, and the cells and/or tissues within the cell scaffold accordingly need not be electrically active (although they can be).

In one set of embodiments, a cell scaffold may not be present within a biological tissue (e.g., an implanted tissue), or may have been present but may have partially or completely degraded, e.g., such that it no longer functions as a cell scaffold. Thus, for example, in one embodiment, the present invention is directed to a biological tissue comprising nanoscale wires such as semiconductor nanowires or any other nanoscale wire describe herein. In some cases, at least some of the nanoscale wires form a portion of an electrical circuit that extends externally of the tissue. The biological tissue may also comprise conductive pathways, such metal leads, within the biological tissue, e.g., connecting nanoscale wires or other electrical components. In addition, in some cases, some or all of the conductive pathways can also be connected to an external electrical system, such as a computer or a transmitter, e.g., a radio transmitter, a wireless transmitter, etc. Thus, in another set of embodiments, the present invention is generally directed to a biological tissue comprising nanoscale wires and/or conductive pathways (e.g., forming an electrical network such as is discussed herein), not necessarily limited to a cell scaffold. The tissue may be present in vitro or an in vivo, e.g., implanted into a subject, such as a human subject, the tissues may be autologous, homologous, or heterologous with the subject.

In some embodiments, cells or tissues can be interfaced with the nanoscale wires or other electrical components (within the cell scaffold, and/or after degradation of the cell scaffold) to such a degree that they form a substantially unitary structure where cells present within the biological tissue may require electrically communications with the nanoscale wires in order to function, or to communicate with each other. For example, cardiac or muscle cells within a tissue may not be able to beat or contract, or may not be able to beat or contract in a regular fashion, without stimuli from the nanoscale wires, or without using the nanoscale wires to communicate. As another example, nerve cells within the tissue may form axons and/or dendrites with the nanoscale wires, e.g., in order to transmit and/or receive electronic signals from other nerve cells and/or from the nanoscale wires. In such fashion, an electrically unitary structure may be generated, i.e., a "cyborg" tissue can be created whose biological functioning depends not only on the cells or tissues, but on the electronic components as well, e.g., such that the distinction between the biological and electronic systems becomes blurred.

In another set of embodiments, the biological tissue may be one that contains sufficient nanoscale wires that a property, such as a chemical or an electrical property, can be determined at a relatively high resolution, and/or in three dimensions within the biological tissue, e.g., due to the placement of nanoscale wires within the tissue that can be used as sensors. For example, one or more nanoscale wires may be present within an electronic circuit as a component of a field effect transistor. In addition, in certain embodiments, such determinations may be transmitted and/or recorded, e.g., for later use and or analysis.

Thus, for example, a property such as a chemical property and/or an electrical property can be determined at a resolution of less than about 2 mm, less than about 1 mm, less than about 500 micrometers, less than about 300 micrometers, less than about 100 micrometers, less than about 50 micrometers, less than about 30 micrometers, or less than about 10 micrometers, etc., e.g., due to the average separation between a nanoscale wire and its nearest neighboring nanoscale wire. In addition, as mentioned, the property may be determined within the tissue in 3 dimensions in some instances, in contrast with many other techniques where only a surface of the biological tissue can be studied. Accordingly, very high resolution and/or 3-dimensional mappings of the property of the biological tissue can be obtained in some embodiments. Any suitable tissue may be studied, e.g., cardiac tissue, vascular tissue, muscle, cartilage, bone, liver tissue, pancreatic tissue, bladder tissue, airway tissues, bone marrow tissue, or the like.

In addition, in some cases, such properties can be determined and/or recorded as a function of time. Thus, for example, such properties can be determined at a time resolution of less than about 1 min, less than about 30 s, less than about 15 s, less than about 10 s, less than about 5 s, less than about 3 s, less than about 1 s, less than about 500 ms, less than about 300 ms, less than about 100 ms, less than about 50 ms, less than about 30 ms, less than about 10 ms, less than about 5 ms, less than about 3 ms, less than about 1 ms, etc.

In yet another set of embodiments, the biological tissue, and/or portions of the biological tissue, may be electrically stimulated using nanoscale wires present within the tissue. For example, all, or a subset of the electrically active nanoscale wires may be electrically stimulated, e.g., by using an external electrical system, such as a computer. Thus, for example, a single nanoscale wire, a group of nanoscale wires, or substantially all of the nanoscale wires can be electrically stimulated, depending on the particular application. In some cases, such nanoscale wires can be stimulated in a particular pattern, e.g., to cause cardiac or muscle cells to contract or beat in a particular pattern (for example, as part of a prosthetic or a pacemaker), to cause the firing of neurons with a particular pattern, to monitor the status of an implanted tissue within a subject, or the like.

Another aspect of the present invention is generally directed to systems and methods for making and using such cell scaffolds. Briefly, in one set of embodiments, a scaffold is constructed by assembling various polymers, metals, nanoscale wires, and other components together on a substrate. For example, lithographic techniques such as e-beam lithography, photolithography, X-ray lithography, extreme ultraviolet lithography, ion projection lithography, etc. may be used to pattern polymers, metals, etc. on the substrate, and nanoscale wires can be prepared separately then added to the substrate. After assembly, at least a portion of the substrate (e.g., a sacrificial material) may be removed, allowing the scaffold to be partially or completely removed from the substrate. The scaffold can, in some cases, be formed into a 3-dimensional structure, for example, spontaneously, or by folding or rolling the structure. Other materials may also be added to the scaffold, e.g., to help stabilize the structure, to add additional agents to enhance its biocompatibility, etc. The scaffold can be used in vivo, e.g., by implanting it in a subject, and/or in vitro, e.g., by seeding cells, etc. on the scaffold. In addition, in some cases, cells may initially be grown on the scaffold before the scaffold is implanted into a subject. A schematic diagram of the layers formed on the substrate in one embodiment is shown in FIG. 2. However, it should be understood that this diagram is illustrative only and is not drawn to scale, and not all of the layers shown in FIG. 2 are necessarily required in every embodiment of the invention.

The substrate (200 in FIG. 2) may be chosen to be one that can be used for lithographic techniques such as e-beam lithography or photolithography, or other lithographic techniques including those discussed herein. For example, the substrate may comprise or consist essentially of a semiconductor material such as silicon, although other substrate materials (e.g., a metal) can also be used. Typically, the substrate is one that is substantially planar, e.g., so that polymers, metals, and the like can be patterned on the substrate.

In some cases, a portion of the substrate can be oxidized, e.g., forming $SiO_2$ and/or $Si_3N_4$ on a portion of the substrate, which may facilitate subsequent addition of materials (metals, polymers, etc.) to the substrate. In some cases, the oxidized portion may form a layer of material on the substrate (205 in FIG. 2), e.g., having a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc.

In certain embodiments, one or more polymers can also be deposited or otherwise formed prior to depositing the sacrificial material. In some cases, the polymers may be deposited or otherwise formed as a layer of material (210 in FIG. 2) on the substrate. Deposition may be performed using any suitable technique, e.g., using lithographic techniques such as e-beam lithography, photolithography, X-ray lithography, extreme ultraviolet lithography, ion projection lithography, etc. In some cases, some or all of the polymers may be biocompatible and/or biodegradable. The polymers that are deposited may also comprise methyl methacrylate and/or poly(methyl methacrylate), in some embodiments. One, two, or more layers of polymer can be deposited (e.g., sequentially) in various embodiments, and each layer may independently have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc.

Next, a sacrificial material may be deposited. The sacrificial material can be chosen to be one that can be removed without substantially altering other materials (e.g., polymers, other metals, nanoscale wires, etc.) deposited thereon. For example, in one embodiment, the sacrificial material may be a metal, e.g., one that is easily etchable. For instance, the sacrificial material can comprise germanium or nickel, which can be etched or otherwise removed, for example, using a peroxide (e.g., $H_2O_2$) or a nickel etchant (many of which are readily available commercially). In some cases, the sacrificial material may be deposited on oxidized portions or polymers previously deposited on the substrate. In some cases, the sacrificial material is deposited as a layer (e.g., 215 in FIG. 2). The layer can have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc.

In some embodiments, a "bedding" polymer can be deposited, e.g., on the sacrificial material. The bedding polymer may include one or more polymers, which may be deposited as one or more layers (220 in FIG. 2). The bedding polymer can be used to support the nanoscale wires, and in some cases, partially or completely surround the nanoscale wires, depending on the application. For example, as discussed below, one or more nanoscale wires may be deposited on at least a portion of the uppermost layer of bedding polymer.

For instance, the bedding polymer can at least partially define a cell scaffold. In one set of embodiments, the bedding polymer may be deposited as a layer of material, such that portions of the bedding polymer may be subsequently removed. For example, the bedding polymer can be deposited using lithographic techniques such as e-beam lithography, photolithography, X-ray lithography, extreme ultraviolet lithography, ion projection lithography, etc., or using other techniques for removing polymer that are known to those of ordinary skill in the art. In some cases, more than one bedding polymer is used, e.g., deposited as more than one layer (e.g., sequentially), and each layer may independently have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc. For example, in some embodiments, portions of the photoresist may be exposed to light (visible, UV, etc.), electrons, ions, X-rays, etc. (e.g., projected onto the photoresist), and the exposed portions can be etched away (e.g., using suitable etchants, plasma, etc.) to produce the pattern.

Accordingly, the bedding polymer may be formed into a particular pattern, e.g., in a grid, or in a pattern that suggests an endogenous cell scaffold, before or after deposition of nanoscale wires (as discussed in detail below), in certain embodiments of the invention. The pattern can be regular or irregular. For example, the bedding polymer can be formed into a pattern defining pore sizes such as those discussed herein. For instance, the polymer may have an average pore size of at least about 100 micrometers, at least about 200 micrometers, at least about 300 micrometers, at least about 400 micrometers, at least about 500 micrometers, at least about 600 micrometers, at least about 700 micrometers, at least about 800 micrometers, at least about 900 micrometers, or at least about 1 mm, and/or an average pore size of no more than about 1.5 mm, no more than about 1.4 mm, no more than about 1.3 mm, no more than about 1.2 mm, no more than about 1.1 mm, no more than about 1 mm, no more than about 900 micrometers, no more than about 800 micrometers, no more than about 700 micrometers, no more than about 600 micrometers, or no more than about 500 micrometers, etc.

Any suitable polymer may be used as the bedding polymer. In some cases, one or more of the polymers can be chosen to be biocompatible and/or biodegradable. In certain embodiments, one or more of the bedding polymers may comprise a photoresist. Photoresists can be useful due to their familiarity in use in lithographic techniques such as those discussed herein. Non-limiting examples of photoresists include SU-8, S1805, LOR 3A, poly(methyl methacrylate), poly(methyl glutarimide), phenol formaldehyde resin (diazonaphthoquinone/novolac), diazonaphthoquinone (DNQ), Hoechst AZ 4620, Hoechst AZ 4562, Shipley 1400-17, Shipley 1400-27, Shipley 1400-37, etc., as well as any others discussed herein.

In certain embodiments, one or more of the bedding polymers can be heated or baked, e.g., before or after depositing nanoscale wires thereon as discussed below, and/or before or after patterning the bedding polymer. For example, such heating or baking, in some cases, is important to prepare the polymer for lithographic patterning. In various embodiments, the bedding polymer may be heated to a temperature of at least about 30° C., at least about 65° C., at least about 95° C., at least about 150° C., or at least about 180° C., etc.

Next, one or more nanoscale wires (e.g., 225 in FIG. 2) may be deposited, e.g., on a bedding polymer on the substrate. Any of the nanoscale wires described herein may be used, e.g., n-type and/or p-type nanoscale wires, substantially uniform nanoscale wires (e.g., having a variation in average diameter of less than 20%), nanoscale wires having a diameter of less than about 1 micrometer, semiconductor nanowires, silicon nanowires, bent nanoscale wires, kinked nanoscale wires, core/shell nanowires, nanoscale wires with heterojunctions, etc. In some cases, the nanoscale wires are present in a liquid which is applied to the substrate, e.g., poured, painted, or otherwise deposited thereon. In some embodiments, the liquid is chosen to be relatively volatile, such that some or all of the liquid can be removed by allowing it to substantially evaporate, thereby depositing the nanoscale wires. In some cases, at least a portion of the liquid can be dried off, e.g., by applying heat to the liquid. Examples of suitable liquids include water or isopropanol.

In some cases, at least some of the nanoscale wires may be at least partially aligned, e.g., as part of the deposition process, and/or after the nanoscale wires have been deposited on the substrate. Thus, the alignment can occur before or after drying or other removal of the liquid, if a liquid is used. Any suitable technique may be used for alignment of the nanoscale wires. For example, the nanoscale wires can be aligned by passing or sliding substrates containing the nanoscale wires past each other (see, e.g., International Patent Application No. PCT/US2007/008540, filed Apr. 6, 2007, entitled "Nanoscale Wire Methods and Devices," by Nam, et al., published as WO 2007/145701 on Dec. 21, 2007, incorporated herein by reference in its entirety), the nanoscale wires can be aligned using Langmuir-Blodgett techniques (see, e.g., U.S. patent application Ser. No. 10/995,075, filed Nov. 22, 2004, entitled "Nanoscale Arrays and Related Devices," by Whang, et al., published as U.S. Patent Application Publication No. 2005/0253137 on Nov. 17, 2005, incorporated herein by reference in its entirety), the nanoscale wires can be aligned by incorporating the nanoscale wires in a liquid film or "bubble" which is deposited on the substrate (see, e.g., U.S. patent application Ser. No. 12/311,667, filed Apr. 8, 2009, entitled "Liquid Films Containing Nanostructured Materials," by Lieber, et al., published as U.S. Patent Application Publication No. 2010/0143582 on Jun. 10, 2010, incorporated by reference herein in its entirety), or a gas or liquid can be passed across the nanoscale wires to align the nanoscale wires (see, e.g., U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; and U.S. Pat. No. 7,301,199, issued Nov. 27, 2007, entitled "Nanoscale Wires and Related Devices," by Lieber, et al., each incorporated herein by reference in its entirety). Combinations of these and/or other techniques can also be used in certain instances. In some cases, the gas may comprise an inert gas and/or a noble gas, such as nitrogen or argon.

In certain embodiments, a "lead" polymer is deposited (230 in FIG. 2), e.g., on the sacrificial material and/or on at least some of the nanoscale wires. The lead polymer may include one or more polymers, which may be deposited as one or more layers. The lead polymer can be used to cover or protect metal leads or other conductive pathways, which may be subsequently deposited on the lead polymer. In some embodiments, the lead polymer can be deposited, e.g., as a layer of material such that portions of the lead polymer can be subsequently removed, for instance, using lithographic techniques such as e-beam lithography, photolithography, X-ray lithography, extreme ultraviolet lithography, ion projection lithography, etc., or using other techniques for removing polymer that are known to those of ordinary skill in the art, similar to the bedding polymers previously discussed. However, the lead polymers need not be the same as the bedding polymers (although they can be), and they need not be deposited using the same techniques (although they can be). In some cases, more than one lead polymer may be used, e.g., deposited as more than one layer (for example, sequentially), and each layer may independently have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc.

Any suitable polymer can be used as the lead polymer. In some cases, one or more of the polymers may be chosen to be biocompatible and/or biodegradable. For example, in one set of embodiments, one or more of the polymers may comprise poly(methyl methacrylate). In certain embodiments, one or more of the lead polymers comprises a photoresist, such as those described herein.

In certain embodiments, one or more of the lead polymers may be heated or baked, e.g., before or after depositing nanoscale wires thereon as discussed below, and/or before or after patterning the lead polymer. For example, such heating or baking, in some cases, is important to prepare the polymer for lithographic patterning. In various embodiments, the lead polymer may be heated to a temperature of at least about 30° C., at least about 65° C., at least about 95° C., at least about 150° C., or at least about 180° C., etc.

Next, a metal or other conductive material can be deposited (235 in FIG. 2), e.g., on one or more of the lead polymer, the sacrificial material, the nanoscale wires, etc. to form a metal lead or other conductive pathway. More than one metal can be used, which may be deposited as one or more layers. For example, a first metal may be deposited, e.g., on one or more of the lead polymers, and a second metal may be deposited on at least a portion of the first metal. Optionally, more metals can be used, e.g., a third metal may be deposited on at least a portion of the second metal, and the third metal may be the same or different from the first metal. In some cases, each metal may independently have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, less than about 80 nm, less than about 60 nm, less than about 40 nm, less than about 30 nm, less than about 20 nm, less than about 10 nm, less than about 8 nm, less than about 6 nm, less than about 4 nm, or less than about 2 nm, etc., and the layers may be of the same or different thicknesses.

Any suitable technique can be used for depositing metals, and if more than one metal is used, the techniques for depositing each of the metals may independently be the same or different. For example, in one set of embodiments, deposition techniques such as sputtering can be used. Other examples include, but are not limited to, physical vapor deposition, vacuum deposition, chemical vapor deposition, cathodic arc deposition, evaporative deposition, e-beam PVD, pulsed laser deposition, ion-beam sputtering, reactive sputtering, ion-assisted deposition, high-target-utilization sputtering, high-power impulse magnetron sputtering, gas flow sputtering, or the like.

The metals can be chosen in some cases such that the deposition process yields a pre-stressed arrangement, e.g., due to atomic lattice mismatch, which causes the subsequent metal leads to warp or bend, for example, once released from the substrate.

Although such processes were typically undesired in the prior art, in certain embodiments of the present invention, such pre-stressed arrangements may be used to cause the resulting cell scaffold to form a 3-dimensional structure, in some cases spontaneously, upon release from the substrate. However, it should be understood that in other embodiments, the metals may not necessary be deposited in a pre-stressed arrangement.

Examples of metals that can be deposited (stressed or unstressed) include, but are not limited to, aluminum, gold, silver, copper, molybdenum, tantalum, titanium, nickel, tungsten, chromium, palladium, as well as any combinations of these and/or other metals. For example, a chromium/palladium/chromium deposition process, in some embodiments, may form a pre-stressed arrangement that is able to spontaneously form a 3-dimensional structure after release from the substrate.

In certain embodiments, a "coating" polymer can be deposited (240 in FIG. 2), e.g., on at least some of the conductive pathways and/or at least some of the nanoscale wires. The coating polymer may include one or more polymers, which may be deposited as one or more layers. In some embodiments, the coating polymer may be deposited on one or more portions of a substrate, e.g., as a layer of material such that portions of the coating polymer can be subsequently removed, e.g., using lithographic techniques such as e-beam lithography, photolithography, X-ray lithography, extreme ultraviolet lithography, ion projection lithography, etc., or using other techniques for removing polymer that are known to those of ordinary skill in the art, similar to the other polymers previously discussed. The coating polymers can be the same or different from the lead polymers and/or the bedding polymers. In some cases, more than one coating polymer may be used, e.g., deposited as more than one layer (e.g., sequentially), and each layer may independently have a thickness of less than about 5 micrometers, less than about 4 micrometers, less than about 3 micrometers, less than about 2 micrometers, less than about 1 micrometer, less than about 900 nm, less than about 800 nm, less than about 700 nm, less than about 600 nm, less than about 500 nm, less than about 400 nm, less than about 300 nm, less than about 200 nm, less than about 100 nm, etc.

Any suitable polymer may be used as the coating polymer. In some cases, one or more of the polymers can be chosen to be biocompatible and/or biodegradable. For example, in one set of embodiments, one or more of the polymers may comprise poly(methyl methacrylate). In certain embodiments, one or more of the coating polymers may comprise a photoresist, e.g., as discussed herein.

In certain embodiments, one or more of the coating polymers can be heated or baked, e.g., before or after depositing nanoscale wires thereon as discussed below, and/or before or after patterning the coating polymer. For example, such heating or baking, in some cases, is important to prepare the polymer for lithographic patterning. In various embodiments, the coating polymer may be heated to a temperature of at least about 30° C., at least about 65° C., at least about 95° C., at least about 150° C., or at least about 180° C., etc.

After formation of the cell scaffold, some or all of the sacrificial material may then be removed in some cases. In one set of embodiments, for example, at least a portion of the sacrificial material is exposed to an etchant able to remove the sacrificial material. For example, if the sacrificial material is a metal such as nickel, a suitable etchant (for example, a metal etchant such as a nickel etchant, acetone, etc.) can be used to remove the sacrificial metal. Many such etchants may be readily obtained commercially. In addition, in some embodiments, the cell scaffold can also be dried, e.g., in air (e.g., passively), by using a heat source, by using a critical point dryer, etc.

In certain embodiments, upon removal of the sacrificial material, pre-stressed portions of the cell scaffold (e.g., metal leads containing dissimilar metals) can spontaneously cause the cell scaffold to adopt a 3-dimensional structure. In some cases, the cell scaffold may form a 3-dimensional structure as discussed herein. For example, the cell scaffold may have an open porosity of at least about 30%, at least about 40%, at least about 50%, at least about 60%, at least about 70%, at least about 75%, at least about 80%, at least about 85%, at least about 90%, at least about 95%, at least about 97, at least about 99%, at least about 99.5%, or at least about 99.8%. The cell scaffold may also have, in some cases, an average pore size of at least about 100 micrometers, at least about 200 micrometers, at least about 300 micrometers, at least about 400 micrometers, at least about 500 micrometers, at least about 600 micrometers, at least about 700 micrometers, at least about 800 micrometers, at least about 900 micrometers, or at least about 1 mm, and/or an average pore size of no more than about 1.5 mm, no more than about 1.4 mm, no more than about 1.3 mm, no more than about 1.2 mm, no more than about 1.1 mm, no more than about 1 mm, no more than about 900 micrometers, no more than about 800 micrometers, no more than about 700 micrometers, no more than about 600 micrometers, or no more than about 500 micrometers, etc.

However, in other embodiments, further manipulation may be needed to cause the cell scaffold to adopt a 3-dimensional structure, e.g., one with properties such as is discussed herein. For example, after removal of the sacrificial material, the cell scaffold may need to be rolled, curled, folded, creased, etc., or otherwise manipulated to form the 3-dimensional structure. Such manipulations can be done using any suitable technique, e.g., manually, or using a machine.

Other materials may be also added to the cell scaffold, e.g., before or after it forms a 3-dimensional structure, for example, to help stabilize the structure, to add additional agents to enhance its biocompatibility (e.g., growth hormones, extracellular matrix protein, MATRIGEL™, etc.), to cause it to form a suitable 3-dimension structure, to control pore sizes, etc. Non-limiting examples of such materials have been previously discussed above, and include other polymers, growth hormones, extracellular matrix protein, specific metabolites or nutrients, additional scaffold materials, or the like.

In addition, in some cases, cells are plated or seeded on the cell scaffold and allowed to grow. For example, the cells may be plated on the cell scaffold in vitro, and/or the cell scaffold may be exposed or even submerged within a suitable cell growth medium. Such media are widely available commercially. In some embodiments, the cell scaffold can be subsequently implanted in vivo into a subject, e.g., upon the growth of suitable from the cells. In other cases, the cell scaffold can directly be used in an in vivo setting, i.e., without needing plating of cells, and/or without formation of tissues before implantation.

In addition, the cell scaffold can be interfaced in some embodiments with one or more electronics, e.g., an external electrical system such as a computer or a transmitter (for instance, a radio transmitter, a wireless transmitter, etc.). In some cases, electronic testing of the cell scaffold may be performed, e.g., before or after implantation into a subject. For instance, one or more of the metal leads may be connected to an external electrical circuit, e.g., to electronically interrogate or otherwise determine the electronic state or one or more of the nanoscale wires within the cell scaffold. Such determinations may be performed quantitatively and/or qualitatively, depending on the application, and can involve all, or only a subset, of the nanoscale wires contained within the cell scaffold, e.g., as discussed herein.

The following documents are incorporated herein by reference: U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; U.S. Pat. No. 7,301,199, issued Nov. 27, 2007, entitled "Nanoscale Wires and Related Devices," by Lieber, et al.; and International Patent Application No. PCT/US2010/050199, filed Sep. 24, 2010, entitled "Bent Nanowires and Related Probing of Species," by Tian, et al., published as WO 2011/038228 on Mar. 31, 2011.

In addition, incorporated herein by reference is a U.S. provisional application, filed on even date herewith, entitled "Scaffolds Comprising Nanoelectronic Components for Cells, Tissue, and Other Applications," by Lieber, et al. Also incorporated herein by reference in their entireties are U.S. Prov. Pat. Apl. Ser. No. 61/698,492, entitled "Methods And Systems For Scaffolds Comprising Nanoelectronic Components," filed Sep. 7, 2012, and U.S. Prov. Pat. Apl. Ser. No. 61/698,502, entitled "Scaffolds Comprising Nanoelectronic Components For Cells, Tissues, And Other Applications," filed Sep. 7, 2012.

The following examples are intended to illustrate certain embodiments of the present invention, but do not exemplify the full scope of the invention.

Example 1

The development of three-dimensional (3D) synthetic biomaterials as structural and bioactive extracellular matrices (ECMs) is central to fields ranging from cellular biophysics to regenerative medicine. As of yet, it has not been possible to provide spatiotemporal monitoring of cells throughout 3D scaffolds, although this capability could have a marked impact. This example illustrates a new platform of seamlessly integrating nanoelectronic devices into freestanding, flexible, and biocompatible nanoelectronic scaffolds (nanoES) for 3D cell and tissue applications.

The scaffolds in this and the following examples were prepared by planar lithography with nanowire transistors serving as sensor elements and metal interconnects sandwiched between biocompatible polymeric scaffold networks. 3D macroporous scaffold structures were formed either by self-organization of coplanar reticular networks with built-in strain or by manual folding or rolling of 2D mesh matrices. The scaffolds exhibited robust electronic properties during conversion from planar networks to 3D structures, and were used as extracellular scaffolds for efficient 3D culture of neurons, cardiomyocytes and smooth muscle cells. Notably, multiplexed electrical recordings of extracellular potentials from 3D innervated cardiac patches demonstrated the feasibility of continuous monitoring in 3D of excitation propagation. 3D distributed nanoelectronic devices were also used for simultaneous monitoring of pH inside and outside tubular vascular smooth muscle constructs. This approach allows functionalizing engineered tissues, indwelling 3D tissue-based therapeutic assays, enhanced biomedical prosthetics, and makes possible novel biomaterials/biosystems where the distinction between biological and electronic systems becomes blurred.

This approach integrates nanoelectronics into tissues in 3D. Silicon nanowire field-effect transistor-based nanoelectronic biomaterials were used given their capability for recording both extracellular and intracellular signals with subcellular resolution. This design (FIG. 3) involved stepwise incorporation of biomimetic and biological elements into nanoelectronic networks across nanometer to centimeter size scales. First, chemically synthesized kinked and/or uniform silicon nanowires were deposited either randomly or in regular patterns for single-nanowire FETs (step A, FIG. 3), forming the nanoelectronic sensor elements of the hybrid biomaterials. Second, individual nanowire field-effect transistor (NWFET) devices were lithographically patterned and integrated into free-standing macroporous scaffolds (step B, FIG. 3), termed "nanoelectronic scaffolds (nanoES)." The nanoES were tailored to be 3D, to have nanometer to micrometer features with high (>99%) porosity, and to be highly flexible and biocompatible. NanoES could also be hybridized with biodegradable synthetic or natural macroporous ECMs providing ECMs with electrical sensory function and nanoES with biochemical environments suitable for tissue culture. Finally, cells were cultured on nanoES (step C, FIG. 3).

Figure 3:
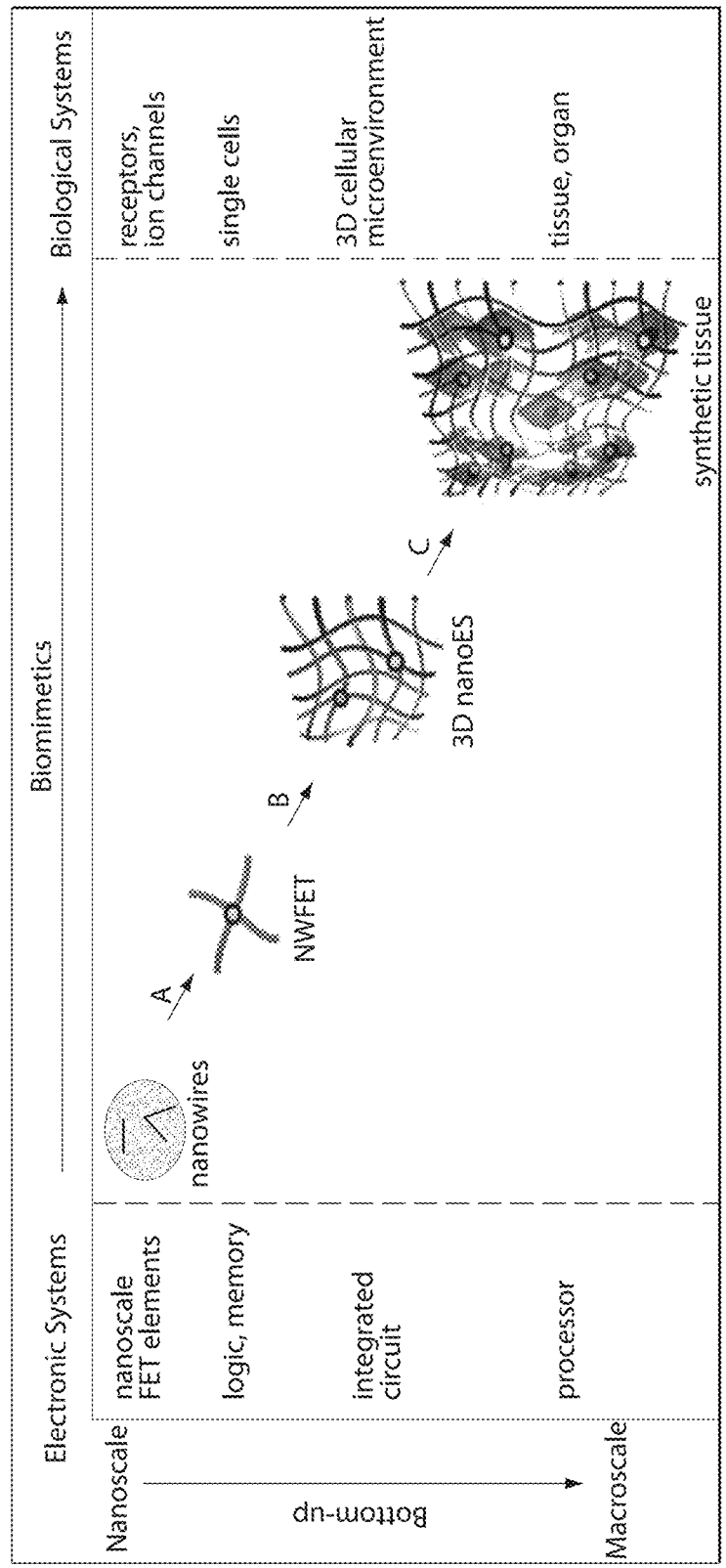
FIG. 3 is a schematic representation of an integrated system using discrete building blocks of electronic and biological systems, in some embodiments of the invention.

In particular, FIG. 3 schematically illustrates that conventional bulk electronics (left column) are distinct from biological systems (right column) in composition, structural hierarchy, mechanics and function. Their electrical coupling at the tissue/organ level is usually limited to the tissue surface, where only boundary or global information can be gleaned unless invasive approaches are used. The present example, in contrast, demonstrates an integrated system from the discrete building blocks of electronic and biological systems, e.g., semiconductor nanowires, molecular precursors of polymers and single cells. These biomimetic and bottom-up steps are used: A) patterning, metallization and epoxy passivation to form single NWFETs, B) forming 3D NWFETs matrices (nanoelectric scaffolds) by self- or manual organization and hybridization with synthetic biomaterials, and C) incorporation of cells and growth of synthetic tissue via biological processes. In these figures, the circles represent nanowire components, and the ribbons represent metal and epoxy interconnects (darker ribbons), and traditional extracellular matrices (lighter ribbons).

As examples, two different types of nanoESs (FIG. 4A) were designed that were free-standing, flexible and contained similar components. Both were fabricated on sacrificial layers, which were subsequently removed, yielding free-standing nanoES. These will be discussed in greater detail below. In brief, a layer of resist (SU-8) was coated on a sacrificial layer of material, nanowires were deposited, the scaffold structure was patterned with lithography, metal interconnections were defined by lithography and deposition, a second layer of resist (SU-8) was coated thereon, and lithography was used to define this as the upper layer of passivation over the interconnects.

One type of nanoES was termed a "reticular" nanoES. The reticular nanoESs were made by electron beam lithography. Self-organization created a random or regular network of 3D features that mimiced the size scale and morphology of submicron ECM features, like the fibrous meshwork of brain ECM. The other type was called a "mesh" nanoES. The mesh nanoESs were made by photolithography with a regular structure, like the ECM of the ventricular myocardium. 3D aspects were created by rolling or folding these structures to form a 3D scaffold. 3D scaffolds were then realized in a straightforward manner by directed mesh manipulation. The planar design and initial fabrication of these 3D nanoES used existing capabilities similar to those developed for conventional planar nanoelectronics, and allow integration of additional device components (for example, memories and logic gates) or substantial increases in device number or overall scaffold size.

Figure 4B:
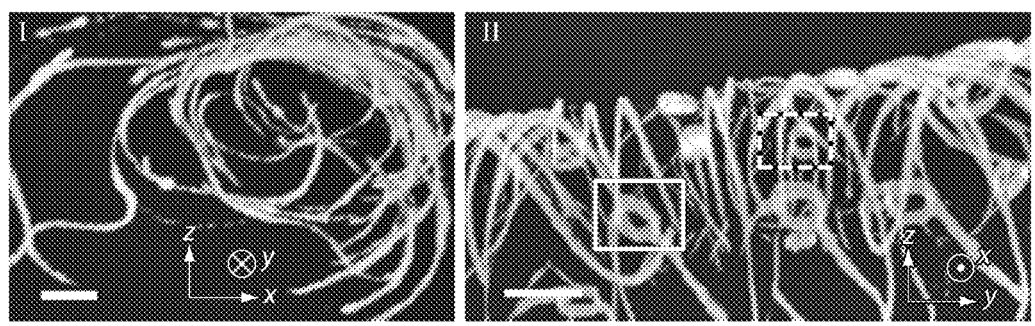
Figure 5:
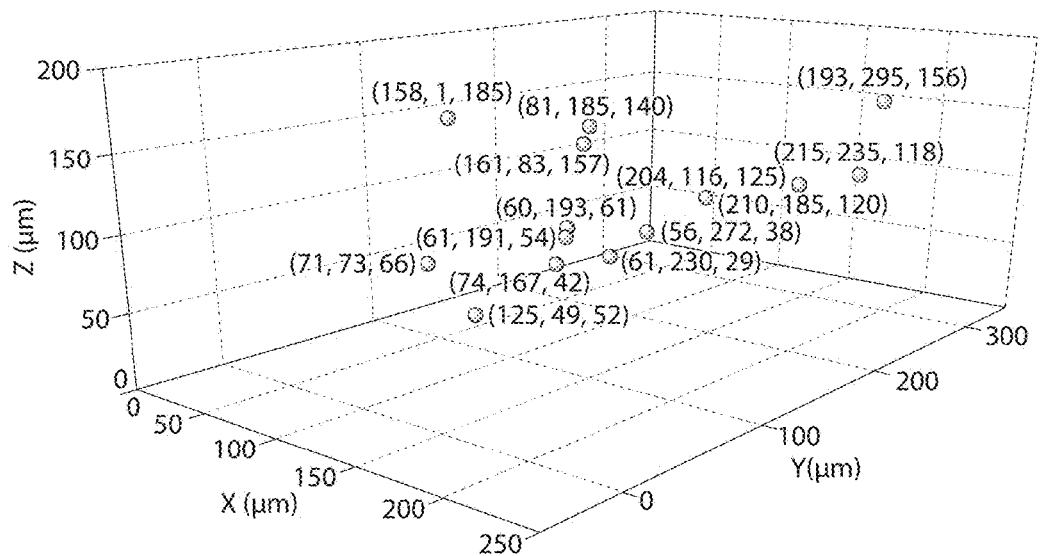
FIG. 5 illustrates the 3-dimensional distribution of nanoscale wires in a cell scaffold in yet another embodiment of the invention.

The 2D structure of the reticular scaffold was designed so that metal interconnects were stressed. Removal of the sacrificial layer prompted self-organization into 3D. Reconstructed 3D confocal fluorescence images of a typical reticular nanoES viewed along y- and x-axes (FIG. 4B, Panels I and II respectively) showed that the framework was 3D with a highly curvilinear and interconnected structure consistent with the design (FIG. 4A, Panel I). The porosity (calculated from the initial planar device design and the final 3D construct volume) was greater than 99.8%, comparable to that of hydrogel biomaterials. NWFET devices (FIG. 4B, Panel II) within the scaffold spanned separations of 7.3 to 324 micrometers in 3D (FIG. 5), and the reticular scaffold heights were less than about 300 micrometers for these fabrication conditions. In addition, the devices could also be made closer together (for example, less than 0.5 micrometers), e.g., by depositing the nanowires more densely on the substrate, for instance, to improve the spatial resolution of nanoelectronic sensors; the span of device separations and scaffold heights can also be increased substantially using larger field lithography. FIG. 5 shows a NWFET 3D distribution in fibrous nanoES. 14 NWFETs were distributed in the construct shown in FIG. 4B. Individual devices are shown as solid spheres. The overall size of the scaffold, x-y-z was ~300-400-200 micrometers. The NWFET devices within the scaffold were separated in 3 dimensions by 7.3 micrometers to 324 micrometers.

Figure 4C:
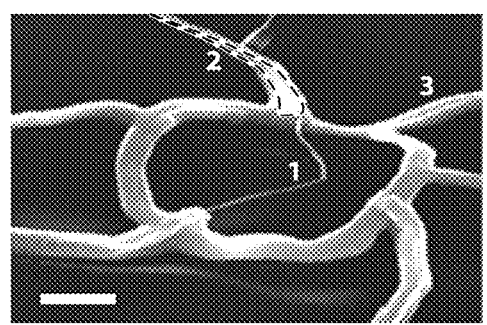

Scanning electron microscopy (SEM) of the reticular nanoES (FIG. 4C) revealed kinked nanowires (about 80 nm in diameter), and metallic interconnects (about 0.7 micrometers in diameter) contained within an SU-8 backbone (about 1 micrometer in width). The feature sizes were comparable to those of synthetic and natural ECMs, and were several orders of magnitude smaller than those of reported electronic structures penetrating tissue in 3D. Water-gate measurements of the NWFET elements of the 3D scaffolds in aqueous medium (see below) demonstrated device yields of ~80%, conductances of 1.52+/−0.61 microsiemens (mean+/−SD) and sensitivities of 8.07+/−2.92 microsiemens/V, comparable to measurements from planar devices using similar nanowires.

Figure 4D:
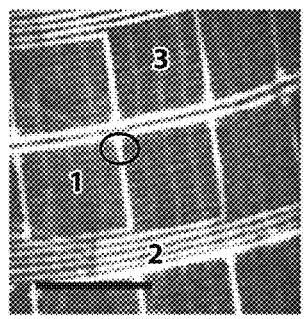
Figure 4E:
Figure 4F:
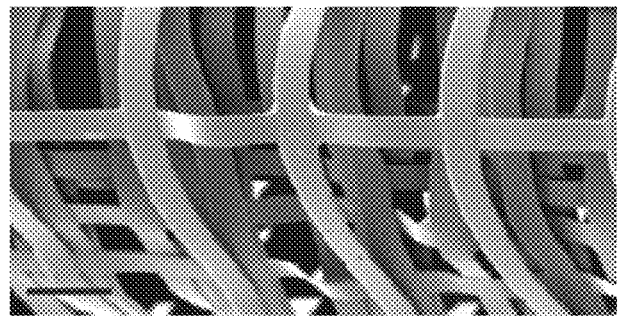

The 3D mesh nanoES were prepared by manual folding and rolling of free-standing device arrays. The mesh structures (FIG. 4A, Panel II) were fabricated such that the nanoES maintained an approximately planar configuration following relief from the fabrication substrate (see below). A typical 3.5 cm×1.5 cm×~2 micrometer mesh nanoES (FIG. 4D), was substantially planar with 60 addressable NWFET devices distributed in a regular array (FIG. 4D) and had a 2D open porosity of 75% (FIG. 4D). The mesh porosity was comparable to that of honeycomb-like synthetic ECM engineered for cardiac tissue culture. The nanowires (1 in FIG. 4D), metal interconnects (2 in FIG. 4D), and SU-8 structural elements (3 in FIG. 4D) had an areal mass density of less than 60 micrograms/cm$^2$. The mesh nanoES was highly flexible and could be manually rolled into tubular 3D constructs with inner diameters at least as small as 1.5 mm (FIG. 4E), and folded. Macroporous structures of the open mesh nanoES were formed either by loosely stacking adjacent mesh layers (FIG. 4F) or by shaping it with other biomaterials. These capabilities were consistent with the estimated ultralow effective bending stiffness, which was tuned between 0.006 and 1.3 nNm for this mesh and was comparable to planar epidermal electronics.

Figure 4G:
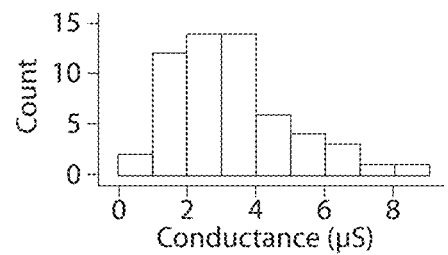
Figure 4G:
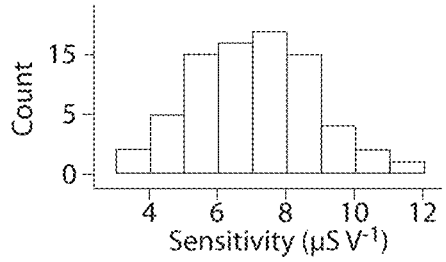
Figure 4H:
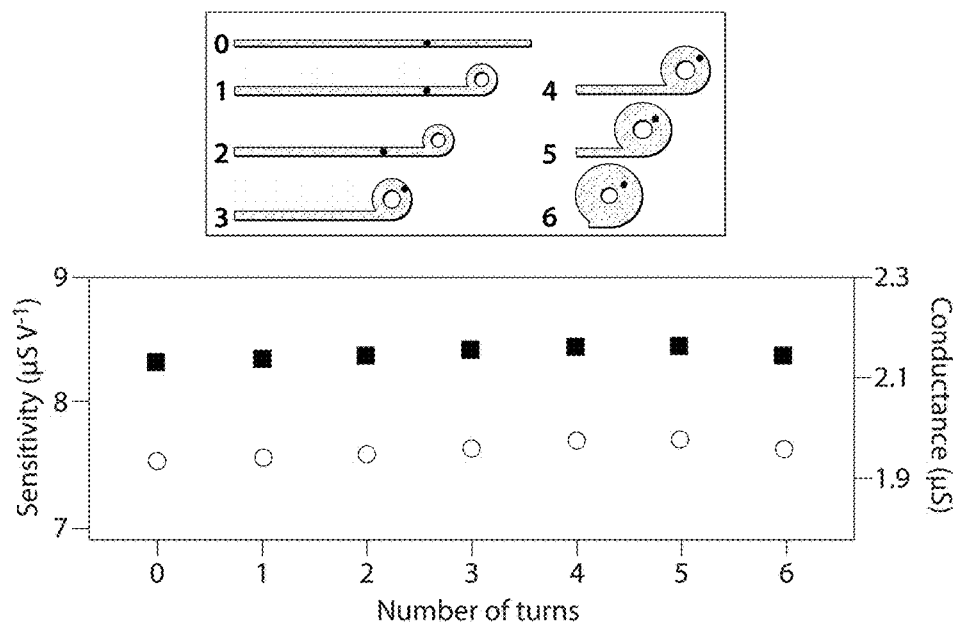
Figure 4I:
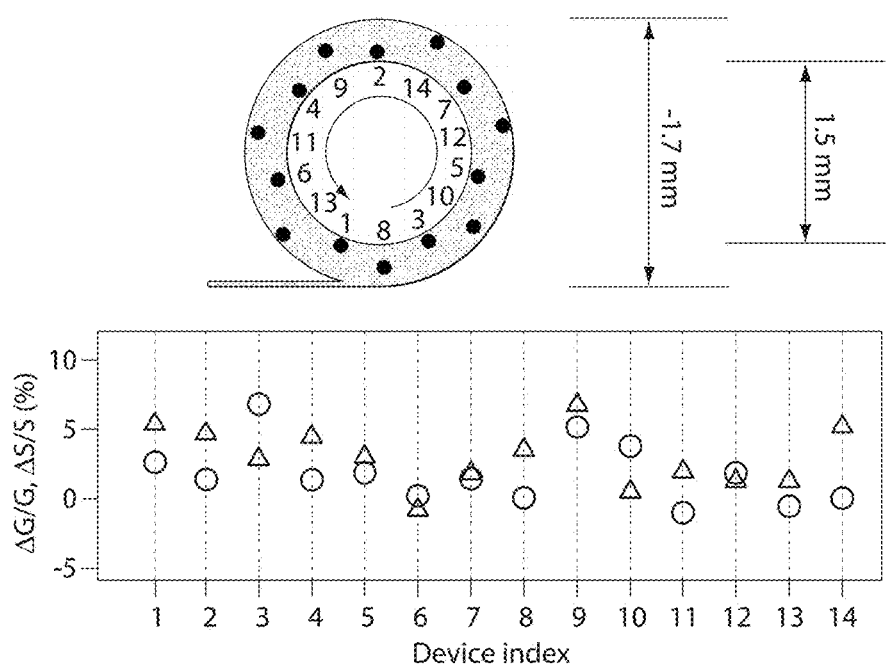

The electrical transport characteristics of the mesh nanoES was evaluated in phosphate buffered saline (PBS. The typical device yield was 90-97%, with average device conductances of ~3 microsiemens and sensitivity of ~7 microsiemens per volt (FIG. 4G). Representative data (FIG. 4H) from single NWFET (FIG. 4H, light dots in upper panel) showed a less than 0.17 microsiemens conductance change (ΔG) or less than 2.3% total change for 6 revolutions. The device sensitivity (S) remained stable with a maximum change (ΔS) of 0.031 microsiemens/V, or a 1.5% variation. The stable device performance can be explained by the low estimated strains of metal (less than 0.005%) and SU-8 (less than 0.27%) layers in this tubular construct (see below), and showed that electrical transport properties were substantially independent of location. Furthermore, 14 devices evenly distributed on 6 layers of a fully rolled-up tubular scaffold (FIG. 4I) showed a maximum conductance change (ΔG) of 6.8% and a maximum change in device sensitivity (ΔS) of 6.9%, versus the initial unrolled state, indicating robust NWFETs. Repetitive rolling and relaxation to the flat state did not degrade NWFET performance. These findings suggested reliable sensing/recording of these dynamic and deformable systems.

Additional details regarding FIG. 4 follow. FIG. 4A illustrates device fabrication schematics, in accordance to one embodiment of the invention, for both reticular NWFET devices (Panel I) and mesh NWFET devices (Panel II). In FIG. 4A, the dots represent individual NWFETs. The outer, larger square (lighter color) represents the silicon oxide substrate, while the inner, smaller square (darker color) represents the nickel sacrificial layers. The ribbons on the right of each figure represents the nanoES scaffold constructs that are formed. FIG. 4B shows 3D reconstructed confocal fluorescence images of reticular nanoES viewed along the y (Panel I) and x (Panel II) axes. The scaffold was labeled with rhodamine 6G. The overall size of the structure (x-y-z) was 300-400-200 micrometers. The solid and dashed open boxes indicate two NWFET devices located on different planes along x axis. The scale bars are 20 micrometers. FIG. 4C is an SEM image of a single kinked NWFET within a reticular scaffold, showing (1) kinked nanowires, (2) metallic interconnects (lines) and (3) the SU-8 backbone construct. The scale bar is 2 micrometers. FIG. 4D shows a photograph of a mesh device showing (1) nanowires, (2) metal interconnects, and (3) SU-8 structural elements. The circle indicates the position of a single NWFET. The scale bar is 2 mm. FIG. 4E is a photograph of a partially rolled-up mesh device. The scale bar is 5 mm. FIG. 4F is a SEM image of a loosely packed mesh nanoES, showing the macroporous structure. The scale bar is 100 micrometers. FIG. 4G is a histogram of nanowire FET conductance and sensitivity in one typical mesh nanoES. The conductance and sensitivity were measured in the water-gate configuration without rolling. The device yield for this mesh nanoES was 95%. FIG. 4H shows water-gate sensitivity and conductance of a NWFET device during the rolling process in a mesh device. The upper panel of FIG. 4H is a schematic of the position of a NWFET (dot) during rolling process; 0-6 denote the number of turns. FIG. 4I shows the relative change in conductance and sensitivity of 14 NWFETs evenly distributed throughout a fully rolled-up mesh device. The upper panel is a schematic of the NFWET position (dots). In both FIGS. 4H and 4I, the thicknesses of the tubular structures have been exaggerated for schematic clarity.

Example 2

Simulations of a subunit of the self-organizing reticular structure were performed (FIG. 6A-C) in this example. Measurements of bending for the corresponding experimental structures (FIG. 6C, open squares) were found to be consistent with the simulations (FIG. 6C). Additionally, changes in structural parameters (for example, the total length of the subunit and thicknesses of SU-8 or metals) yielded predictable changes in the bending angle of the subunit (FIG. 7). This example thus shows that ordered 3D nanowire FET arrays could be designed and fabricated using reticular- or mesh-like structures that incorporated multilayer metal interconnects with built-in stress to self-organize (roll-up) the scaffold (FIG. 7).

Figure 6A:
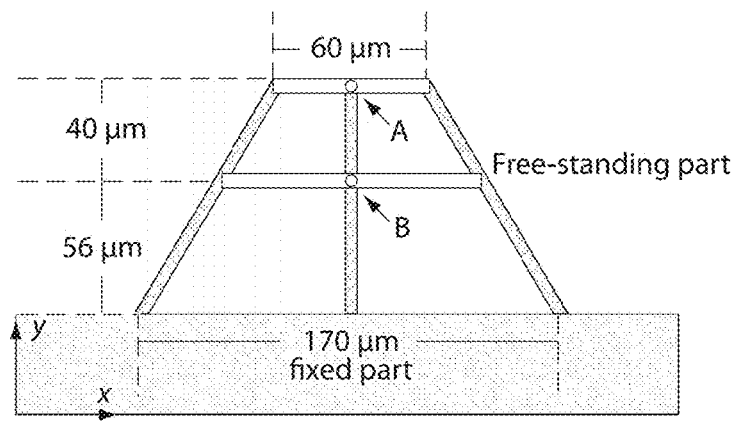
FIGS. 6A-6F illustrate the geometry of nanoscale wires, in accordance with certain embodiments of the invention.
Figure 6B:
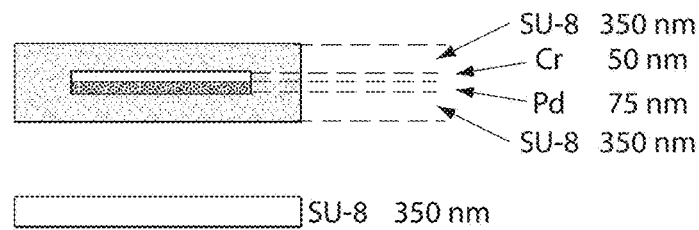
Figure 6C:
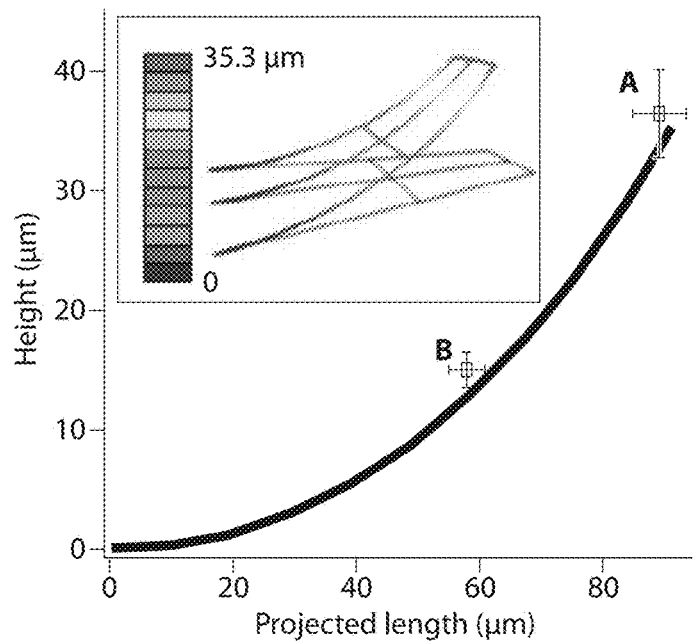
Figure 6D:
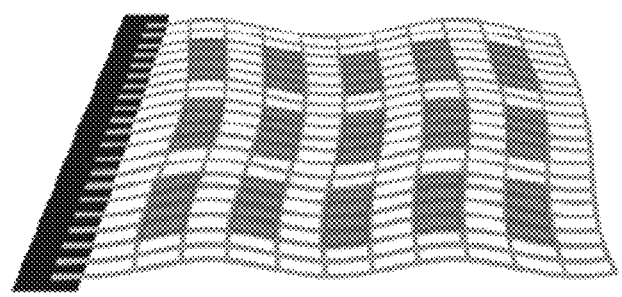

In addition, in some experiments, reticular domains were designed in mesh-like structures (FIG. 6D). Images of reticular domains (FIGS. 6E and 6F) showed that regular nanowire FET devices with distinct device positions could be realized, for example, by varying the structural parameters of individual elements. Overall, this approach yielded hierarchical 3D nanoES with submicrometer to micrometer scale control in reticular domains and millimeter to centimeter scale in the mesh matrix by folding or rolling as shown above (FIG. 4).

The reticular and mesh nanoES were also merged with conventional macroporous biomaterials in some of these experiments. Specifically, gel casting, lyophilization and electrospinning were used to deposit and construct macroporous collagen (FIG. 8A), alginate (FIG. 8B) and poly(lactic-co-glycolic acid) (PLGA; FIG. 8C), respectively, around nanoES structures. A confocal fluorescence micrograph of a hybrid reticular nanoES/collagen scaffold (FIG. 8A) showed that the collagen nanofibers (arrow) were fully entangled with the nanoES, with no apparent phase separation.

SEM images of the open mesh nanoES/alginate hybrid scaffold produced by lyophilization (FIG. 8B) showed that the flexible nanoES mesh was intimately anchored to the alginate framework, which had a similar pore structure as the pure alginate scaffold prepared under similar conditions. Optical micrographs of a multilayered mesh nanoES/PLGA scaffold (FIG. 8C), which was prepared by electrospinning PLGA fibers on both sides of the nanoES and subsequent folding of the hybrid structure, highlighted the intimate contact between nanoES mesh and PLGA fibers. The hybrid nanoES/biomaterial 3D scaffolds retained the original nanowire FET device characteristics. For example, measurements in 1× phosphate buffered saline solution showed that and ΔG/G, and ΔS/S were less than +/−9% for the mesh nanoES/PLGA composite versus bare nanoES. The hybrid nanoES scaffolds were stable under cell culture conditions. For example, nanowire FET devices in the hybrid reticular nanoES/MATRIGEL™ scaffold in neuron culture media (FIG. 8D) had ΔS/S less than +/−11% over a nine-week period, showing capability for long-term culture and monitoring with the nanoES. These results showed that nanoES scaffolds could be combined with conventional biomaterials to produce hybrid scaffolds that provide nanoscale electrical sensory components distributed in three dimensions.

FIGS. 6A and 6B illustrate the basic design and structural subunit for simulation. In FIG. 6A, a top-down view of the entire subunit is shown. Ribbons are stressed metal lines with SU-8 passivation. Lines are single SU-8 ribbons without residual stress. FIG. 6B shows a cross-sectional views of those two key structural elements used for simulation. FIG. 6C is a plot of projected (on the x-y plane) length versus height (in the z direction) for the vertical ribbon in FIG. 6A as determined from the simulation. Open squares with error bars are experimental data (mean+/−SD) recorded in air for point A and B in FIG. 6A. The simulation of the bending of the subunit model for the reticular structure was carried out using the commercial finite element software ABAQUS. The inset shows a 3D view of the simulated structure, and the scale bar shows different heights in the z direction.

Figures 6E, 6F:
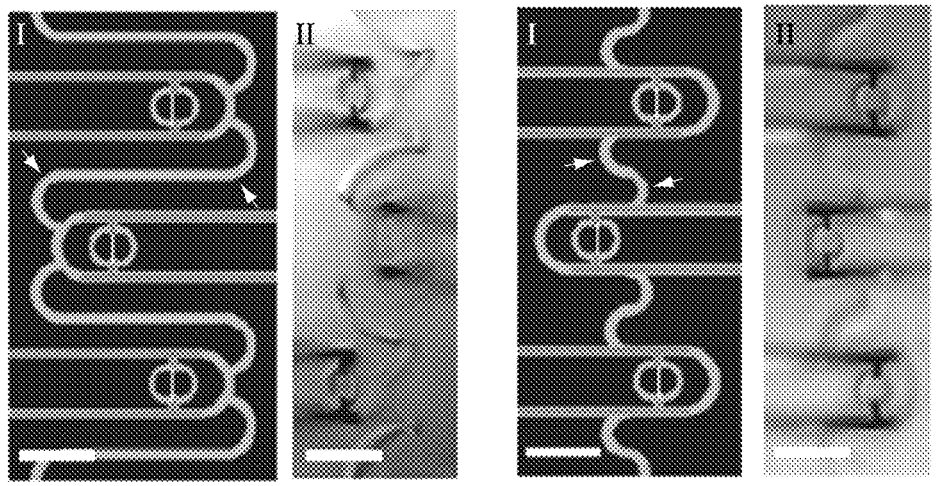

FIG. 6D is a schematic showing the integration of periodic reticular-device domains (filled rectangles) into a flexible mesh. In individual reticular domains, the 3D device positions relative to the global flexible mesh could be controlled by their geometry designs (FIG. 6A-C). In FIGS. 6E and 6F, design patterns (I) and experimental data (II) for two reticular units are shown. SU-8, metal and nanowires are shown in this figure. In FIG. 6E, changing the structure of the connecting feature (arrows) between adjacent device units during pattern design (I) yielded controlled variations in the 3D positioning of the nanowire FETs, which could be further tuned by the stress in the metal connections. In these experiments, the device positions were 40 micrometers (FIG. 6E, panel II) and 23 micrometers (FIG. 6F, panel II) above the mesh plane. The scale bars in FIGS. 6E and 6F are 20 micrometers.

Figure 7A:
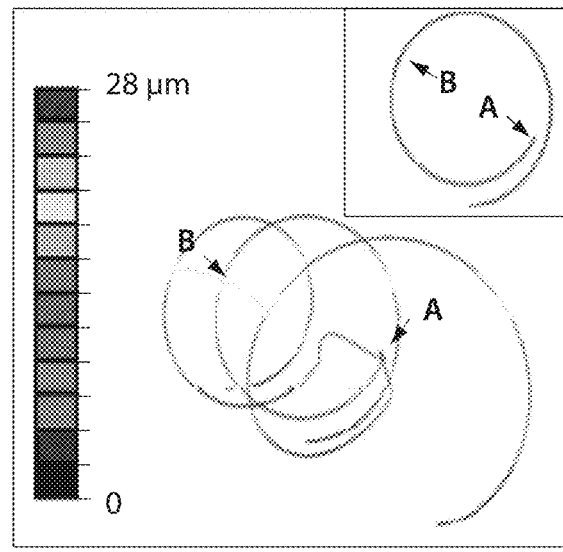
FIGS. 7A-7E illustrate design and fabrication of nanoscale wires, in accordance with certain embodiments of the invention.
Figure 7B:
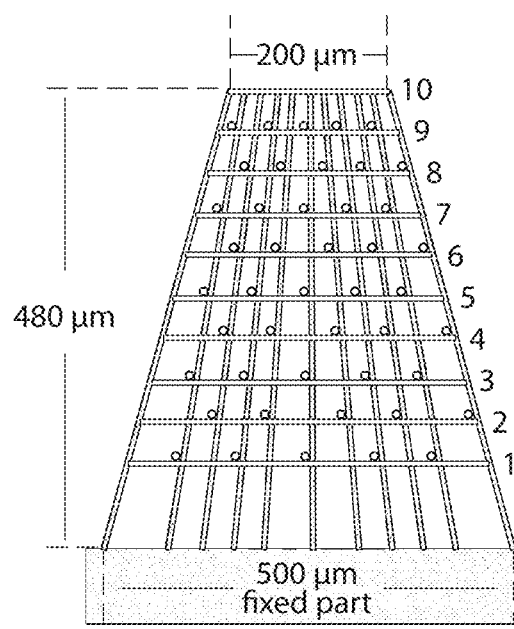
Figure 7C:
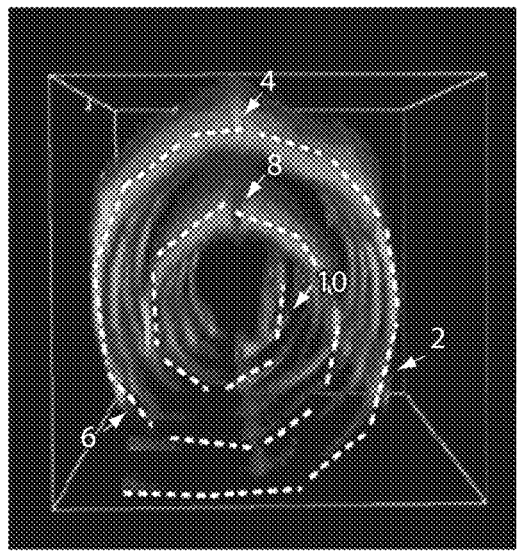
Figure 7D:
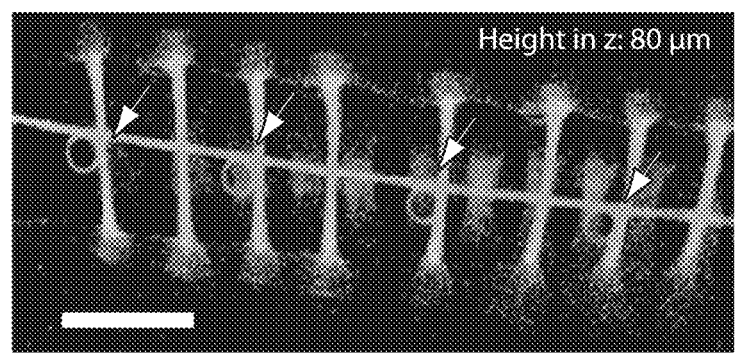
Figure 7E:
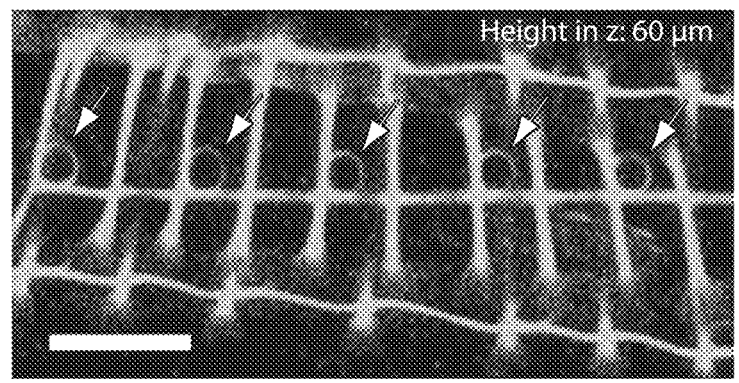

In FIG. 7A, the simulation showed that when the equivalent bending moment is increased by 10 times, the subunit structure scrolled up on itself. The inset shows the curve of the central vertical ribbon in FIG. 6A, demonstrating the devices were scrolled up and different layers were separated. A and B are the two points in FIG. 6A. FIGS. 7B-E show the design and fabrication of a much larger and regular matrix and the density of stressed elements increasing upward (from 1 to 10) in a manner analogous to the simulated subunit. In FIG. 7B, the vertical lines indicate stressed metal lines with SU-8 as passivation, the horizontal lines indicate non-stressed metal lines for interconnection with SU-8 as passivation or SU-8 ribbon as framework, and the circles mark positions for devices. FIG. 7C is a 3D reconstructed confocal fluorescence image showing the side view of the corresponding fabricated reticular construct following the design in FIG. 7B. The dashed lines highlight the edge of the scrolled-up reticular nanoES construct. The white numbers and arrows indicate the position of 5 horizontal lines corresponding to those numbered in FIG. 7B. FIGS. 7D and 7E are confocal fluorescence images scanned across the interior of the scaffold at different heights. The images demonstrate that the device regions (circles) located in planes (heights of 80 and 60 micrometers are shown) were aligned, and thus demonstrated the regular arrangement in 3D. The scale bars in FIGS. 7D and 7E are 50 micrometers. Overall, the results show that larger scale simulations could be used to predict the reticular construct geometry, and allow the self-assembling approach to provide regular (or irregular) device arrays distributed through 3D space by design.

Figure 8A:
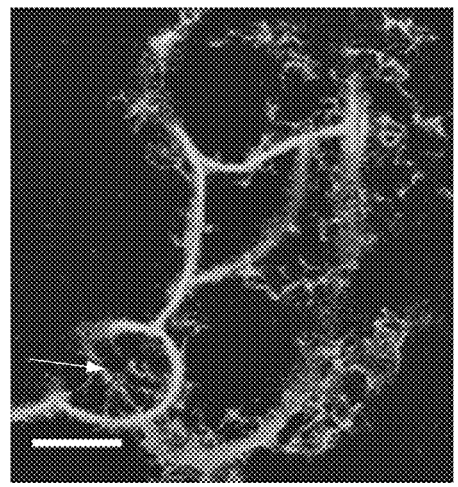
FIGS. 8A-8D illustrate cell scaffolds comprising nanoscale wires and analysis of sensitivity of nanoscale wires over time, in accordance with certain embodiments of the invention.
Figure 8B:
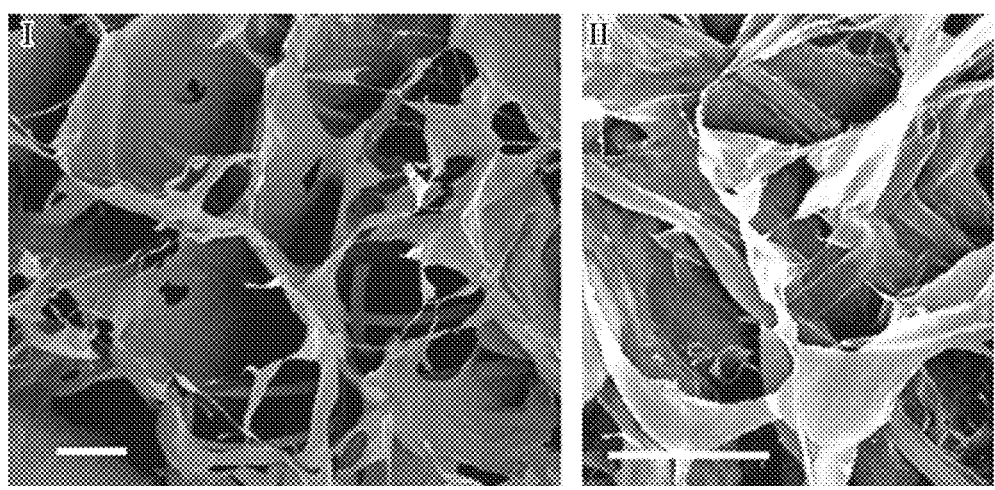
Figure 8C:
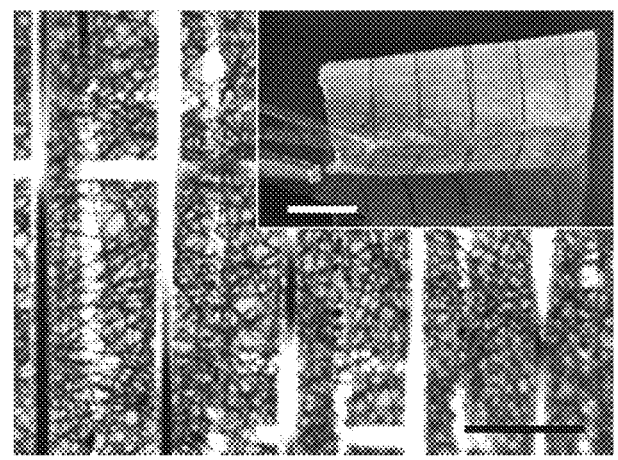
Figure 8D:
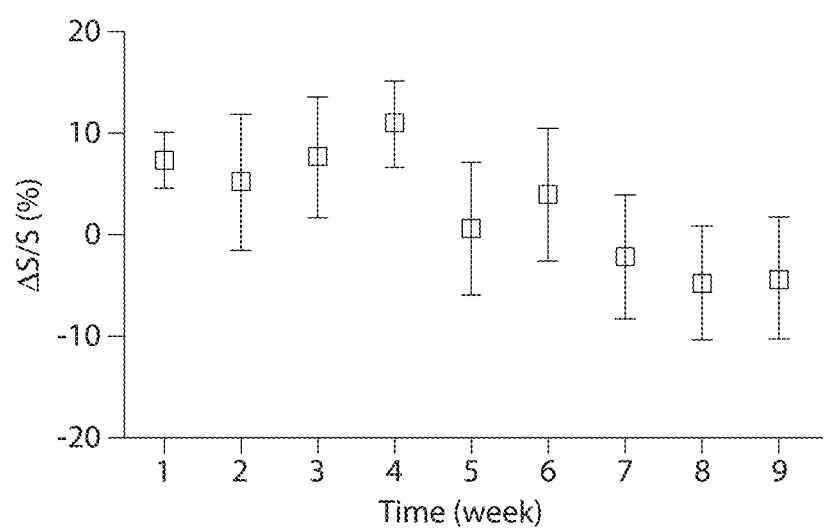

FIG. 8A is a confocal fluorescence micrograph of a hybrid reticular nanoES/collagen matrix. Collagen type-I was stained with fluorescein isothiocyanate; epoxy ribbons were stained with rhodamine 6G. The white arrow marks the position of the nanowire. The scale bar is 10 micrometers. FIG. 8B is a SEM images of a mesh nanoES/alginate scaffold with top (panel I) and side (panel II) views. The scale bars are 200 micrometers (panel I) and 100 micrometers (panel II). FIG. 8C is a bright-field optical micrograph of the folded scaffold, showing multilayered structures of PLGA and nanoelectronic interconnects. The inset shows a photograph of the hybrid sheet before folding. A sheet of PLGA fibers with diameters of about 1-3 micrometers was deposited on both sides of the device. No damage or reduction of device yield was observed following this deposition. The scale bars are 200 micrometers and 5 mm (inset). FIG. 8D illustrates the relative changes in nanowire FET sensitivity over time in culture (37° C.; 5% $CO_2$, supplemented NEUROBASAL™ medium), where n equals 5 and data are mean+/−SD.

Example 3

The reticular and mesh nanoES described in Example 1 were evaluated in 3D culture using several types of cells. Embryonic rat hippocampal neurons in MATRIGEL™ were cultured on the reticular nanoES for 7 to 21 days (FIG. 9). Representative 3D reconstructed confocal microscopy images (FIGS. 10A-B and FIG. 11) from a 2-week culture showed neurons with a high density of spatially interconnected neurites that penetrated the reticular nanoES, often passing through the ring-like structures supporting individual NWFETs (FIGS. 10B and 11. The widths of the scaffold constructs (passivated metal interconnects and structural ribbons) were similar to those of the neurite projections, demonstrating the merger of electronics with biological systems at an unprecedented similarity in scale.

In one set of experiments, 3D nanoelectronic cardiac culture was achieved from hybrid mesh nanoES/PLGA scaffolds (FIGS. 12-14). Confocal fluorescence microscopy of a folded cardiac construct (FIG. 10C) revealed a high density of cardiomyocytes in close contact with nanoES components (FIG. 10C). Epi-fluorescence images of cardiac cells on the surface of the nanoES cardiac patch also showed striations characteristic of cardiac tissue (FIG. 10D and FIGS. 13 and 14).

Figure 10E:
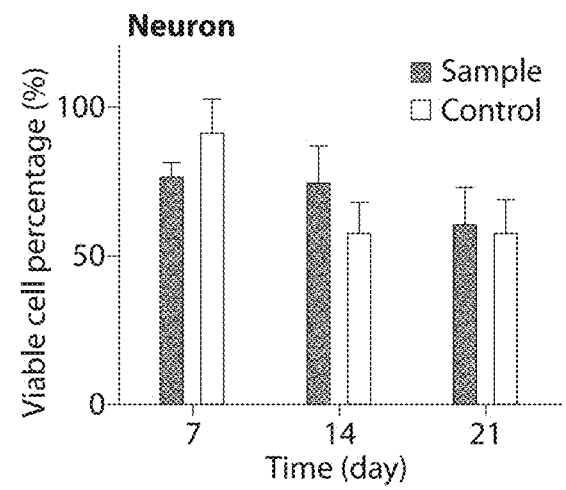
Figure 10F:
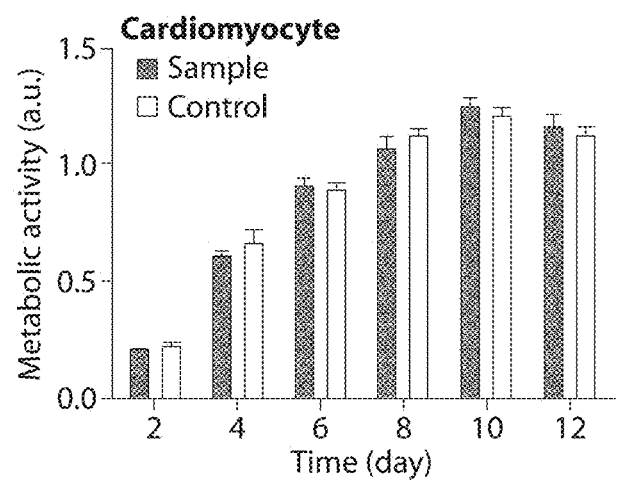

In vitro cytotoxicity of the nanoES was evaluated using 3D neural and cardiac culture systems (FIGS. 10E-F). Differences in hippocampal neuron viability on reticular nanoES/MATRIGEL™ versus MATRIGEL™ over 21 days were minimal, assessed with a standard live/dead cell assay (FIG. 10E), and between cardiac cells in hybrid mesh nanoES/MATRIGEL™/PLGA and MATRIGEL™/PLGA from 2 to 12 days, measured with a metabolic activity assay (FIG. 10F). These studies showed that on the 2-3 week timescale, the nanoES component of the scaffolds has little effect on the cell viability, and thus could be exploited for a number of in vitro studies, including drug screening assays with these synthetic neural and cardiac tissues. The main component of nanoES, SU-8, has been demonstrated to have long-term chronic biocompatibility suitable for in vivo recording.

FIG. 9 shows the chip assembly for neuronal 3D cultures. In FIG. 9A, a NWFET device chip containing a reticular nanoES was cleaned by $O_2$ plasma, and assembled onto a temperature controlled chip carrier. FIG. 9B shows a shallow PDMS chamber (dashed box) that was cleaned and placed over the wire-bonded devices. In FIG. 9C, a glass ring was fixed over the PDMS chamber with silicone elastomer. FIG. 9D shows a gas-permeable, water-impermeable membrane cover that was used for neuron cultures lasting longer than 7 days.

Figure 10G:
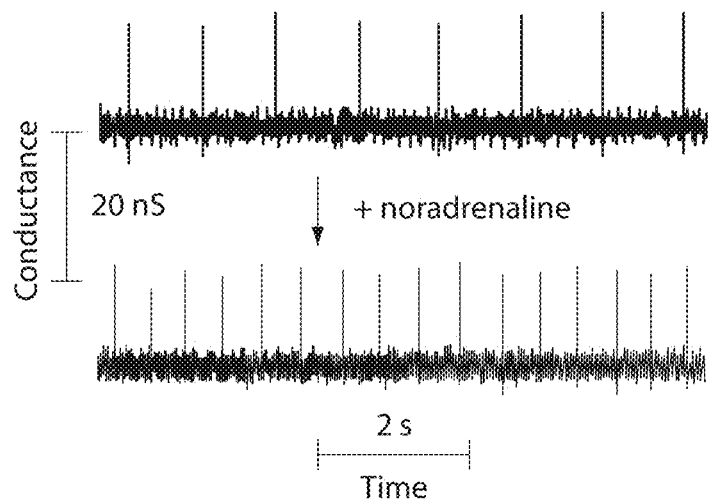
Figure 10H:
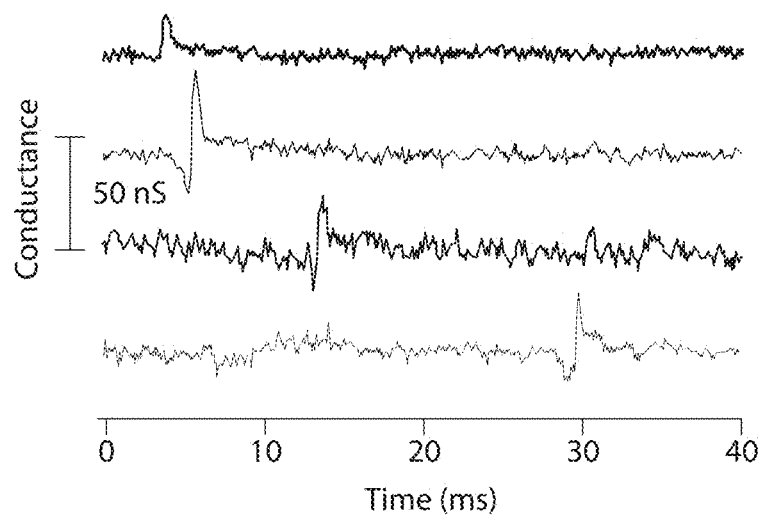

FIGS. 10A-B show 3D reconstructed confocal images of rat hippocampal neurons after 2 week culture in MATRIGEL™ on reticular nanoES. In these figures, neuronal beta-tubulin was stained with ALEXA FLUOR® 546, and epoxy ribbons were stained with rhodamine 6G. The metal interconnects are the relatively straight diagonal lines on the right of the image, and are imaged in reflected light mode. Four NWFET devices enclosed in polymer rings (arrows) can be seen. FIG. 10A: x: 317 micrometers; y: 317 micrometers; z: 100 micrometers; FIG. 10B, x: 127 micrometers; y: 127 micrometers; z: 68 micrometers. The star in Panel II denotes a neurite passing through a ring-like structure supporting a NFWET. FIG. 10C shows confocal fluorescence images of synthetic cardiac patch. In this figure, alpha-actinin of the cardiomyocytes was stained with ALEXA FLUOR® 488, cell nuclei (circular regions) were stained with Hoechst 34580, and PLGA fibers were stained with rhodamine 6G. Panels II and III are zoomed-in views of the upper and lower dashed regions of Panel I, showing metal interconnects, SU-8 scaffold (arrows in Panel II), and electrospun PLGA fibers (arrows in Panel III). Scale bars are 40 micrometers. FIG. 10D shows an epi-fluorescence image of the surface of the cardiac patch. Alpha-actinin (ribbons) was stained with ALEXA FLUOR® 488, while cell nuceli (circular regions) were stained with Hoechst 34580. The position of the source-drain electrodes is outlined with dashed lines; that of the nanowire in between them with an arrow. Scale bar is 40 micrometers. FIG. 10E shows the percentage of viable hippocampal neurons cultured in nanoES/MATRIGEL™ vs MATRIGEL™. Cell viability was evaluated with a LIVE/DEAD® cytotoxicity assay. Cells were counted from 3D reconstructed confocal fluorescence photomicrographs. n=6; data are mean+/−SD. The differences between groups were very small although statistically significant (p<0.05). FIG. 10F shows MTS cytotoxicity assay of cardiomyocytes evaluated using the MTS assay. n=6; data are mean+/−SD. The differences between groups were very small although statistically significant (p<0.05). FIG. 10G are conductance versus time traces recorded from a single-nanowire FET before (top) and after (bottom) applying noradrenaline. FIG. 10H is a multiplex electrical recording of extracellular field potentials from four nanowire FETs (labeled a-d) in a mesh nanoES. Data are conductance versus time traces of a single spike recorded at each nanowire FET.

Figure 11A:
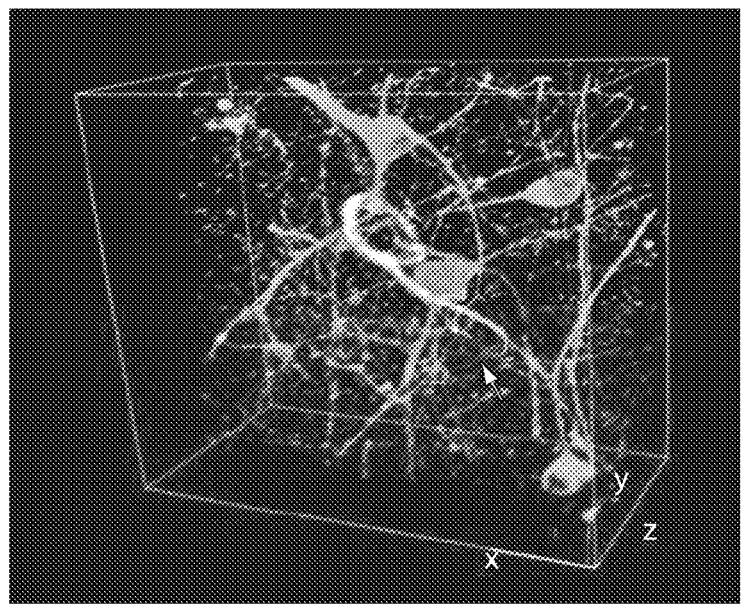
FIGS. 11A-11B illustrate 3-dimensional reconstructed confocal fluorescence image of a cell scaffold in accordance with one embodiment of the invention, illustrating the distribution of cells and metals within the scaffold.
Figure 11B:
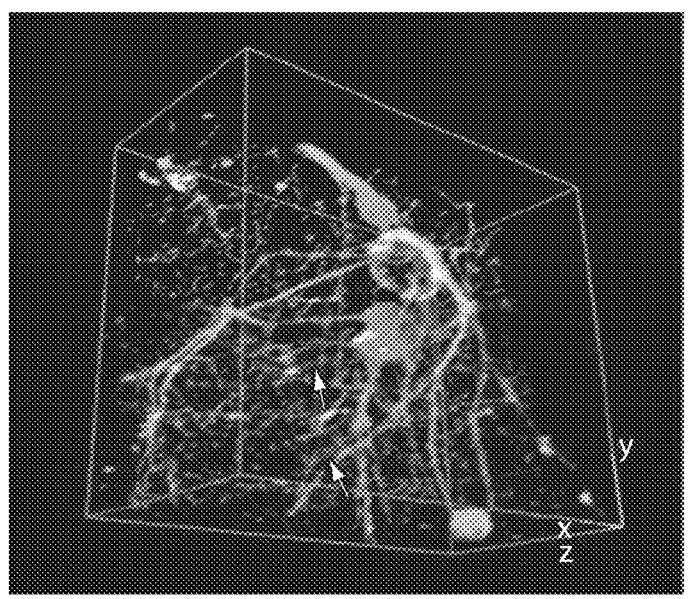

FIG. 11 shows 3D reconstructed confocal fluorescence image of rat hippocampal neurons within a reticular nanoES after two weeks in culture. The images show neurons (stained with fluorescent antibody against beta-tubulin) and polymer ribbons (doped with rhodamine 6G dye). The metal interconnects are marked with white arrows, and are imaged in reflected light mode. Dimensions are: x: 127 micrometers; y: 127 micrometers; z: 68 micrometers. The images were rotated from the view shown in FIG. 8B approximately as follows: (left image) 90 degrees about the z-axis, −10 degrees about the y-axis; (right image) 90 degrees about the z-axis, 100 degrees about the y-axis, 40 degrees about the x-axis. Together, these images show that neurites pass through the ringlike structures supporting individual nanowire FETs.

FIG. 13 shows fluorescence images from the surface of cardiac cell-seeded nanoES, showing alpha-actinin of cardiomyocytes (stained with ALEXA FLUOR® 488 in FIGS. 13A-C), cell nuclei (stained with Hoechst 34580 in FIGS. 13A-C) and PLGA fibers (stained with rhodamine 6G in FIGS. 13B-C). Dense cardiomyocyte growth was supported by both nanoES (marked by arrows) in FIG. 13A and electrospun PLGA fibers in hybrid PLGA/nanoES in FIG. 13B. FIG. 13C is a zoomed view of the rectangular box in FIG. 13B, showing (arrows) striated patterns of alpha-actinin. The scale bar is 200 micrometers in FIG. 13A and 20 micrometers in FIG. 13B.

Figure 14A:
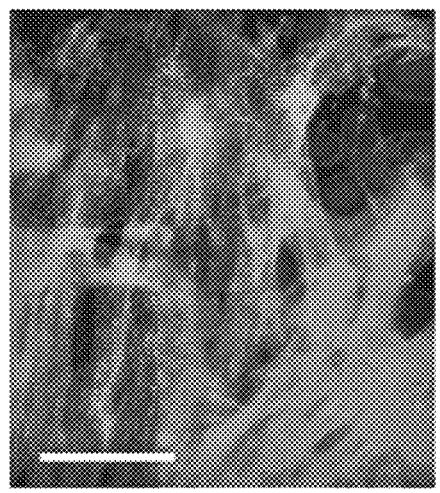
FIGS. 14A-14C illustrate epi-fluorescence images of cardiomyocytes growing on a cell scaffold in accordance with one embodiment of the invention.
Figure 14B:
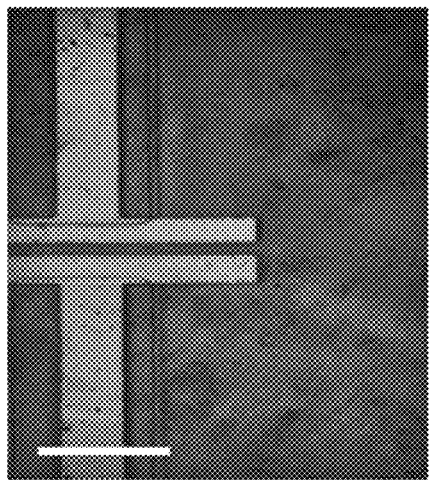
Figure 14C:

FIG. 14A shows an epi-fluorescence image of the cardiac patch highlighting alpha-actinin (stained with ALEXA FLUOR® 488) and cell nuclei (stained with Hoechst 34580) of cardiomyocytes. FIG. 14B shows a differential interference contrast (DIC) image of the same sample region, which highlights the S/D electrodes. FIG. 14C shows an overlay of both images to show the positions of S/D electrodes with respect to the cells (right). The scale bars is 40 micrometers.

Example 4

The monitoring capabilities of nanoES were demonstrated in an innervated 3D cardiomyocyte mesh construct (FIG. 10G). The output recorded from a single-nanowire FET (FIG. 10G) was about 200 micrometers below the construct surface showed regularly spaced spikes with a frequency of about 1 Hz, a calibrated potential change of about 2-3 mV, a signal/noise greater than or equal to 3 and a width of about 2 ms. The peak amplitude, shape, and width were consistent with extracellular recordings from cardiomyocytes. The potential of the nanoES cardiac patch to monitor appropriate pharmacological responsiveness (potentially constituting a platform for in vitro pharmacological studies) was also investigated by dosing it with norepinephrine, a drug that stimulates cardiac contraction via beta-1 ($\beta_1$) adrenergic receptors. Measurements from the same nanowire FET device showed a twofold increase in the contraction frequency following drug application. Interestingly, recordings from two nanowire FETs from the cardiac patch on noradrenaline application showed submillisecond and millisecond level, heterogeneous cellular responses to the drug (FIG. 15). Additionally, multiplexing measurements made with a reticular nanoES/neural construct (FIG. 16) showed that the 3D response of glutamate activation could be monitored. Together, these experiments show nanoES constructs can monitor in vitro the response to drugs from 3D tissue models, and thus can be used as a platform for in vitro pharmacological studies.

Simultaneous recordings from four nanowire FETs with separations up to 6.8 mm in a nanoES/cardiac construct (FIG. 10H) demonstrated multiplexed sensing of a coherently beating cardiac patch, with submillisecond time resolution. The device in this example yielded a relatively sparse device distribution with 60 devices over an area of about 3.5×1.5 $cm^2$. However, increases in nanowire FET density, the use of cross-bar circuits and implementing multiplexing/demultiplexing for addressing would allow the nanoES scaffolds to map cardiac and other synthetic tissue electrical activities over the entire construct at higher densities in three dimensions.

Figure 15A:
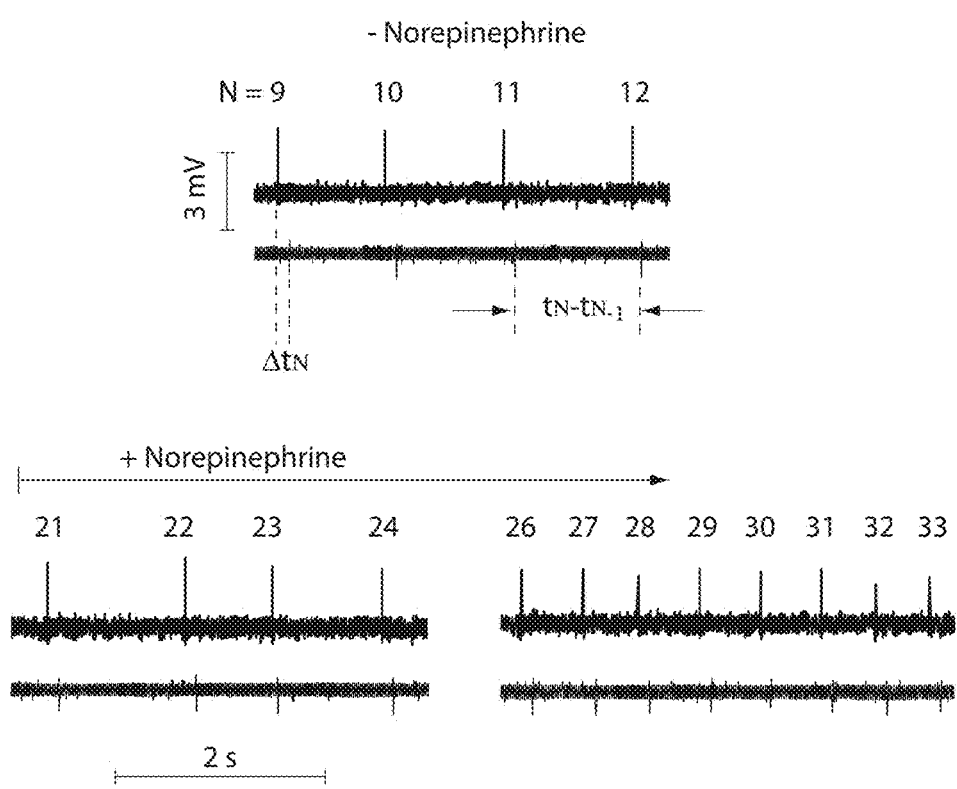
FIGS. 15A-15C illustrate multiplexed electrical recordings of cell scaffolds comprising nanoscale wires, in accordance with certain embodiments of the invention.
Figure 15B:
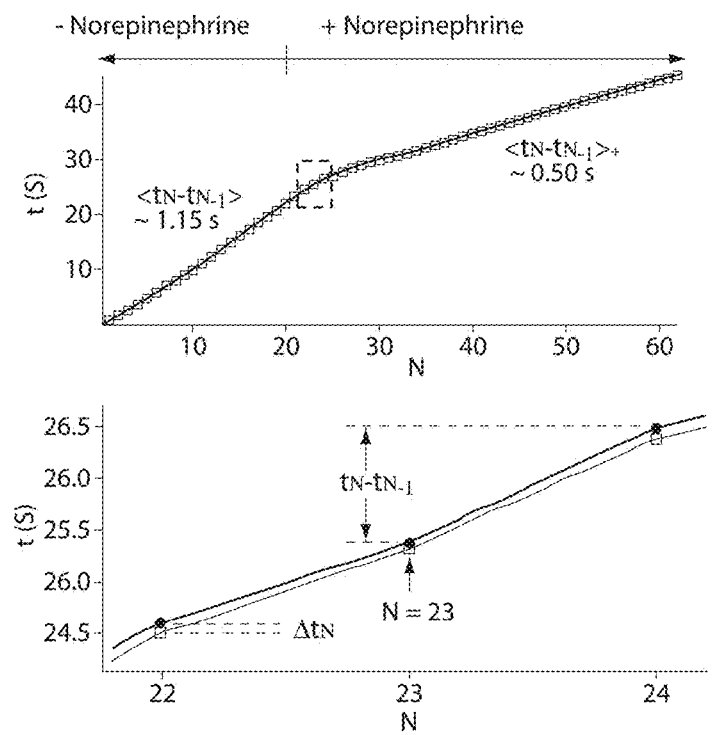
Figure 15C:
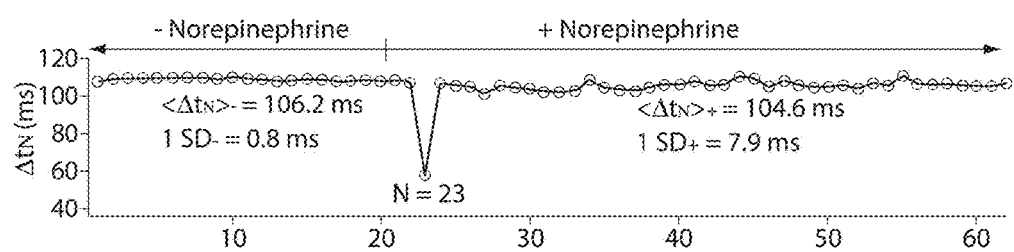
Figure 16A:
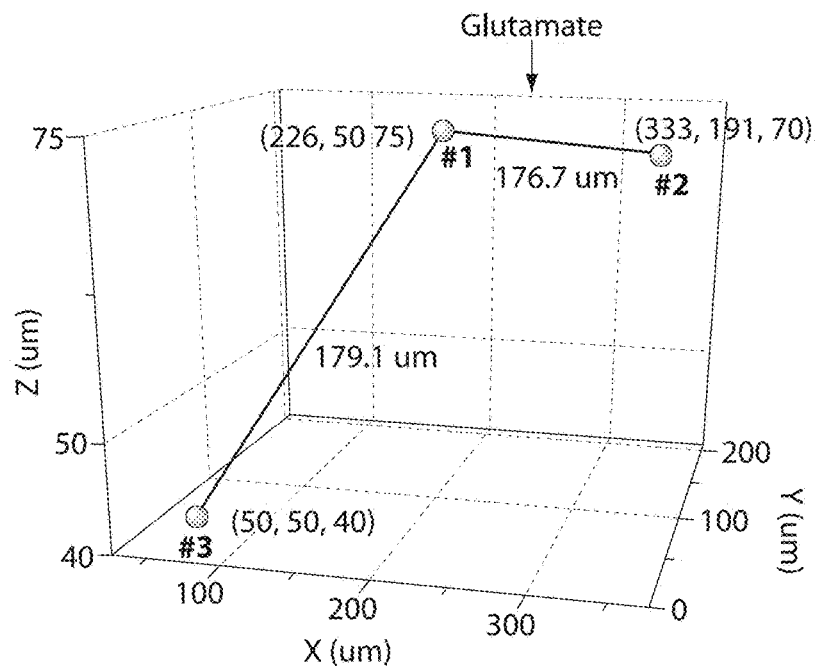
FIGS. 16A-16C illustrate multiplexed 3D electrical recordings of cell scaffolds comprising nanoscale wires, in accordance with certain embodiments of the invention.

FIG. 15A shows electrical recording traces from two devices in a cardiac patch, before (left), during (middle) and after (right) norepinephrine application. The temporal difference between a pair of spikes from two devices is denoted as delta-$t_N$ ($\Delta t_N$). The interval between consecutive spikes from a single device is denoted as $t_N$-$t_{N-1}$, where N is the spike index. FIG. 15B shows a time (t) versus spike index (N) plot, showing a change in slope after norepinephrine application. The slopes correspond to the time-averaged <$t_N$-$t_{N-1}$>, and are 1.15 seconds and 0.50 seconds before and after drug application, respectively. The data show that the cells exhibited overall coherent beating and response to the drug. The right panel is a zoom-in view of the transition, where the middle point (N=23) shows a decreased delta-$t_N$ ($\Delta t_N$) compared to earlier and later spikes. FIG. 15C shows a $\Delta t_N$ versus N plot. <$\Delta t_N$> and 1 SD (standard deviation) before (−) and after (+) norepinephrine application showed that although the drug has minimum effect on <$\Delta t_N$>, the sub-millisecond and millisecond fluctuations of delta-$t_N$ ($\Delta t_N$)(1 SD) increased by ~10 fold following drug addition. Such stochastic variation demonstrates millisecond-level, heterogeneous cellular responses to the drug.

Figure 16B:
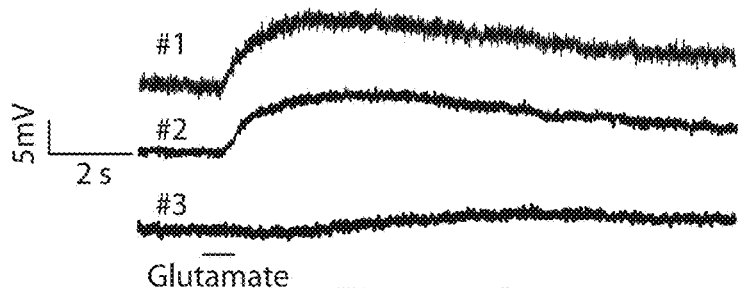
Figure 16C:
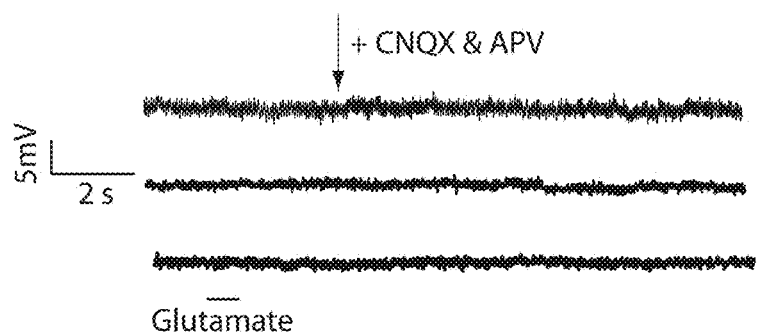

The hybrid nanoES/neural 3D construct was prepared by culturing neurons with a 3D reticular device array for 14 days in vitro with a density of >4 million neurons/mL in MATRIGEL™. During recording, the nanoES/neural hybrid was perfused with an oxygenated artificial CSF (aCSF) containing (in mM) 119 NaCl, 2.5 KCl, 2.5 $CaCl_2$), 1.3 $MgSO_4$, 1 $NaH_2PO_4$, 26.2 $NaHCO_3$, 22 glucose and equilibrated with 95% $O_2$/5% $CO_2$. Three nanowire FETs (labeled 1, 2, and 3) were distributed in the construct with x-y-z positions shown in FIG. 16A. The total sample thickness was about 100 micrometers. The lines indicate the distances between two devices in 3D. Sodium glutamate was dissolved in saline solution and further diluted to 20 mM in aCSF solution. Glutamate solution was injected in the middle above device 1 and 2 (arrow). The injection pulse duration is 0.5 s. FIG. 16B shows the local field potential changes recorded from three devices in the 3D neuron construct, showing distinct position-dependent temporal responses following glutamate solution injection. FIG. 16C shows that perfusing 6-cyano-7-nitroquinoxaline-2,3-dione (CNQX) and D(−)-2-amino-5-phosphonopentanoic acid (APV) blockers prior to glutamate addition eliminated any observed response, and thus showed that the observed response in FIG. 16B could be attributed to postsynaptic signal propagation. The segments above "Glutamate" mark the timing when glutamate solution was injected (FIGS. 16B-16C)

Example 5

Figure 17A:
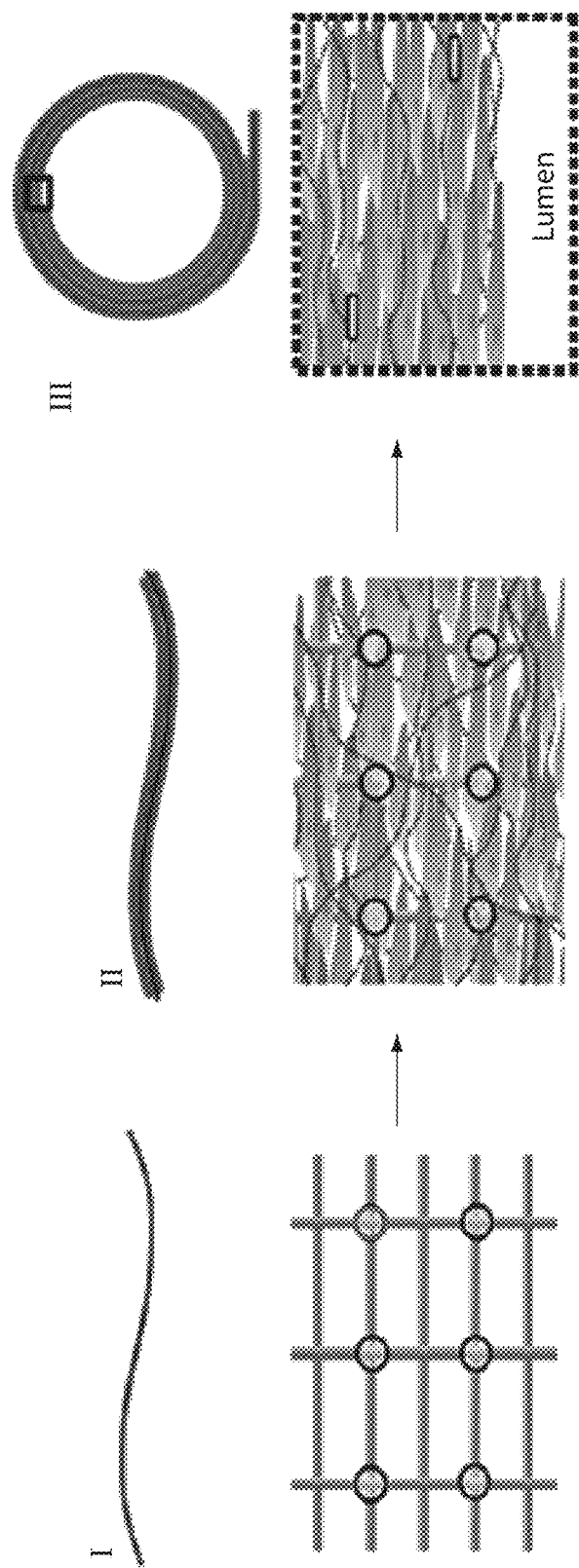
FIGS. 17A-17F illustrate a cell scaffold used as a vascular construct, in accordance with another embodiment of the invention.
Figure 17B:
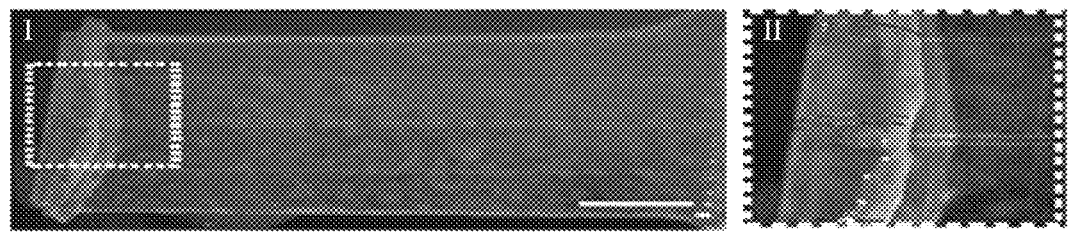
Figure 17C:
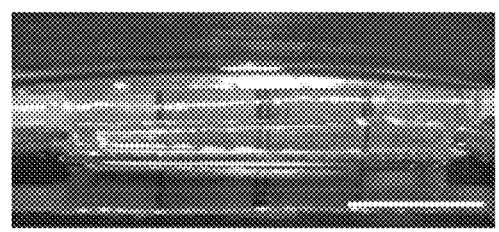
Figure 19:
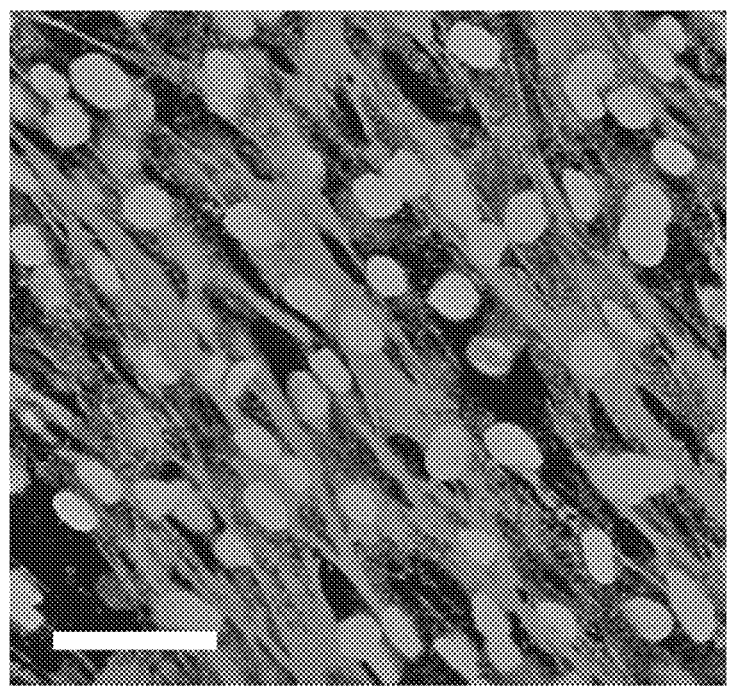
FIG. 19 illustrates a confocal fluorescence image of smooth muscle cells in a cell scaffold, in another embodiment of the invention.

This example illustrates the development of artificial tissue with embedded nanoelectronic sensory capabilities. Vascular nanoES constructs were made by processes analogous to those used for tissue engineered autologous blood vessels except for the addition of the nanoES (FIGS. 17A and -18). In this example, human aortic smooth muscle cells (HASMCs) were cultured on 2D mesh nanoES with sodium ascorbate to promote deposition of natural ECM. The hybrid sheets (FIG. 17B) were rolled into multi-layer 3D tubular structures and matured (see below) without macroscopic or desquamation (FIG. 17C). Cells in the construct expressed smooth muscle alpha-actin (by immunostaining), the key contractile protein in smooth muscle (FIG. 19).

Figure 17D:
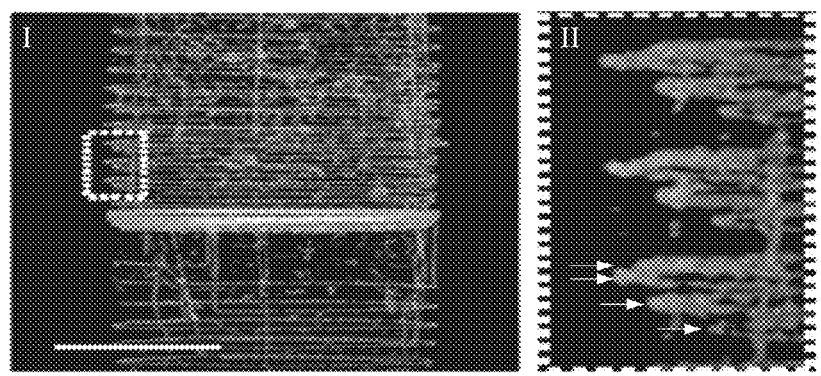
Figure 17E:
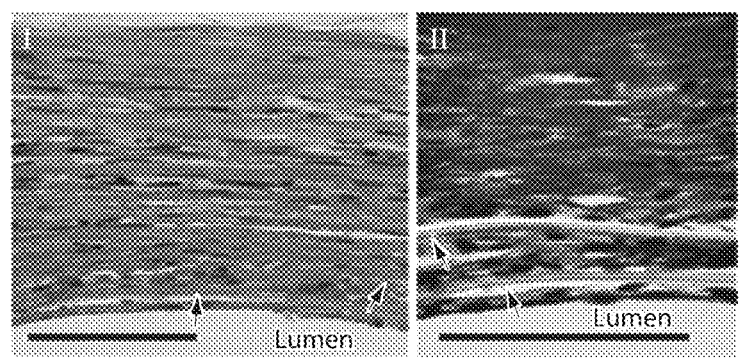

The distribution of nanoES in the tubular construct was visualized by micro-computed tomography (μCT). A top-down projection of reconstructed 3D micro-computed tomography data (FIG. 17D) revealed regularly spaced metal interconnects with at least four revolutions (arrows in FIG. 17D, Panel II), consistent with the NWFET mesh design and tissue rolling technique. Analyses of hematoxylineosin-stained sections (FIG. 17E) revealed well-defined smooth muscle tissue about 200 micrometers thick, with elongated cells and collagenous nanofibers, and embedded SU-8 ribbons from the nanoES (FIG. 17E). These findings confirm 3D integration of NWFET nanoelectronics with healthy smooth muscle.

Figure 17F:
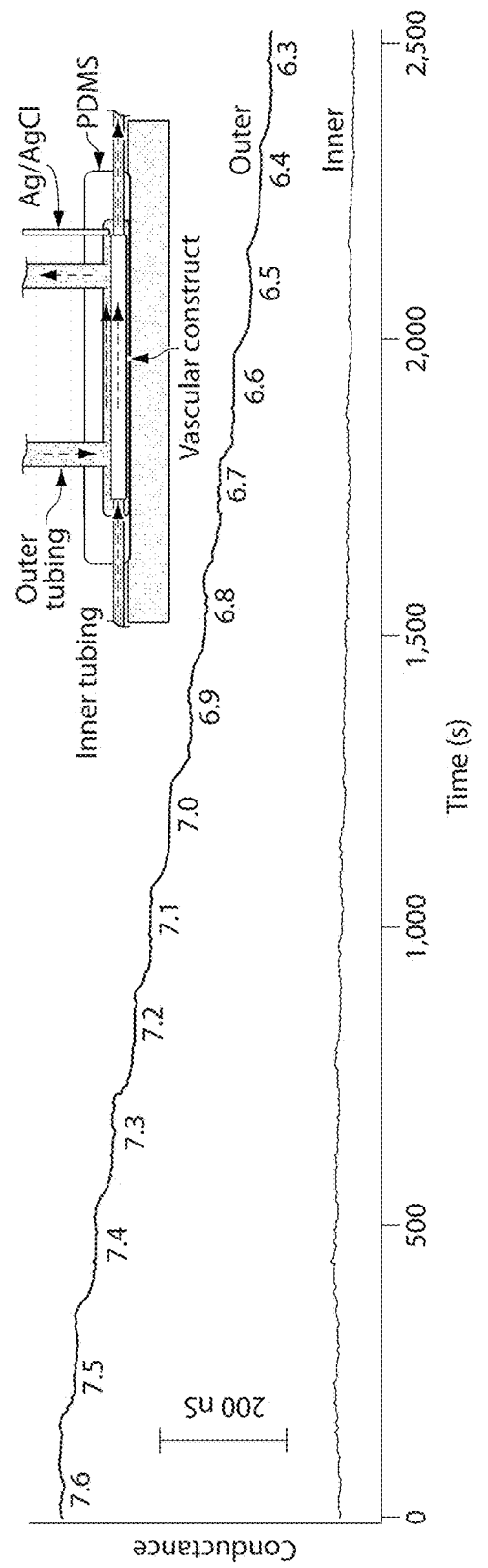

The potential of nanoES to function as a biomedical device, was demonstrated in the pH sensing capability of nanoES/HASMC vascular construct (FIG. 17F, inset). As the extravascular pH was varied stepwise with luminal pH fixed, simultaneous recordings from NWFETs in the outermost layer showed stepwise conductance decreases with a sensitivity of ~32 mV/pH. NWFETs in the innermost layer (closest to luminal) showed minor baseline fluctuations. This ability to resolve extravascular pH changes suggests the possibility of detecting inflammation, ischemia and tumor microenvironments or other forms of metabolic acidosis, e.g., due to overproduction of organic acids or impaired renal acidification. Other markers of disease could potentially be detected by the nanoES.

Additional details regarding FIG. 17 follow. FIG. 17A shows a schematic of the synthesis of smooth muscle nanoES. The upper panels are side views, while the lower ones are either top views (Panels I and II) or a zoom-in view (Panel III). The dots are NWFETs. Panel I shows a mesh nanoES with NWFETs, while Panels II and III show the structure with HASMCs and collagenous matrix secreted by the HASMC. FIG. 17B, Panel I shows a photograph of a single HASMC sheet cultured with sodium L-ascorbate on a nanoES. Panel II shows a zoomed-in view of the dashed area in Panel I, showing metallic interconnects macroscopically integrated with cellular sheet. FIG. 17C is a photograph of the vascular construct after rolling into a tube and maturation in a culture chamber for 3 weeks. FIG. 17D, Panel I is a microcomputed tomography of a tubular construct segment. Panel II is a zoomed-in view of Panel I. Arrows mark the individual NWFET-containing layers of the rolled construct. The scale bar is 1 mm. FIG. 6E shows hematoxylin & eosin (Panel I) and masson trichrome (Panel II, with collagen) stained sections (about 6 micrometers thick) cut perpendicular to the tube axis; lumen regions are labeled. The arrows mark the positions of SU-8 ribbons of the nanoES. Scale bars are 50 micrometers. FIG. 17F shows changes in conductance over time for two NWFET devices located in the outermost and innermost layers. The inset is a schematic of the experimental set-up. Outer tubing delivered bathing solutions with varying pH (dashed lines and arrows); inner tubing delivered solutions with fixed pH (dashed lines and arrows).

FIG. 19 is a confocal fluorescence microscopy image from the surface of the HASMC/mesh-like nanoelectronics biomaterial. In the image, alpha-actin in the smooth muscle cell was stained with ALEXA FLUOR® 488 and the cell nuclei (round) were stained with Hoechst 34580. Local alignment of HASMCs is revealed by anisotropy in alpha-actin fibers running from upper left to lower right of image. The scale bars is 40 micrometers.

Example 4

This example describes various methods used in Examples 1-3.

Methods Summary. Kinked and uniform silicon nanowires were synthesized by nanocluster-catalyzed methods. See, e.g., U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; U.S. Pat. No. 7,301,199, issued Nov. 27, 2007, entitled "Nano scale Wires and Related Devices," by Lieber, et al.; and International Patent Application No. PCT/US2010/050199, filed Sep. 24, 2010, entitled "Bent Nanowires and Related Probing of Species," by Tian, et al., published as WO 2011/038228 on Mar. 31, 2011, each incorporated herein by reference in its entirety. The devices were fabricated on silicon substrates (Nova Electronic Materials, n-type 0.005 V cm) with 600 nm $SiO_2$ or 100 $SiO_{2/200}$ $Si_3N_4$ at the surface. Electron beam lithography and photolithography on nickel relief layers were used to define the metal contacts to the nanowires and the key features of the scaffolds.

Steps used in the fabrication of the reticular nanoES included the following. First, 100 nm nickel metal was patterned and deposited, and served as the relief layer for the free-standing scaffolds. Next, a 300-500 nm layer of SU-8 photoresist (2000.5, MicroChem, Newton) was deposited over the entire chip (FIG. 20C), followed by pre-baking at 65° C. and 95° C. for 2 and 4 min, respectively; then an isopropanol solution of $n^+$-n-$n^+$ kinked nanowires was deposited onto the SU-8 layer. After identifying nanowire positions by optical imaging (Olympus BX51) and designing the interconnect and SU-8 patterns in IGOR Pro (WaveMetrics) and DesignCAD, EBL was used to pattern the overall SU-8 scaffold structure around chosen nanowires, which was post-baked (65° C. and 95° C. for 2 and 4 min, respectively) and cured (180° C., 20 min) to yield the flexible structural support for metal interconnects. The silicon substrate was then coated with a methyl methacrylate and poly(methyl methacrylate) double-layer resist, the resist was patterned over the chosen SU-8 ribbons and then non-symmetrical Cr/Pd/Cr (1.5/50-80/50-80 nm) metals were sequentially deposited followed by metal lift-off in acetone to form the nanowire interconnects. The non-symmetrical Cr/Pd/Cr layer structure yielded a built-in stress, which drove 3D self-organization when the structure was relieved from the substrate.

The silicon substrate was then coated with a uniform 300-400 nm layer of SU-8, and EBL of SU-8 followed by curing (180° C., 20 min) was used to define the SU-8 passivation layer over the deposited metal interconnects. The reticular nanoES, including the interconnected kinked nanowire FET devices, was released from the substrate by etching of the nickel layer (Nickel Etchant TFB, Transene Company, Danvers) for 60-120 min at 25° C. Last, the free-standing nanoES was dried using a critical point dryer (Autosamdri 815 Series A, Tousimis) and stored in a dry state before use in tissue culture. Each EBL step took about 10 min-2 hours, depending on factors such as the writing speed and area, feature size and complexity, and electron beam dosage (for example, the typical area dosages for SU-8 and poly(methyl methacrylate) EBL was 3-8 microC $cm^{-2}$ and 500-1,000 microC $cm^{-2}$ at 25 kV, respectively). The entire fabrication took 2-5 days, depending on the duration of the individual steps. A similar approach was used in the fabrication of the mesh nanoES except that p-type nanowires and photolithography were used and the entire process took 2-3 days.

NanoES/collagen (MATRIGEL™) hybrid matrices were made by casting 50~2,000 microliters collagen or MATRIGEL™ solution onto the edge of (reticular nanoES) or directly above (mesh nanoES) the nanoES scaffolds, and at ~4° C. The solutions were allowed to form gels around nanoES under conditions of 37° C. and 5% $CO_2$ for at least 20 min. The 3D nanoES/alginate scaffolds were prepared from pharmaceutical-grade alginate (Protanal LF5/60, FMC Biopolymers) by calcium gluconate crosslinking and subsequent lyophilization to produce a sponge-like scaffold (5-15 mm×2-10 mm, d×h). To prepare NanoES/PLGA hybrid scaffolds, a sheet of PLGA fibres with diameters of ~1-3 micrometers was deposited on both sides of the mesh nanoES. The hybrid scaffold could also be folded to increase the thickness.

Embryonic Sprague/Dawley rat hippocampal cells, neonatal Sprague/Dawley rat cardiomycytes and human aortic smooth muscle cells were cultured in nanoES using established protocols. Optical micrographs of immunohistochemically and histologically stained samples were recorded using either Olympus Fluoview FV1000 or Olympus FSX100 systems. The structures of nanoES were characterized with Zeiss Ultra55/Supra55VP field-emission SEMs or the HMXST Micro-computed tomography x-ray imaging system (model: HMXST225, X-Tek). The in vitro cytotoxicity of nanoES was evaluated using the standard LIVE/DEAD® Viability/Cytotoxicity Kit (Molecular Probes, Invitrogen) and the CELLTITER 96® AQueous One Solution Cell Proliferation Assay (Promega Corporation). Cardiomyocyte recordings were carried out in Tyrode solution with a 100 mV DC source for the NWFETs. The current was amplified with a multi-channel preamplifier, filtered with a 3 kHz low pass filter (CyberAmp 380), and digitized at a 50 kHz sampling rate (Axon Digi1440A).

In extravascular pH sensing experiments, a single polydimethylsiloxane (PDMS) microfluidic chamber was used to deliver two flows of phosphate buffer solutions, where inner and outer tubings were used to deliver solutions with fixed and varied pH, respectively. The electrical measurements were conducted using a lock-in amplifier with a modulation frequency of 79 and 39 Hz, time constant of 30 ms, amplitude of 30 mV; the DC source-drain potential was zero. Ag/AgCl reference electrodes were used in all recording and sensing experiments. The calibrated potential values (in millivolts) recorded from nanowire FETs were obtained as the ratios between device conductance changes (in nanosiemens) and the sensitivities (in microsiemens per volt or nanosiemens per volt) that were determined individually in water-gate experiments.

Nanowire Synthesis. Single-crystalline nanowires were synthesized using the Au nanoclustercatalyzed vapor-liquid-solid growth mechanism in a home-built chemical vapor (CVD) deposition system. Au nanoclusters (Ted Pella Inc., Redding, Calif.) with either 20 or 80 nm diameters were dispersed on the oxide surface of silicon/$SiO_2$ substrates (600 nm oxide) and placed in the central region of a quartz tube CVD reactor system. Uniform 20 nm p-type silicon nanowires, which were used for mesh-like NWFET scaffolds, were synthesized using established methods. See, e.g., U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; and U.S. Pat.

No. 7,301,199, issued Nov. 27, 2007, entitled "Nanoscale Wires and Related Devices," by Lieber, et al., each incorporated herein by reference in its entirety. In a typical synthesis, the total pressure was 40 torr and the flow rates of $SiH_4$, $B_2H_6$ (100 ppm in $H_2$) and $H_2$ were 2, 2.5 and 60 standard cubic centimeters per minute (SCCM), respectively. The silicon-boron feed-in ratio was 4000:1, and the total nanowire growth time was 30 min.

Kinked 80 nm diameter silicon nanowires, which were used for the reticular NWFET scaffolds, were synthesized with a $n^+$(arm)-n(device)-$n^+$(arm) dopant profile. See, e.g., International Patent Application No. PCT/US2010/050199, filed Sep. 24, 2010, entitled "Bent Nanowires and Related Probing of Species," by Tian, et al., published as WO 2011/038228 on Mar. 31, 2011, incorporated herein by reference in its entirety. In a typical synthesis, the total pressure was 40 torr and the flow rates of $SiH_4$, $PH_3$ (1000 ppm in $H_2$) and $H_2$ were 1, 5/0.1 and 60 sccm, respectively. Kinks were introduced by evacuation of the reactor (~3× $10^{-3}$ torr) for 15 s, and the silicon-phosphorus feed-in ratios were 200:1 and 10,000:1 for the $n^+$- and n-type segments, respectively. The $n^+$-type arms were grown for 12-15 min, and the n-type active device channel segment was grown for 30 s immediately following the evacuation step used to introduce a kink.

Free-standing nanoES. The free-standing nanoES were fabricated on the oxide or nitride surfaces of silicon substrates (600 nm $SiO_2$ or 100 $SiO_2$/200 $Si_3N_4$, n-type 0.005 V cm, Nova Electronic Materials, Flower Mound, Tex.) prior to relief from the substrate. Two basic types of nanoES, termed reticular and mesh nanoES, were prepared. Components include silicon wafer (105 in FIG. 7), nickel relief layer (110), polymer ribbons (115), silicon nanowires (120), and metal interconnects (125). In a typical experiment, the widths of polymer and metal interconnects were 1 and 0.7 micrometers, respectively. The built-in stress from sequentially deposited Cr/Pd/Cr (1.5/50-80/50-80 nm) layers drove self-organization into a 3D scaffold after the lift-off process. Key steps used in the fabrication of the reticular nanoES (FIG. 20) were as follows: (1) Electron beam lithography (EBL) was used to pattern a double layer resist of 500-600 nm of methyl methacrylate (MMA, MicroChem Corp., Newton, Mass.) and 100-200 nm of poly(methyl methacrylate) (PMMA, MicroChem Corp., Newton, Mass.), on which 100 nm nickel metal was deposited (FIGS. 20A-7B), where the nickel served as the final relief layer for the free-standing scaffolds. (2) A 300-500 nm layer of SU-8 photoresist (2000.5, MicroChem Corp., Newton, Mass.) was deposited over the entire chip (FIG. 20C) followed by pre-baking at 65° C. and 95° C. for 2 and 4 min, respectively, then (3) an isopropanol solution of $n^+$n-$n^+$ kinked nanowires was dropped onto the SU-8 layer and allowed to evaporate (FIG. 20D). (4) The kinked nanowire positions were located relative to a standard marker pattern S4 using an optical microscope (Olympus BX51) in dark-field mode, and then IGOR Pro (WaveMetrics) and DesignCAD were used to design the lithography patterns. EBL was then used to pattern the overall SU-8 scaffold structure including a ring structure underneath the selected kink nanowire. After postbaking (65° C. and 95° C. for 2 and 4 min, respectively), the SU-8 developer (MicroChem Corp., Newton, Mass.) was used to develop the SU-8 pattern. The areas exposed to electron beam became fully polymerized and insoluble in SU-8 developer, which 'glued' the selected nanowires in place. The rest of the SU-8 areas, including nanowires on their surfaces, were removed by SU-8 developer. After curing (180° C., 20 min), patterned SU-8 ribbons as flexible structural support for metal interconnects and nanowires were generated (FIG. 20E). (5) The silicon substrate was then coated with MMA and PMMA double layer resist, the resist was patterned over the chosen SU-8 ribbons, and then nonsymmetrical Cr/Pd/Cr (1.5/50-80/50-80 nm) metals were sequentially deposited followed by metal lift-off in acetone to form the nanowire interconnects (FIG. 20F). The nonsymmetrical Cr/Pd/Cr layer structure yielded a built-in stress, which drove 3D self-organization when the structure was relieved from the substrate. (6) The silicon substrate was then coated with a uniform 300-400 nm layer of SU-8, and EBL of SU-8 followed by curing (180° C., 20 min) was used to define the SU-8 passivation layer over the deposited metal interconnects (FIG. 20G). (7) The reticular nanoES, including the interconnected kinked NWFET devices, was released from the substrate by etching of the nickel layer (Nickel Etchant TFB, Transene Company Inc., Danvers, Mass.) for 60-120 min at 25° C. (FIG. 20H). Last, the free-standing nanoES were dried using a critical point dryer (Autosamdri 815 Series A, Tousimis, Rockville, Md.) and stored in the dry state prior to use in tissue culture. Here, self-organization produced random reticular scaffolds, but it should be noted that mechanics models and simulations (e.g., finite element method) could be used to design and realize regular three-dimensional (3D) open framework constructs using the same approach.

A similar approach was used in the fabrication of the mesh nanoES (FIG. 21): (1) Photolithography and metal deposition (100 nm, nickel) were used to define a relief layer for the free-standing scaffold (FIGS. 21A, 21B). (2) A layer of SU-8 photoresist (300-2000 nm, 2000.5 or 2002, MicroChem Corp., Newton, Mass.) was deposited over the entire chip, and photolithography was used to pattern the bottom SU-8 mesh structure (FIG. 21C), which was then cured (180° C., 20 min). (3) A second 300-500 nm thick layer of SU-8 was deposited over the entire chip, and prebaked at 65° C. and 95° C. for 2 and 4 min, respectively (FIG. 21D). (4) Then p-type silicon nanowires were deposited from isopropanol solution and aligned by nitrogen blow-drying (FIG. 21E). (5) Photolithography and subsequent curing (180° C., 20 min) was used to define the nanowire patterns across the mesh structure and eliminate excess nanowires (FIG. 21F). (6) The substrate was coated with S1805 and LOR 3A (MicroChem Corp., Newton, Mass.) double layer resist and patterned by photolithography. Symmetrical Cr/Pd/Cr (1.5/50-100/1.5 nm) metals were sequentially deposited followed by metal lift-off in Remover PG (MicroChem Corp., Newton, Mass.) to define the minimally stressed nanowire interconnects (FIG. 21G). (7) The substrate was coated with a uniform layer of SU-8, and photolithography followed by curing (180° C., 20 min) was used to define a passivation layer over the deposited metal interconnects (FIG. 21H). (8) The mesh-like nanoES was released from the substrate by etching the nickel layer (Nickel Etchant TFB, Transene Company Inc., Danvers, Mass.) for 6 h at 25° C. (FIG. 21I). The mesh-like scaffold adhered weakly to the substrate upon drying in air, and could be readily suspended as a freestanding scaffold upon immersion in water/cell culture medium. Scanning electron microscopy (SEM, Zeiss Ultra55/Supra55VP field-emission SEMs) was used to characterize both types of fabricated scaffold structures.

NanoES/collagen (MATRIGEL™) hybrid matrix. Prior to gel casting, collagen type-I (Sigma-Aldrich Corp., St. Louis, Mo.) was diluted (1:2~1:5) with culture media or phosphate buffered saline solution (PBS) and the pH was adjusted to ~7.4. MATRIGEL™ (BD Bioscience, Bedford, Mass.) was used as received or diluted (1:2~1:5). Briefly, 50~2000 microliters collagen or MATRIGEL™ solution was placed using a pipette (Eppendorf Research plus) onto the edge of (reticular nanoES) or directly above (mesh nanoES) the nanoES scaffolds, and at ~4° C. The solutions were allowed to form gels around nanoES under 37° C., 5% $CO_2$ conditions for at least 20 min. For visualization of collagen fibers, fluorescein isothiocyanate labeled collagen type-I (Sigma-Aldrich Corp., St. Louis, Mo.) was used.

NanoES/alginate hybrid scaffold. The 3D nanoES/alginate scaffolds were prepared from pharmaceutical-grade alginate, Protanal LF5/60 (FMC Biopolymers), which has a high guluronic acid (G) content (65%). Briefly, (1) preparation of sodium alginate stock solutions at concentrations of 1% (w/v); (2) partially crosslinking the alginate solution by adding calcium gluconate; (3) drop casting partially crosslinked alginate onto loosely folded mesh nanoES, followed by additional shaping and placement of nanoES inside the alginate gel with a glass rod; (4) freezing the nanoES/alginate gel in a homogeneous, cold (−20° C.) environment; and (5) lyophilization to produce a sponge like scaffold (5~15 mm×2~10 mm, d×h).

NanoES/PLGA hybrid scaffold. Poly(lactic-co-glycolic acid) (PLGA) electrospun fibers were used as a secondary scaffold in several experiments. The PLGA fibers were prepared based on typical procedures as follows. PLGA (90/10 glycolide/L-lactide, inherent viscosity 1.71 dL/g in HFIP at 25° C., Purac Biomaterials Inc.) was dissolved in 1,1,1,3,3,3-hexafluoro-2-propanol (HFIP, Sigma-Aldrich Corp., St. Louis, Mo.) at a 10 wt % concentration until a clear and homogenous solution was obtained. A syringe pump (Harvard Apparatus, Holliston, Mass.) was used to deliver the polymer solution through a stainless steel capillary at a rate of 3 mL/hr. A high voltage power supply (Gamma High Voltage Research, Ormond Beach, Fla.) was used to apply a 25 kV potential between the capillary tip and a grounded stainless steel plate 50 cm away. Fibers were collected for 2-5 minutes before being put aside at room temperature for 72 hours to allow residual solvent evaporate. To prepare hybrid scaffolds, a sheet of PLGA fibers with diameters of ~1-3 micrometers was deposited on both sides of the mesh nanoES. The hybrid scaffold could also be folded to increase its thickness.

Scaffold mechanical properties. The effective bending stiffness per unit width of the mesh scaffold, $\overline{D}$, can be estimated by:

$$\overline{D} = \alpha_s D_s + \alpha_m D_m,$$

where $\alpha_s$ and $\alpha_m$ are the area fraction of the single-layer polymer (SU-8) ribbon (without metal layer and top polymer passivation layer) and three-layer ribbon (bottom polymer layer, metal layer and top passivation layer) in the whole mesh structure. $D_s = E_s h^3/12$ is the bending stiffness per unit width of the single-layer polymer, where $E_s = 2$ GPa and h are the modulus and thickness of the SU-8. $D_m$ is the bending stiffness per unit width of a three-layer structure, which can be calculated by:

$$D_m = \frac{E_m b_m h_m^3}{12b} + \frac{E_s}{b}\left(\frac{(b-b_m)(2h+h_m)^3}{12} + \frac{1}{6}b_m h^3 + 2b_m h\left(\frac{h}{2} + \frac{h_m}{2}\right)^2\right),$$

where $E_m = 121$ GPa and $h_m$ are the modulus and thickness of the palladium, b is the width of the single-layer ribbon and the total width of the three-layer ribbon, $b_m$ is the width of the palladium layer. In addition, the chromium layers are so thin (1.5 nm) that their contribution to the bending stiffness is negligible. When $h_m = 75$ nm, h=0.5 micrometers, b=10 micrometers, $b_m = 5$ micrometers, $\alpha_s = 2.51\%$ and $\alpha_m = 3.57\%$, $\overline{D} = 0.006$ nN m. When $h_m = 75$ nanometers, h=2 micrometers, b=40 micrometers, $b_m = 20$ micrometers, $\alpha_s = 10.06\%$ and $\alpha_m = 13.31\%$, D=1.312 nN m.

To calculate the strain in tubular constructs, the equation $\varepsilon = y/R$ was used, where y is the distance from the neutral plane, and R is the radius of curvature. For the symmetric mesh scaffold, since the neutral plane is the middle plane, the maximum strains of metal and SU-8 appear at $y = h_m/2$ and $Y = h_m/2 + h$ respectively. When $h_m = 75$ nm, h=2 micrometers, R=0.75 mm, the maximum strains of metal and SU-8 are 0.005% and 0.272%, respectively.

Scaffold structural simulation. The self-organization of the mesh structure due to residual stress was simulated by the commercial finite element software ABAQUS. Both the SU-8 ribbons and the SU-8/metal ribbons were modeled as beam elements. The cross-sectional property of the SU-8/metal ribbons was defined by the appropriate meshed beam cross-section, while the cross-sectional property of the SU-8 ribbons was set by defining the relevant rectangular profile. The equivalent bending moment on SU-8/metal ribbons was calculated using the residual stress measured by MET-1 FLX-2320-S thin film stress measurement system, which were 1.35 and 0.12 GPa for Cr (50 nm) and Pd (75 nm), respectively.

Figure 9A:
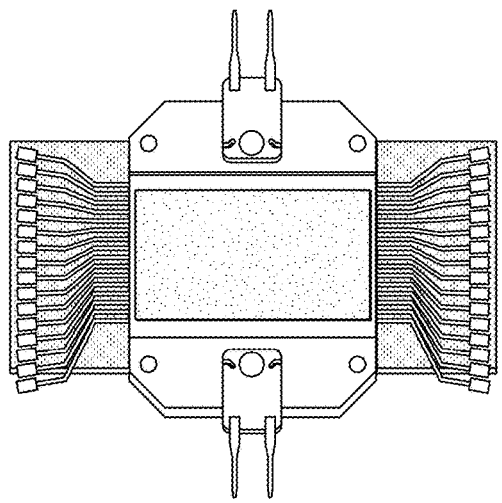
FIG. 9A-9D illustrate 3-dimensional culturing of neuronal cells in a cell scaffold, in another embodiment of the invention.
Figure 9B:
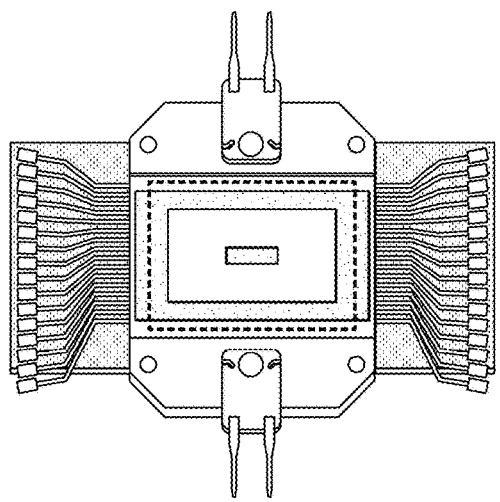
Figure 9C:
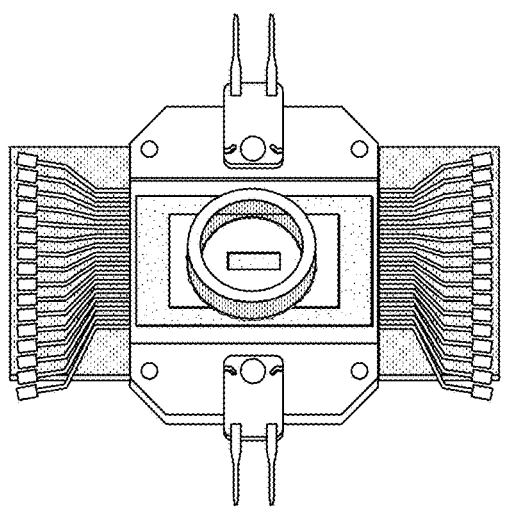
Figure 9D:
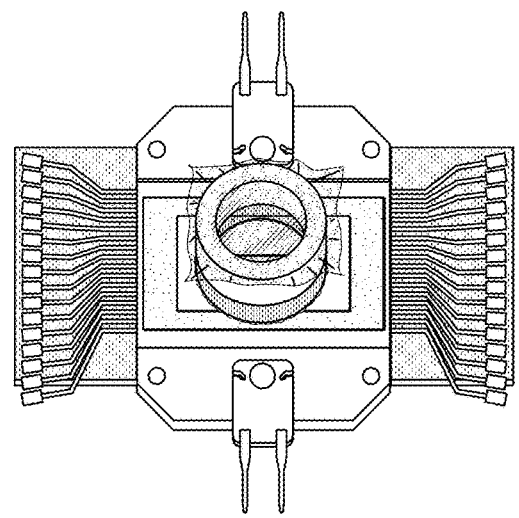

Neuron culture. Device chips were cleaned by oxygen plasma (50 sccm of $O_2$, 50 w, 0.5 Torr, 1 min), and fixed onto a temperature controlled chamber (Warner Instruments, Hamden, Conn.) with double-sided tape (FIG. 9A). A 1 mm thick polydimethylsiloxane (PDMS) membrane (Sylgard 184, Dow Corning, Inc., Midland, Mich.) with 0.25 $cm^2$ open area in the center was cut, autoclaved and placed over the device area, followed by wire-bonding of individual devices. An autoclaved glass ring (ALA Scientific Instruments, Farmingdale, N.Y.) was placed over this PDMS chamber and fixed with Kwik-Sil (World Precision Instruments, Inc., Sarasota, Fla.) silicone elastomer (FIG. 9C). The whole chip was sterilized by UV illumination and 75% ethanol soak (20 min each). An aqueous polylysine solution (0.5-1.0 mg/ml, MW 70,000 to 150,000, Sigma-Aldrich) was then introduced into the chamber and incubated overnight at 37° C., the polylysine solution was removed, and the chamber rinsed 3 times each with 1× phosphate buffered saline (PBS) solution and NeuroPure Plating Medium (Genlantis, San Diego, Calif.). Finally, the chamber was filled with NeuroPure Plating Medium or culture medium and conditioned in the incubator for 1 day. Hippocampal neurons (Gelantis, CA) were prepared using standard protocols. In brief, 5 mg of NeuroPapain Enzyme (Gelantis, CA) was added to 1.5 ml of NeuroPrep Medium (Gelantis, San Diego, Calif.). The solution was kept at 37° C. for 15 min, and sterilized with a 0.2 micrometer syringe filter (Pall Corporation, MI). Day 18 embryonic Sprague/Dawley rat hippocampal tissue with shipping medium (E18 Primary Rat Hippocampal Cells, Gelantis, San Diego, Calif.) was spun down at 200 g for 1 min. The shipping medium was exchanged for NeuroPapain Enzyme medium. A tube containing tissue and the digestion medium was kept at 30° C. for 30 min and manually swirled every 2 min, the cells were spun down at 200 g for 1 min, the NeuroPapain medium was removed, and 1 ml of shipping medium was added. After trituration, cells were isolated by centrifugation at 200 g for 1 min, then re-suspended in 5 to 10 mg/ml MATRIGEL™ (BD Bioscience, Bedford, Mass.) at 4° C. The cell/MATRIGEL™ mixture was plated on the reticular nanoES in the opening in the PDMS membrane at a density of 2 to 4 million cells/ml and a total gel thickness of ~0.5 to 1 mm. The MATRIGEL™ matrix was allowed to gel at 37° C. for 20 min, then 1.5 ml of NeuroPure Plating Medium was added, and the entire assembly was placed in the incubator. After 1 day, the plating medium was changed to NEUROBASAL™ medium (Invitrogen, Grand Island, N.Y.) supplemented with B27 (B27 Serum-Free Supplement, Invitrogen, Grand Island, N.Y.), GLUTAMAX™ (Invitrogen, Grand Island, N.Y.) and 0.1% Gentamicin reagent solution (Invitrogen, Grand Island, N.Y.). 3D neuron cultures were maintained at 37° C. with 5% $CO_2$ for 7 to 21 days, with medium changed every 4 to 6 days. For cultures lasting longer than 7 days, gas-permeable/water-impermeable membrane covers (ALA MEA-MEM-PL, ALA Scientific Instruments, Farmingdale, N.Y.) were used to avoid evaporation while allowing for diffusion of gases (FIG. 9D).

Cardiomyocyte culture. Hybrid scaffolds (see FIG. 12B) of the mesh nanoES (FIGS. 12A and 12G) sandwiched between two electrospun PLGA fiber layers (1-3 micrometers diameter; 10-20 micrometers thick for individual layer) were used in all experiments. The bottom PLGA layer was made either by inserting an existing layer underneath the mesh-like scaffold or by directly electrospinning on the nanoES. The top PLGA layer was made by direct electrospinning on the nanoES.

Figure 12A:
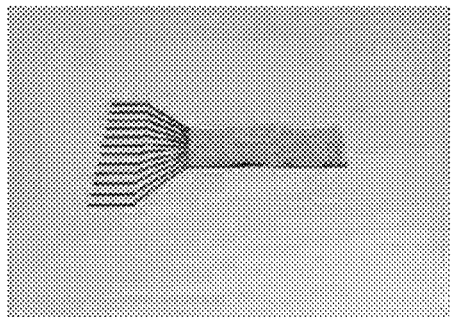
FIGS. 12A-12H illustrate 3-dimensional culturing of cardiomyocytes in a cell scaffold, in another embodiment of the invention.
Figure 12B:
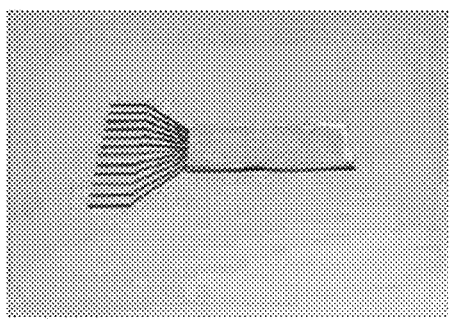
Figure 12C:
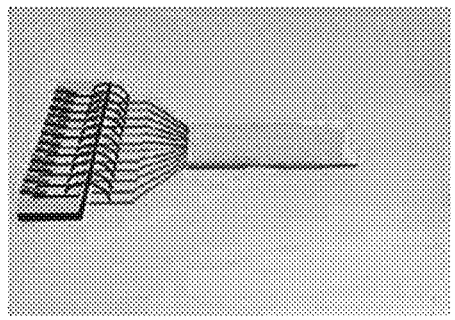
Figure 12D:
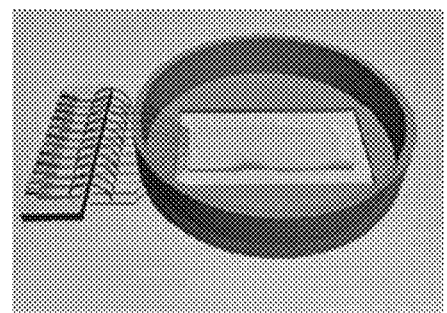

The device chip was wire-bonded (FIGS. 12C and 12H), and assembled with a modified polystyrene petri-dish (VWR Inc.) using Kwik-Sil (World Precision Instruments, Inc.) silicone elastomer glue (FIG. 12D). The device chamber was cleaned by oxygen plasma (50 sccm of $O_2$, 50 w, 0.5 Torr, 1 min), followed by sterilization with UV-light illumination for 1 h and soaking in 70% ethanol solution for 0.5 h. The hybrid scaffolds were coated with fibronectin/gelatin solution overnight prior to cell seeding. The fibronectin/gelatin solution was prepared by adding 0.1 g Bacto-Gelatin (Fisher Scientific, DF0143-17-9) to 500 mL distilled water in a glass bottle and autoclaving. The gelatin dissolved during the autoclaving step to yield a final concentration of gelatin of 0.02%. One ml Fibronectin (Sigma, F-1141) was diluted in 199 ml of 0.02% gelatin.

Figure 12E:
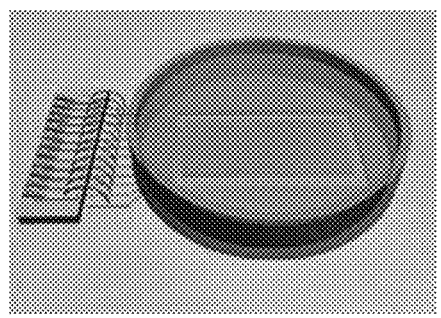
Figure 12F:
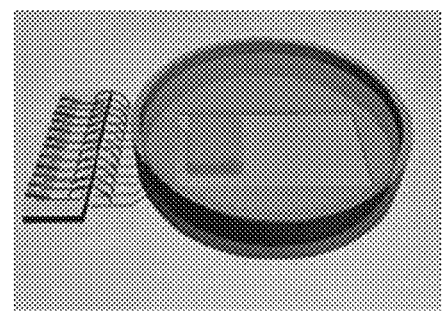
Figure 12G:
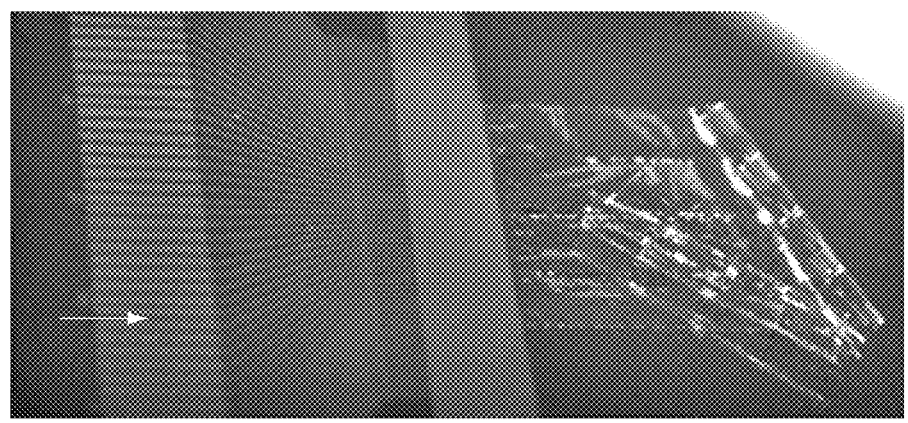
Figure 12H:
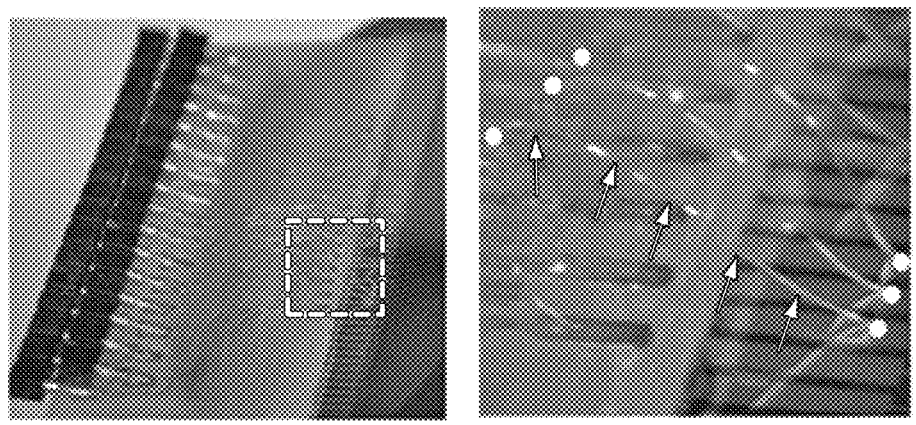

Referring again to FIG. 12, FIG. 12A shows a freestanding mesh-like nanoES; FIG. 12B shows a hybrid of PLGA electrospun fibers and mesh-like nanoES; FIG. 12C shows that individual devices were wire-bonded to PCB connecters; FIG. 12D shows that a modified petri dish was fixed over the scaffold with silicone elastomer; FIG. 12E shows that the hybrid scaffold was sterilized by UV-light illumination for 1 h and soaking in 70% ethanol solution for 0.5 h, coated with fibronectin/gelatin solution overnight and seeded with cardiomyocytes/MATRIGEL™; and FIG. 12F shows that after 1-2 days in culture, the cardiac sheet (from FIG. 12E) was folded and cultivated for an additional 3-10 days. FIG. 12G shows a mesh device showing the freestanding part (the right half) and the fixed part on the wafer (the left half). The arrow marks the outer-electrode pins for wire-bonding. FIG. 12H shows a printed circuit board (PCB) with wire-bonding wires. The wires connected the PCB copper pads (left) and the rectangular electrodes on the supported end of the mesh-like nanoES (right). White dots highlight bonding points. Arrows highlight one wire-bonded aluminum wire.

Cardiac cells were isolated from intact ventricles of 1 to 3-day-old neonatal Sprague/Dawley rats using 3 to 4 cycles (30 min each) of enzyme digestion using collagenase type II and pancreatin. The cells were suspended in culture medium, composed of Medium-199 (Invitrogen, Grand Island, N.Y.) supplemented with 0.6 mM $CuSO_4.5H_2O$, 0.5 mM $ZnSO_4.7H_2O$, 1.5 mM vitamin B12, 500 U $ml^{-1}$ penicillin, 100 mg $ml^{-1}$ streptomycin and 5 vol % fetal calf serum (FCS). The cardiac cells were finally seeded with 5-10 mg/ml MATRIGEL™ onto fibronectin/gelatin coated PLGA/mesh nanoES at an initial cell density of $3-6\times10^7$ $cm^{-2}$ (FIG. 12E). After 1-2 days, the cell-seeded nanoES was manually folded into a construct, and was maintained at 37° C. with 5% $CO_2$ for an additional 3-8 days (FIG. 12F), with medium changes every 2-3 days. All animal procedures conformed to US National Institutes of Health guidelines and were approved by Harvard University's Animal Care and Use Committee.

Figure 18A:
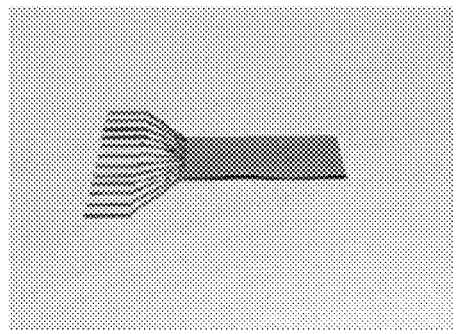
FIGS. 18A-18H schematically illustrate growing cells on a vascular cell scaffold, in another embodiment of the invention.
Figure 18B:
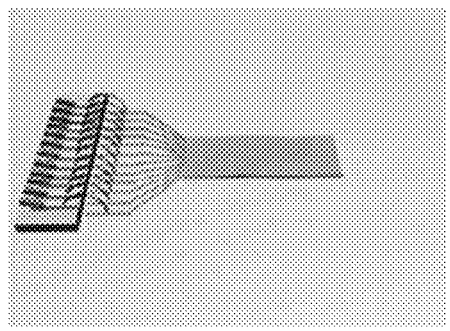
Figure 18C:
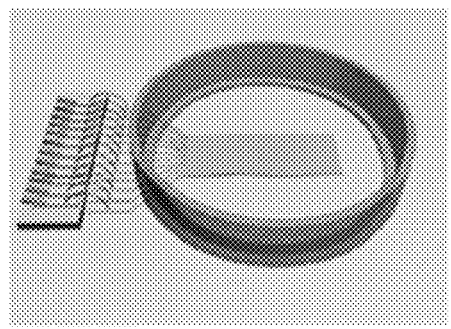
Figure 18D:
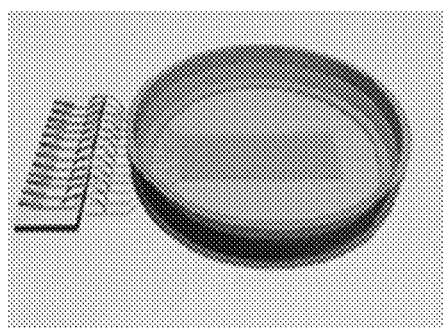
Figure 18E:
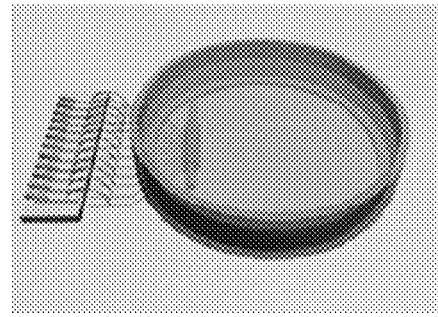

Vascular constructs. Synthetic vascular constructs were produced in a manner similar to the sheet-based tissue engineering approach described previously (FIG. 18). First, the mesh nanoES were coated with gelatin/fibronectin solution overnight (FIGS. 18A-18C). Second, human aortic smooth muscle cells (HASMC, Invitrogen, Grand Island, N.Y.) were seeded at a density of $1\times10^4$ $cm^{-2}$ on the gelatin/fibronectin-coated devices and cultured in Medium 231 (Invitrogen, Grand Island, N.Y.) supplemented with smooth muscle growth supplement (SMGS, Invitrogen) (FIG. 14D). Sodium L-ascorbate (50 micrograms/mL, Sigma) was added to the culture medium to stimulate extracellular matrix (ECM) synthesis. HASMCs were maintained at 37° C. with 5% $CO_2$ until their secreted ECM proteins formed an cohesive tissue sheet (7-14 days) that can be easily peeled off from the silicon substrate. The cell-coated mesh nanoES was then gently lifted from the $SiO_2$ substrate using fine forceps, rolled onto a polystyrene or glass tubular support 1.5 mm in diameter, then maintained in culture Medium 231 supplemented with SMGS and 50 micrograms/mL sodium L-ascorbate for at least another 2 weeks for maturation of the vascular structure (FIG. 18E).

Figure 18F:
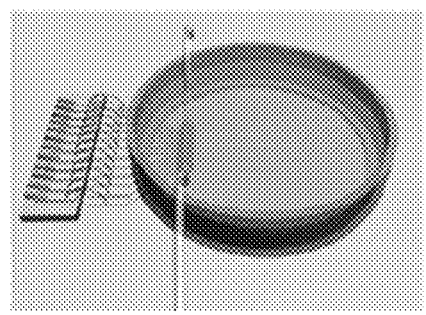
Figure 18G:
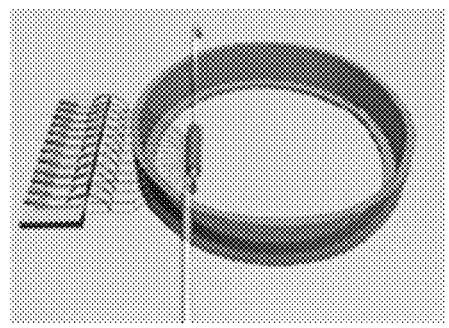
Figure 18H:
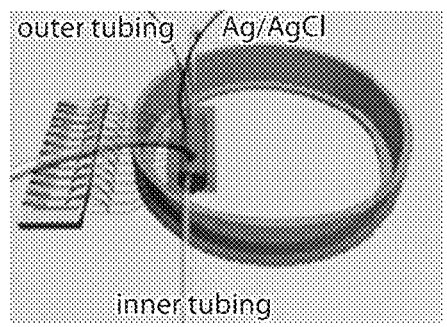

0.5-2 h prior to pH sensing experiments, the temporary tubular support was removed, and segments of polystyrene tubing (the inner tubing in FIG. 17F, inset) were connected to the open ends of the vascular construct (FIG. 18F), and a PDMS fluidic chamber with input/output tubing and Ag/AgCl electrodes (FIG. 17F, inset) was sealed with the silicon substrate and the vascular construct using silicone elastomer glue (Kwik-Sil, World Precision Instruments, Inc.) as shown in FIG. 18H. Fresh medium was delivered to the vascular construct through both inner and outer tubing. The pH of the solution delivered through the outer tubing was varied during the experiment.

FIG. 18A shows a free-standing mesh-like nanoES; FIG. 18B shows that individual devices were wirebonded to PCB connecters; FIG. 18C shows that a modified petri-dish was fixed over the scaffold with silicone elastomer; FIG. 18D shows that the hybrid scaffold was sterilized with UV-light illumination for 1 h and soaking in 70% ethanol solution for 0.5 h, coated with fibronectin/gelatin solution overnight and seeded with HASMCs; FIG. 18E shows that after 7-14 days in culture, the HASMC-seeded nanoES (from FIG. 18D) was rolled against a tubular support and cultivated for at least another 14 days; FIG. 18F shows that the tubular support was removed and tubing was connected to the ends of the lumen of the HASMC construct; FIG. 18G shows that the medium was removed while keeping the construct moist; and FIG. 18H shows that a PDMS chamber was assembled around the construct, attached to tubing to bathe the outside of the construct and Ag/AgCl electrodes to measure pH in the bathing fluid.

Immunochemical staining. Cells were fixed with 4% paraformaldehyde (Electron Microscope Sciences, Hatfield, Pa.) in PBS for 15-30 min, followed by 2-3 washes with ice-cold PBS. Cells were pre-blocked and permeabilized (0.2-0.25% Triton X-100 and 10% feral bovine serum or 1% bovine serum albumin (BSA) in PBS) for 1 hour at room temperature. Next, the cells were incubated with primary antibodies in 1% BSA in 1×PBS with 0.1% (v/v) Tween 20 (PBST) for 1 hr at room temperature or overnight at 4° C. Then cells were incubated with the secondary antibodies with fluorophores. For counter-staining of cell nuclei, cells were incubated with 0.1-1 microgram/mL Hoechst 34580 (Molecular Probes, Invitrogen, Grand Island, N.Y.) for 1 min. Specific reagents used for different cell types were as follows. Neurons: neuronal class III beta-Tubulin (TUJ1) mouse monoclonal antibody (1:500 dilution, Covance Inc., Princeton, N.J.) and AlexaFluor-546 goat anti-mouse IgG (1:1000, Invitrogen, Grand Island, N.Y.) were used as the primary and secondary antibodies, respectively. Cardiomyocytes: anti-alpha-actinin mouse monoclonal antibody (1:450; Clone EA-53, Sigma-Aldrich Corp., St. Louis, Mo.) and AlexaFluor-488 goat anti-mouse (1:200; Molecular Probes, Invitrogen, Grand Island, N.Y.) were used as the primary and secondary antibodies, respectively. Hoechst 34580 was used to counter-stain cell nuclei. HASMC: anti-smooth muscle alpha-actin rabbit polyclonal antibody (1:500, Abcam, Cambridge, Mass.) and AlexaFluor-488 donkey anti-rabbit antibody (1:200; Molecular Probes, Invitrogen, Grand Island, N.Y.) were used as the primary and secondary antibodies, respectively. Hoechst 34580 was used to counter-stain cell nuclei.

Fluorescent dye labeling of devices and PLGA fibers. Fluorescence images of the reticular nanoES (FIGS. 4B and 6A) were obtained by doping the SU-8 resist solution with rhodamine 6G (Sigma-Aldrich Corp., St. Louis, Mo.) at a concentration less than 1 microgram/mL before deposition and patterning. PLGA electrospun fiber scaffolds were labeled by physical absorption of rhodamine 6G from an aqueous solution (0.1 mg/mL), and then rinsed copiously with water before fluorescence imaging.

Hematoxylin-eosin and Masson trichrome staining. The vascular constructs were cut and fixed in formalin solution (10%, neutral buffered, Sigma-Aldrich Corp., St. Louis, Mo.). The fixed sample was dehydrated in a series of graded ethanol baths (70% ethanol for 1 h, 95% ethanol for 1 h, absolute ethanol 3× times, 1 h each) and xylenes (2×, 1 h each), and then infiltrated with molten paraffin (HistoStar, Thermo Scientific, Kalamazoo, Mich.) at 58° C. for 2 h. The infiltrated tissues were embedded into paraffin blocks and cut into 5-6 micrometer sections. Immediately prior to straining, the paraffin was removed from the sections by 2 washes with xylene, 1 min each. Then the sections were rehydrated by a 5 min wash in absolute ethanol, 2 min in 95% ethanol, 2 min in 70% ethanol and 5 min in distilled water. Standard hematoxylin and eosin staining was carried out using an automated slide stainer (Varistain Gemini ES, Thermo Scientific, Kalamazoo, Mich.). Collagen secretion by HASMCs was assessed on deparaffinized sections using a Masson's trichrome staining kit (Polysciences, Inc., Warrington, Pa.) according to standard protocols.

Optical microscopy and image analysis. Confocal and epi-fluorescence imaging were carried out using an Olympus Fluoview FV1000 confocal laser scanning microscope. Confocal images were acquired using 405, 473 and 559 nm wavelength lasers to excite cellular components labeled with Hoechst 34580, AlexaFluor-488/Rodamine-6G, and Rodamine-6G/AlexaFluor-546 fluorescent dyes (Molecular Probes and Sigma-Aldrich Corp.), respectively. A 635 nm wavelength laser was used for imaging metal interconnects in reflective mode. Epi-fluorescence images were acquired using a mercury lamp together with standard DAPI (EX: 377/50, EM: 447/60), GFP (EX: 473/31, EM 520/35) and TRITC (EX: 525/40, EM: 585/40) filters. ImageJ (ver. 1.45i, Wayne Rasband, National Institutes of Health, USA) was used for 3D reconstruction and analysis of the confocal and epi-fluorescence images. Bright-field optical micrographs of histological samples were acquired on an Olympus FSX100 system using FSXBSW software (ver. 02.02).

Micro-computed tomography. The nanoES in the synthetic vascular construct was imaged using a HMXST Micro-CT x-ray imaging system with a standard horizontal imaging axis cabinet (model: HMXST225, Nikon Metrology, Inc., Brighton, Mich.). Prior to imaging, samples were fixed and dried. In a typical imaging process, 60-70 kV acceleration voltage and 130-150 microamperes electron beam current was used. No filter was used. VGStudio MAX (ver. 2.0, Volume Graphics GMbh, Germany) was used for 3D reconstruction and analysis of the micro-CT images.

Cell viability assays. Hippocampal neuron viability was evaluated using a LIVE/DEAD® Viability/Cytotoxicity Kit (Molecular Probes, Invitrogen, Grand Island, N.Y.). On days 7, 14 and 21 of the culture, neurons were incubated with 1 micromolar calcein-AM and 2 micromolar ethidium homodimer-1 (EthD-1) for 45 min at 37° C. to label live and dead cells, respectively. Cell viability at each time point was calculated as live/(live+dead)×100, and was normalized to the percentage of live cells on day 0 ($live_{day\ n}/live_{day\ 0}$). Three-dimensional neuron cultures in MATRIGEL™ on polylysine modified glass slides (Fisher Scientific Inc., Waltham, Mass.) were used as controls. The cells were imaged with a confocal fluorescence microscope (Olympus Fluoview FV1000) and the 3D reconstructed images were used for live/dead cell counting. For each group, n=6. In 3D cardiac cultures, cell viability was evaluated with an assay of a mitochondrial metabolic activity, the CELLTITER 96® AQueous One Solution Cell Proliferation Assay (Promega Corp., Madison, Wis.) that uses a tetrazolium compound (3-(4,5-dimethyl-2-yl)-5-(3-carboxymethoxyphenyl)-2-(4-sulfophenyl)-2H-tetrazolium, inner salt; MTS) and an electron coupling reagent (phenazine ethosulfate; PES). On days 2, 4, 6, 8, 10 and 12 of the culture, cardiac constructs were incubated with CELLTITER 96® AQueous One Solution for 120 min at 37° C. The absorbance of the culture medium at 490 nm was immediately recorded with a 96-well plate reader. The quantity of formazan product (converted from tetrazole) as measured by the absorbance at 490 nm was directly proportional to cell metabolic activity in culture. Three-dimensional cardiomyocyte cultures in MATRIGEL™ on gelatin coated electrospun PLGA fibers were used as controls. For each group, n=6.

Electrical measurements. The nanowire FET conductance and transconductance (sensitivity) were measured in 1×PBS. The slope of a linear fit to conductance versus water-gate potential ($V_{gate}$) data was used to determine transconductance. For NWFET stability tests, the reticular NWFET devices were maintained under neuron culture conditions (see details above, in Neuron culture) for predetermined intervals. Electrical transport measurements and recordings from 3D cardiomyocyte-seeded nanoES were obtained in Tyrode solution (pH~7.3) with a 100 mV DC source voltage at 25° C. or 37° C. The current was amplified with a multi-channel current/voltage preamplifier, filtered with a 3 kHz low pass filter (CyberAmp 380), and digitized at a 50 kHz sampling rate (Axon Digi1440A). In extravascular pH sensing experiments, a single polydimethylsiloxane (PDMS) microfluidic chamber was used to deliver two flows of phosphate buffer solutions: the pH delivered by the outer input tubing was varied, while that of the inner tubing was fixed at 7.4. In the pH-sensing experiments, nanoelectronic devices were modulated using a lock-in amplifier with a modulation frequency of 79 and 39 Hz, time constant of 30 ms, amplitude of 30 mV, and DC source-drain potential of zero. Ag/AgCl reference electrodes were used in all recording and sensing experiments.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    forming one or more polymeric constructs on a substrate using e-beam lithography, wherein the polymeric constructs comprise one or more nanoscale wires;
    removing at least a portion of the substrate from the one or more polymeric constructs;
    rolling the one or more polymeric constructs into a rolled-up tubular 3-dimensional structure; and
    connecting the one or more nanoscale wires within the rolled-up tubular 3-dimensional structure to an external electrical circuit, wherein the one or more nanoscale wires within the rolled-up tubular 3-dimensional structure are individually electronically addressable.

2. The method of claim 1, further comprising a sacrificial material positioned on the substrate.

3. The method of claim 2, wherein the sacrificial material comprises nickel.

4. The method of claim 2, further comprising depositing the sacrificial material on the substrate, prior to forming the one or more polymeric constructs on a substrate.

5. The method of claim 4, wherein forming the one or more polymeric constructs on the substrate comprises:
   depositing one or more bedding polymers on at least a portion of the sacrificial material as one or more layers; and
   depositing one or more nanoscale wires on at least a portion of an uppermost layer of the bedding polymers.

6. The method of claim 5, wherein at least one of the bedding polymers comprises a photoresist.

7. The method of claim 5, comprising:
   depositing a first bedding polymer on at least a portion of the sacrificial material;
   depositing a second bedding polymer on at least a portion of the first bedding polymer; and
   depositing one or more nanoscale wires on at least a portion of the second bedding polymer.

8. The method of claim 5, further comprising aligning the deposited nanoscale wires.

9. The method of claim 2, further comprising removing at least a portion of the sacrificial material.

10. The method of claim 9, wherein upon removing at least a portion of the sacrificial material, the one or more polymeric constructs spontaneously rolls into the 3-dimensional structure.

11. The method of claim 1, further comprising forming one or more metal leads on the polymeric material.

12. The method of claim 11, wherein forming one or more metal leads comprises:
   depositing one or more lead polymers on at least some of the one or more the nanoscale wires;
   depositing one or more metals on at least a portion of the one or more lead polymers; and
   removing a portion of the one or more metals to form the one or more metal leads.

13. The method of claim 12, wherein depositing one or more metals on at least a portion of the one or more lead polymers comprises:
   depositing a first metal on the one or more lead polymers; and
   depositing a second metal on at least a portion of the first metal.

14. The method of claim 13, further comprising depositing a third metal on at least a portion of the second metal.

15. The method of claim 14, wherein the first metal, the second metal, and the third metal are deposited in a pre-stressed arrangement.

16. The method of claim 11, further comprising connecting the one or more metal leads to an external electrical circuit.

17. The method of claim 1, wherein the one or more polymeric constructs comprises a biocompatible polymer layer.

18. The method of claim 1, further comprising depositing an extracellular matrix protein on at least a portion of the one or more polymeric constructs.

19. The method of claim 1, further comprising seeding one or more cells onto the one or more polymeric constructs.

20. The method of claim 1, further comprising exposing the one or more polymeric constructs to a cell growth medium.

21. The method of claim 1, wherein the one or more nanoscale wires within the rolled-up tubular 3-dimensional structure are connectable to an external electrical circuit via one or more metal leads on the polymeric material.

22. The method of claim 1, wherein the one or more nanoscale wires within the rolled-up tubular 3-dimensional structure form an internal electrical circuit.

* * * * *